US009888972B2

(12) United States Patent
Brewster et al.

(10) Patent No.: US 9,888,972 B2
(45) Date of Patent: Feb. 13, 2018

(54) SYSTEMS AND METHODS FOR SELECTING, ACTIVATING, OR SELECTING AND ACTIVATING TRANSDUCERS

(71) Applicant: Kardium Inc., Burnaby (CA)

(72) Inventors: Jeffery Charles Brewster, Burnaby (CA); Daniel Martin Reinders, Richmond (CA); Daniel Robert Weinkam, Coquitlam (CA)

(73) Assignee: KARDIUM INC., Burnaby (CA)

( * ) Notice: Subject to any disclaimer, the term of this patent is extended or adjusted under 35 U.S.C. 154(b) by 0 days.

(21) Appl. No.: 15/254,207

(22) Filed: Sep. 1, 2016

(65) Prior Publication Data
US 2016/0367325 A1 Dec. 22, 2016

Related U.S. Application Data

(63) Continuation of application No. 14/686,408, filed on Apr. 14, 2015, now Pat. No. 9,445,862, which is a
(Continued)

(51) Int. Cl.
*A61B 5/02* (2006.01)
*A61B 5/042* (2006.01)
(Continued)

(52) U.S. Cl.
CPC ............ *A61B 34/25* (2016.02); *A61B 5/026* (2013.01); *A61B 5/042* (2013.01); *A61B 5/0422* (2013.01);
(Continued)

(58) Field of Classification Search
None
See application file for complete search history.

(56) References Cited

U.S. PATENT DOCUMENTS 4,114,202 A 9/1978 Roy et al.
4,164,046 A 8/1979 Cooley
(Continued)

FOREIGN PATENT DOCUMENTS

EP 0723467 B1 4/2002
EP 1645234 A1 4/2006
(Continued)

OTHER PUBLICATIONS

Examination Report issued in European Patent Application No. 13793690.2, dated Nov. 17, 2016.
(Continued)

*Primary Examiner* — Brian T Gedeon
(74) *Attorney, Agent, or Firm* — Rossi, Kimms & McDowell LLP

(57) ABSTRACT

Transducer-based systems can be configured to display a graphical representation of a transducer-based device, the graphical representation including graphical elements corresponding to transducers of the transducer-based device, and also including between graphical elements respectively associated with a set of the transducers and respectively associated with a region of space between the transducers of the transducer-based device. Selection of graphical elements and/or between graphical elements can cause activation of the set of transducers associated with the selected elements. Selection of a plurality of graphical elements and/or between graphical elements can cause visual display of a corresponding activation path in the graphical representation. Visual characteristics of graphical elements and between graphical elements can change based on an activation-status of the corresponding transducers. Activation requests for a set of transducers can be denied if it is determined that a transducer in the set of transducers is unacceptable for activation.

71 Claims, 21 Drawing Sheets

Related U.S. Application Data continuation of application No. 13/792,670, filed on Mar. 11, 2013, now Pat. No. 9,011,423.

(60) Provisional application No. 61/723,311, filed on Nov. 6, 2012, provisional application No. 61/670,881, filed on Jul. 12, 2012, provisional application No. 61/649,734, filed on May 21, 2012.

(51) Int. Cl.
| | |
|---|---|
| *A61B 5/00* | (2006.01) |
| *A61B 18/12* | (2006.01) |
| *A61B 34/00* | (2016.01) |
| *A61B 5/053* | (2006.01) |
| *A61B 18/14* | (2006.01) |
| *A61N 1/372* | (2006.01) |
| *G06F 3/0482* | (2013.01) |
| *G06F 3/0484* | (2013.01) |
| *A61B 5/026* | (2006.01) |
| *A61B 5/01* | (2006.01) |
| *A61N 1/362* | (2006.01) |
| *A61B 18/00* | (2006.01) |
| *A61B 17/00* | (2006.01) |

(52) U.S. Cl.
CPC ............ *A61B 5/053* (2013.01); *A61B 5/0538* (2013.01); *A61B 5/6858* (2013.01); *A61B 5/743* (2013.01); *A61B 5/7435* (2013.01); *A61B 18/1206* (2013.01); *A61B 18/1233* (2013.01); *A61B 18/14* (2013.01); *A61B 18/1492* (2013.01); *A61N 1/37264* (2013.01); *G06F 3/0482* (2013.01); *G06F 3/04842* (2013.01); *A61B 5/01* (2013.01); *A61B 5/6869* (2013.01); *A61B 2017/00199* (2013.01); *A61B 2018/00267* (2013.01); *A61B 2018/00351* (2013.01); *A61B 2018/00357* (2013.01); *A61B 2018/00363* (2013.01); *A61B 2018/00577* (2013.01); *A61B 2018/00642* (2013.01); *A61B 2018/00648* (2013.01); *A61B 2018/00708* (2013.01); *A61B 2018/00797* (2013.01); *A61B 2018/00839* (2013.01); *A61B 2018/00863* (2013.01); *A61B 2018/00875* (2013.01); *A61B 2018/00892* (2013.01); *A61B 2018/00904* (2013.01); *A61B 2018/00988* (2013.01); *A61B 2018/124* (2013.01); *A61B 2034/254* (2016.02); *A61N 1/362* (2013.01)

(56) References Cited

U.S. PATENT DOCUMENTS

| | | |
|---|---|---|
| 4,225,148 A | 9/1980 | Andersson |
| 4,240,441 A | 12/1980 | Khalil |
| 4,263,680 A | 4/1981 | Reul et al. |
| 4,273,128 A | 6/1981 | Lary |
| 4,411,266 A | 10/1983 | Cosman |
| 4,490,859 A | 1/1985 | Black et al. |
| 4,543,090 A | 9/1985 | McCoy |
| 4,699,147 A | 10/1987 | Chilson et al. |
| 4,770,187 A | 9/1988 | Lash et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,921,499 A | 5/1990 | Hoffman et al. |
| 4,940,064 A | 7/1990 | Desai |
| 4,942,788 A | 7/1990 | Farr et al. |
| 4,979,514 A | 12/1990 | Sekii et al. |
| 4,998,933 A | 3/1991 | Eggers et al. |
| 5,026,384 A | 6/1991 | Farr et al. |
| 5,047,047 A | 9/1991 | Yoon |
| 5,122,137 A | 6/1992 | Lennox |
| 5,127,902 A | 7/1992 | Fischell |
| 5,156,151 A | 10/1992 | Imran |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,201,316 A | 4/1993 | Pomeranz et al. |
| 5,228,442 A | 7/1993 | Imran |
| 5,242,386 A | 9/1993 | Holzer |
| 5,255,679 A | 10/1993 | Imran |
| 5,279,299 A | 1/1994 | Imran |
| 5,293,869 A | 3/1994 | Edwards et al. |
| 5,312,435 A | 5/1994 | Nash et al. |
| 5,317,952 A | 6/1994 | Immega |
| 5,327,889 A | 7/1994 | Imran |
| 5,341,807 A | 8/1994 | Nardella |
| 5,366,443 A | 11/1994 | Eggers et al. |
| 5,379,773 A | 1/1995 | Hornsby |
| 5,419,767 A | 5/1995 | Eggers et al. |
| 5,450,860 A | 9/1995 | O'Connor |
| 5,478,353 A | 12/1995 | Yoon |
| 5,496,267 A | 3/1996 | Drasler et al. |
| 5,531,760 A | 7/1996 | Alwafaie |
| 5,545,193 A | 8/1996 | Fleischman et al. |
| 5,557,967 A | 9/1996 | Renger |
| 5,593,424 A | 1/1997 | Northrup, III |
| 5,598,848 A | 2/1997 | Swanson et al. |
| 5,599,345 A | 2/1997 | Edwards et al. |
| 5,620,481 A | 4/1997 | Desai et al. |
| 5,662,587 A | 9/1997 | Grundfest et al. |
| 5,681,308 A | 10/1997 | Edward et al. |
| 5,681,336 A | 10/1997 | Clement et al. |
| 5,687,723 A | 11/1997 | Avitall |
| 5,687,737 A | 11/1997 | Branham et al. |
| 5,697,285 A | 12/1997 | Nappi et al. |
| 5,713,896 A | 2/1998 | Nardella |
| 5,713,942 A | 2/1998 | Stern et al. |
| 5,716,397 A | 2/1998 | Myers |
| 5,720,726 A | 2/1998 | Marcadis et al. |
| 5,728,114 A | 3/1998 | Evans et al. |
| 5,730,127 A | 3/1998 | Avitall |
| 5,762,066 A | 6/1998 | Law et al. |
| 5,769,846 A | 6/1998 | Edwards et al. |
| 5,782,239 A | 7/1998 | Webster, Jr. |
| 5,782,879 A | 7/1998 | Rosborough et al. |
| 5,800,495 A | 9/1998 | Machek et al. |
| 5,810,802 A | 9/1998 | Panescu et al. |
| 5,824,066 A | 10/1998 | Gross |
| 5,836,990 A | 11/1998 | Li |
| 5,876,343 A | 3/1999 | Teo |
| 5,881,727 A | 3/1999 | Edwards |
| 5,891,136 A | 4/1999 | McGee et al. |
| 5,904,711 A | 5/1999 | Flom et al. |
| 5,916,163 A | 6/1999 | Panescu et al. |
| 5,919,207 A | 7/1999 | Taheri |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,961,440 A | 10/1999 | Schweich, Jr. et al. |
| 5,968,040 A | 10/1999 | Swanson et al. |
| 5,984,950 A | 11/1999 | Cragg et al. |
| 6,001,069 A | 12/1999 | Tachibana et al. |
| 6,014,581 A | 1/2000 | Whayne et al. |
| 6,104,944 A | 8/2000 | Martinelli |
| 6,138,043 A | 10/2000 | Avitall |
| 6,142,993 A | 11/2000 | Whayne et al. |
| 6,156,046 A | 12/2000 | Passafaro et al. |
| 6,210,432 B1 | 4/2001 | Solem et al. |
| 6,216,043 B1 | 4/2001 | Swanson et al. |
| 6,217,573 B1 | 4/2001 | Webster |
| 6,241,747 B1 | 6/2001 | Ruff |
| 6,248,124 B1 | 6/2001 | Pedros et al. |
| 6,258,258 B1 | 7/2001 | Sartori |

(56) References Cited

U.S. PATENT DOCUMENTS

| | | |
|---|---|---|
| 6,266,550 B1 | 7/2001 | Selmon et al. |
| 6,304,769 B1 | 10/2001 | Arenson et al. |
| 6,306,135 B1 | 10/2001 | Ellmam et al. |
| 6,308,091 B1 | 10/2001 | Avitall |
| 6,319,249 B1 | 11/2001 | Töllner |
| 6,346,105 B1 | 2/2002 | Tu et al. |
| 6,350,263 B1 | 2/2002 | Wetzig et al. |
| 6,358,258 B1 | 3/2002 | Arcia et al. |
| 6,383,151 B1 | 5/2002 | Diederich et al. |
| 6,389,311 B1 | 5/2002 | Whayne et al. |
| 6,391,024 B1 | 5/2002 | Sun et al. |
| 6,391,048 B1 | 5/2002 | Ginn et al. |
| 6,391,054 B2 | 5/2002 | Carpentier et al. |
| 6,402,781 B1 | 6/2002 | Langberg et al. |
| 6,436,052 B1 | 8/2002 | Nikolic et al. |
| 6,475,223 B1 | 11/2002 | Werp et al. |
| 6,485,409 B1 | 11/2002 | Voloshin et al. |
| 6,485,489 B2 | 11/2002 | Teirstein et al. |
| 6,506,210 B1 | 1/2003 | Kanner |
| 6,514,249 B1 | 2/2003 | Maguire et al. |
| 6,529,756 B1 | 3/2003 | Phan et al. |
| 6,537,198 B1 | 3/2003 | Vidlund et al. |
| 6,537,314 B2 | 3/2003 | Langberg et al. |
| 6,540,670 B1 | 4/2003 | Hirata et al. |
| 6,551,312 B2 | 4/2003 | Zhang et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,589,208 B2 | 7/2003 | Ewers et al. |
| 6,626,930 B1 | 9/2003 | Allen et al. |
| 6,632,238 B2 | 10/2003 | Ginn et al. |
| 6,635,056 B2 | 10/2003 | Kadhiresan et al. |
| 6,640,119 B1 | 10/2003 | Budd et al. |
| 6,662,034 B2 | 12/2003 | Segner et al. |
| 6,704,590 B2 | 3/2004 | Haldeman |
| 6,723,038 B1 | 4/2004 | Schroeder et al. |
| 6,726,716 B2 | 4/2004 | Marquez |
| 6,760,616 B2 | 7/2004 | Hoey et al. |
| 6,780,197 B2 | 8/2004 | Roe et al. |
| 6,788,969 B2 | 9/2004 | Dupree et al. |
| 6,797,001 B2 | 9/2004 | Mathis et al. |
| 6,800,090 B2 | 10/2004 | Alferness et al. |
| 6,837,886 B2 | 1/2005 | Collins et al. |
| 6,852,076 B2 | 2/2005 | Nikolic et al. |
| 6,855,143 B2 | 2/2005 | Davison et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,942,657 B2 | 9/2005 | Sinofsky et al. |
| 6,949,122 B2 | 9/2005 | Adams et al. |
| 6,960,229 B2 | 11/2005 | Mathis et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,994,093 B2 | 2/2006 | Murphy et al. |
| 6,997,951 B2 | 2/2006 | Solem et al. |
| 7,001,383 B2 | 2/2006 | Keidar |
| 7,025,776 B1 | 4/2006 | Houser et al. |
| 7,048,734 B1 | 5/2006 | Fleischman et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,141,019 B2 | 11/2006 | Pearlman |
| 7,144,363 B2 | 12/2006 | Pai et al. |
| 7,177,677 B2 | 2/2007 | Kaula et al. |
| 7,186,210 B2 | 3/2007 | Feld et al. |
| 7,187,964 B2 | 3/2007 | Khoury |
| 7,189,202 B2 | 3/2007 | Lau et al. |
| 7,279,007 B2 | 10/2007 | Nikolic et al. |
| 7,300,435 B2 | 11/2007 | Wham et al. |
| 7,303,526 B2 | 12/2007 | Sharkey et al. |
| 7,335,196 B2 | 2/2008 | Swanson et al. |
| 7,507,252 B2 | 3/2009 | Lashinski et al. |
| 7,530,980 B2 | 5/2009 | Hooven |
| 7,738,967 B2 | 6/2010 | Salo |
| 8,103,338 B2 | 1/2012 | Harlev et al. |
| 8,150,499 B2 | 4/2012 | Gelbart et al. |
| 8,224,432 B2 | 7/2012 | MacAdam et al. |
| 8,398,626 B2 | 3/2013 | Buysse et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2002/0002329 A1 | 1/2002 | Avitall |
| 2002/0016628 A1 | 2/2002 | Langberg et al. |
| 2002/0087156 A1 | 7/2002 | Maguire et al. |
| 2002/0087173 A1 | 7/2002 | Alferness et al. |
| 2002/0099415 A1 | 7/2002 | Panescu et al. |
| 2002/0107478 A1 | 8/2002 | Wendlandt |
| 2002/0107511 A1 | 8/2002 | Collins et al. |
| 2002/0115941 A1 | 8/2002 | Whayne et al. |
| 2002/0115944 A1 | 8/2002 | Mendes et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2003/0028118 A1 | 2/2003 | Dupree et al. |
| 2003/0028183 A1 | 2/2003 | Sanchez et al. |
| 2003/0050685 A1 | 3/2003 | Nikolic et al. |
| 2003/0055420 A1 | 3/2003 | Kadhiresan et al. |
| 2003/0069570 A1 | 4/2003 | Witzel et al. |
| 2003/0069573 A1 | 4/2003 | Kadhiresan et al. |
| 2003/0069636 A1 | 4/2003 | Solem et al. |
| 2003/0078465 A1 | 4/2003 | Pai et al. |
| 2003/0078671 A1 | 4/2003 | Lesniak et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0181819 A1 | 9/2003 | Desai |
| 2003/0212395 A1 | 11/2003 | Woloszko et al. |
| 2003/0229395 A1 | 12/2003 | Cox |
| 2004/0002626 A1 | 1/2004 | Feld et al. |
| 2004/0054279 A1 | 3/2004 | Hanley |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0158321 A1 | 8/2004 | Reuter et al. |
| 2004/0176797 A1 | 9/2004 | Opolski |
| 2004/0186566 A1 | 9/2004 | Hindrichs et al. |
| 2004/0215232 A1 | 10/2004 | Belhe et al. |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0080402 A1 | 4/2005 | Santamore et al. |
| 2005/0096047 A1 | 5/2005 | Haberman et al. |
| 2005/0096647 A1 | 5/2005 | Steinke et al. |
| 2005/0107723 A1 | 5/2005 | Wehman et al. |
| 2005/0107871 A1 | 5/2005 | Realyvasques et al. |
| 2005/0125030 A1 | 6/2005 | Forsberg et al. |
| 2005/0148892 A1 | 7/2005 | Desai |
| 2005/0149014 A1 | 7/2005 | Hauck et al. |
| 2005/0154252 A1 | 7/2005 | Sharkey et al. |
| 2005/0182365 A1 | 8/2005 | Hennemann |
| 2005/0187620 A1 | 8/2005 | Pai et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203558 A1 | 9/2005 | Maschke |
| 2005/0209636 A1 | 9/2005 | Widomski et al. |

(56) References Cited

U.S. PATENT DOCUMENTS

| | | |
|---|---|---|
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0261580 A1 | 11/2005 | Willis et al. |
| 2005/0267574 A1 | 12/2005 | Cohn et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025800 A1 | 2/2006 | Suresh |
| 2006/0030881 A1 | 2/2006 | Sharkey et al. |
| 2006/0085049 A1 | 4/2006 | Cory et al. |
| 2006/0089637 A1 | 4/2006 | Werneth et al. |
| 2006/0135968 A1 | 6/2006 | Schaller |
| 2006/0135970 A1 | 6/2006 | Schaller |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0264980 A1 | 11/2006 | Khairkhahan et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0016068 A1 | 1/2007 | Grunwald et al. |
| 2007/0038208 A1 | 2/2007 | Kefer |
| 2007/0083193 A1 | 4/2007 | Werneth et al. |
| 2007/0083195 A1 | 4/2007 | Werneth et al. |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0161846 A1 | 7/2007 | Nikolic et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0249999 A1 | 10/2007 | Sklar et al. |
| 2007/0270688 A1 | 11/2007 | Gelbart et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0045778 A1 | 2/2008 | Lichtenstein et al. |
| 2008/0071298 A1 | 3/2008 | Khairkhahan et al. |
| 2008/0281322 A1 | 11/2008 | Sherman et al. |
| 2008/0312713 A1 | 12/2008 | Wilfley et al. |
| 2009/0018617 A1 | 1/2009 | Skelton et al. |
| 2009/0069704 A1 | 3/2009 | MacAdam et al. |
| 2009/0131930 A1 | 5/2009 | Gelbart et al. |
| 2009/0157058 A1 | 6/2009 | Ferren et al. |
| 2009/0192441 A1 | 7/2009 | Gelbart et al. |
| 2009/0287271 A1 | 11/2009 | Blum et al. |
| 2009/0287304 A1 | 11/2009 | Dahlgren et al. |
| 2010/0204694 A1 | 8/2010 | Mehta et al. |
| 2010/0249771 A1 | 9/2010 | Pearson et al. |
| 2010/0268059 A1 | 10/2010 | Ryu et al. |
| 2011/0125172 A1 | 5/2011 | Gelbart et al. |
| 2013/0172884 A1 | 7/2013 | Schoenbach et al. |
| 2013/0310702 A1 | 11/2013 | Reinders et al. |
| 2013/0310826 A1 | 11/2013 | Goertzen et al. |
| 2013/0310827 A1 | 11/2013 | Brewster et al. |
| 2013/0310828 A1 | 11/2013 | Reinders et al. |
| 2015/0065899 A1 | 3/2015 | Reinders et al. |

FOREIGN PATENT DOCUMENTS

| | | |
|---|---|---|
| WO | 95/10320 A1 | 4/1995 |
| WO | 95/20349 A1 | 8/1995 |
| WO | 97/17892 A1 | 5/1997 |
| WO | 03/015611 A2 | 2/2003 |
| WO | 03/077800 A1 | 9/2003 |
| WO | 2004/012629 A1 | 2/2004 |
| WO | 2004/047679 A1 | 6/2004 |
| WO | 2004/084746 A2 | 10/2004 |
| WO | 2004/100803 A1 | 11/2004 |
| WO | 2005/070330 A1 | 8/2005 |
| WO | 2005/102181 A1 | 11/2005 |
| WO | 2006/017809 A2 | 2/2006 |
| WO | 2006/105121 A2 | 10/2006 |
| WO | 2006/135747 A2 | 12/2006 |
| WO | 2006/135749 A2 | 12/2006 |
| WO | 2007/021647 A2 | 2/2007 |
| WO | 2007024983 A2 | 3/2007 |
| WO | 2007/115390 A1 | 10/2007 |
| WO | 2008/002606 A2 | 1/2008 |
| WO | 2009/065042 A2 | 5/2009 |
| WO | 2012033984 A1 | 3/2012 |
| WO | 2012/100184 A2 | 7/2012 |
| WO | 2012/100185 A2 | 7/2012 |
| WO | 2013/176880 A1 | 11/2013 |
| WO | 2013/176881 A1 | 11/2013 |

OTHER PUBLICATIONS

Notice of Allowance issued in U.S. Appl. No. 15/000,491, dated Sep. 2, 2016.
Copending U.S. Appl. No. 15/414,834, filed Jan. 25, 2017.
Goertzen et al., "Systems and Methods for Selecting, Activating, or Selecting and Activating Transducers" Response filed in U.S. Appl. No. 13/792,596, filed Jan. 10, 2017, 21 pgs.
Notice of Allowance issued in U.S. Appl. No. 14/948,924 dated Dec. 21, 2016.
Reinders et al., "Systems and Methods for Activating Transducers" Response to FOA and Terminal Disclaimer filed in U.S. Appl. No. 14/948,924 dated Dec. 12, 2016, 5 pgs.
Reinders et al., "Systems and Methods for Activating Transducers", Amendment After Allowance filed in U.S. Appl. No. 13/792,945 dated Feb. 13, 2015, 14 pages.
Reinders et al., "Systems and Methods for Activating Transducers", Amendment After Allowance filed in U.S. Appl. No. 13/792,781 dated Feb. 13, 2015, 14 pages.
Goertzen et al., "Systems and Methods for Selecting, Activating, or Selecting and Activating Transducers", Response to Restriction Requirement filed in U.S. Appl. No. 13/792,596 dated Jun. 29, 2015, 6 pages.
Brewster et al. "Systems and Methods for Selecting, Activating, or Selecting and Activating Transducers", Preliminary Amendment filed in U.S. Appl. No. 14/686,408 dated May 15, 2015, 8 pages.
Brewster et al., "Systems and Methods for Selecting, Activating, or Selecting and Activating Transducers", Amendment After Allowance filed in U.S. Appl. No. 131792,670 dated Feb. 13, 2015, 11 pages.
Goertzen et al. "Systems and Methods for Selecting, Activating, or Selecting and Activating Transducers", Preliminary Amendment filed in U.S. Appl. No. 13/792,596 dated Feb. 13, 2015, 11 pages.
Becker, et al., "Ablation of Atrial Fibrillation: Energy Sources and Navigation Tools: A Review", Journal of Electrocardiology, Supplement 2004, pp. 55-62, vol. 37.
Buchbinder, Maurice, "Dynamic Mitral Valve Annuloplasty: A Reshapable Ring for Residual and Recurring MR", Foundation for Cardiovascular Medicine, May 24, 2007, La Jolla, CA.
Calkins, Hugh, "Electrophysiology: Radiofrequency Catheter Ablation of Supraventricular Arrhythmias", Education in Heart, 2001; pp. 594-600, vol. 85.
De Ponti, et al., "Non-Fluoroscopic Mapping Systems for Electrophysiology: the Tool or Toy Dilemma After 10 Years", European Heart Journal, 2006; pp. 1134-1136, vol. 27.
Gabriel, et al., "The Dielectric Properties of Biological Tissues: I. Literature Survey", Phys. Med. Biol.; 1996, pp. 2231-2249, vol. 41.
Konings, et al., "Development of an Intravascular Impedance Catheter for Detection of Fatty Lesions in Arteries", IEEE Transactions on Medical Imaging, Aug. 1997, pp. 439-446, vol. 16, No. 4.
Mack, Michael J., "New Techniques for Percutaneous Repair of the Mitral Valve", Heart Fail Rev, 2006; pp. 259-268, vol. 11.

(56) References Cited

OTHER PUBLICATIONS

Otasevic, et al., "First-in-Man Implantation of Left Ventricular Partitioning Device in a Patient With Chronic Heart Failure: Twelve-Month Follow-Up", Journal of Cardiac Failure, 2007, pp. 517-520, vol. 13, No. 7.

Sharkey, et al., "Left Ventricular Apex Occluder. Description of a Ventricular Partitioning Device", EuroIntervention, 2006, pp. 125-127.

Stiles, et al., "Simulated Characterization of Atherosclerotic Lesions in the Coronary Arteries by Measurement of Bioimpedance", IEEE Transactions on Biomedical Engineering, Jul. 2003, pp. 916-921, vol. 50, No. 7.

Tanaka, et al., "Artificial SMA Valve for Treatment of Urinary Incontinence: Upgrading of Valve and Introduction of Transcutaneous Transformer", Bio-Medical Materials and Engineering; 1999, pp. 97-112, vol. 9.

Timek, et al., "Septal-Lateral Annular Cinching Abolishes Acute Ischemic Mitral Regurgitation", Journal of Thoracic and Cardiovascular Surgery, May 2002, pp. 881-888, vol. 123, No. 5.

Timek, et al., "Septal-Lateral Annular Cinching (SLAC) Reduces Mitral Annular Size Without Perturbing Normal Annular Dynamics", Journal of Heart Valve Disease, Jan. 2002, vol. 11, No. 1, pp. 1-9.

Valvano, et al., "Thermal Conductivity and Diffusivity of Biomaterials Measured with Self-Heated Thermistors", International Journal of Thermophysics, 1985, pp. 301-311, vol. 6, No. 3.

Prosecution Documents for U.S. Appl. No. 11/436,584, now abandoned.

Prosecution Documents for U.S. Appl. No. 11/941,819, now published as US 2009-0131930 A1.

Prosecution Documents for U.S. Appl. No. 12/010,458, now published as US 2009-0192441 A1.

Prosecution Documents for U.S. Appl. No. 12/950,871, now patented as U.S. Pat. No. 8,150,499.

Specification and Drawings of U.S. Appl. No. 10/690,131.

International Search Report issued in PCT/US2007/014902 dated Dec. 5, 2007, 5 pages.

International Search Report issued in PCT/US2008/083644 dated Dec. 2, 2009, 5 pages.

International Preliminary Report on Patentability issued in PCT/US2007/014902 dated Jan. 6, 2009, 8 pages.

Written Opinion issued in PCT/US2007/014902 dated Dec. 5, 2007, 7 pages.

Written Opinion issued in PCT/US2008/083644 dated Dec. 2, 2009, 9 pages.

"Waveforms and Segments", Ensite System Instructions for use, 54-06154-001 Rev02, Chapter 7, pp. 85-90 © 2007 St. Jude Medical.

Corrected Notice of Allowability issued in U.S. Appl. No. 13/792,670, dated Mar. 18, 2015, 9 pages.

International Search Report and Written Opinion issued in PCT/CA2013/050350 dated Aug. 2, 2013.

International Search Report and Written Opinion issued in PCT/US2013/039982 dated Sep. 17, 2013.

International Search Report and Written Opinion issued in PCT/US2013/039977 dated Sep. 27, 2013.

Brewster et al., "Systems and Methods for Selecting, Activating, or Selecting and Activating Transducers", Response to Restriction Requirement filed Dec. 23, 2014 for U.S. Appl. No. 13/792,670, 15 pages.

Reinders et al., "Systems and Methods for Activating Transducers", Response to Restriction Requirement filed Dec. 23, 2014 for U.S. Appl. No. 13/792,945, 16 pages.

Reinders et al., "Systems and Methods for Activating Transducers", Notice of Allowance for U.S. Appl. No. 13/792,945 dated Jan. 27, 2015, 49 pages.

Reinders et al., "Systems and Methods for Activating Transducers", Response to Restriction Requirement filed Dec. 23, 2014 for U.S. Appl. No. 13/792,781, 15 pages.

Reinders et al., "Systems and Methods for Activating Transducers", Notice of Allowance dated Feb. 3, 2015 for U.S. Appl. No. 13/792,781, 52 pages.

Brewster et al., "Systems and Methods for Selecting, Activating, or Selecting and Activating Transducers", Notice of Allowance dated Feb. 4, 2015 for U.S. Appl. No. 13/792,670, 47 pages.

Partial Supplementary European Search Report issued in EP13794418.7, dated Jun. 1, 2015.

Extended European Search Report issued in EP13793690.2, dated May 22, 2015.

Extended European Search Report issued in corresponding EP13794418.7, dated Sep. 16, 2015, 12 pages.

Office Action issued in U.S. Appl. No. 14/686,408, dated Oct. 2, 2015.

Non-Final Office Action issued in co-pending U.S. Appl. No. 14/686,457, dated Sep. 30, 2015.

Goertzen et al., "Systems and Methods for Selecting, Activating, or Selecting and Activating Transducers", Office Action for U.S. Appl. No. 13/792,596 dated Nov. 24, 2015, 64 pages.

Notice of Allowance issued in U.S. Appl. No. 14/686,408, dated May 11, 2016.

Office Action issued in U.S. Appl. No. 14/948,924, dated Dec. 31, 2015.

Notice of Allowance issued in U.S. Appl. No. 14/686,457, dated May 11, 2016.

Amendment filed in U.S. Appl. No. 13/792,596 dated May 17, 2016.

Amendment filed in U.S. Appl. No. 14/948,924 dated Jun. 20, 2016.

Office Action issued in U.S. Appl. No. 14/948,924, dated Aug. 8, 2016.

Office Action issued in U.S. Appl. No. 13/792,596, dated Aug. 26, 2016.

Office Action issued in European Patent Application No. 13794418.7 dated Jun. 7, 2017.

Notice of Allowance issued in U.S. Appl. No. 13/792,596 dated May 5, 2017.

SYSTEMS AND METHODS FOR SELECTING, ACTIVATING, OR SELECTING AND ACTIVATING TRANSDUCERS

CROSS-REFERENCE TO RELATED APPLICATIONS

This application is a continuation of U.S. patent application Ser. No. 14/686,408, filed on Apr. 14, 2015, which is a continuation of U.S. patent application Ser. No. 13/792,670, filed on Mar. 11, 2013, now U.S. Pat. No. 9,011,423, issued Apr. 21, 2015, which claims the benefit of each of U.S. Provisional Application No. 61/649,734, filed May 21, 2012; U.S. Provisional Application No. 61/670,881, filed Jul. 12, 2012; and U.S. Provisional Application No. 61/723,311, filed Nov. 6, 2012. The entire disclosure of each of the applications cited in this paragraph is hereby incorporated herein by reference.

TECHNICAL FIELD

Aspects of this disclosure generally are related to systems and methods for selecting, activating, or selecting and activating transducers, such systems and methods applicable to, among other things, medical systems.

BACKGROUND

Cardiac surgery was initially undertaken using highly invasive open procedures. A sternotomy, which is a type of incision in the center of the chest that separates the sternum was typically employed to allow access to the heart. In the past several decades, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

One example of where intravascular or percutaneous medical techniques have been employed is in the treatment of a heart disorder called atrial fibrillation. Atrial fibrillation is a disorder in which spurious electrical signals cause an irregular heartbeat. Atrial fibrillation has been treated with open heart methods using a technique known as the "Cox-Maze procedure". During this procedure, physicians create specific patterns of lesions in the left and right atria to block various paths taken by the spurious electrical signals. Such lesions were originally created using incisions, but are now typically created by ablating the tissue with various techniques including radio-frequency (RF) energy, microwave energy, laser energy and cryogenic techniques. The procedure is performed with a high success rate under the direct vision that is provided in open procedures, but is relatively complex to perform intravascularly or percutaneously because of the difficulty in creating the lesions in the correct locations. Various problems, potentially leading to severe adverse results, may occur if the lesions are placed incorrectly. It is particularly important to know the position of the various transducers which will be creating the lesions relative to cardiac features such as the pulmonary veins and mitral valve. The continuity, transmurality and placement of the lesion patterns that are formed can impact the ability to block paths taken within the heart by spurious electrical signals. Other requirements for various ones of the transducers to perform additional functions such as, but not limited to, mapping various anatomical features, mapping electrophysiological activity, sensing tissue characteristics such as impedance and temperature and tissue stimulation can also complicate the operation of the employed medical device.

In this regard, there is a need for improved intra-bodily-cavity transducer-based device systems or control mechanisms thereof with improved performance and reduced complexity as compared to conventional device systems.

SUMMARY

At least the above-discussed need is addressed and technical solutions are achieved by various embodiments of the present invention. In some embodiments, device systems and methods executed by such systems exhibit enhanced capabilities for the activation of various transducers, which may be located within a bodily cavity, such as an intra-cardiac cavity. In some embodiments, the systems or a portion thereof may be percutaneously or intravascularly delivered to position the various transducers within the bodily cavity. Various ones of the transducers may be activated to distinguish tissue from blood and may be used to deliver positional information of the device relative to various anatomical features in the bodily cavity, such as the pulmonary veins and mitral valve in an atrium. Various ones of the transducers may employ characteristics such as blood flow detection, impedance change detection or deflection force detection to discriminate between blood and tissue. Various ones of the transducers may be used to treat tissue within a bodily cavity. Treatment may include tissue ablation by way of non-limiting example. Various ones of the transducers may be used to stimulate tissue within the bodily cavity. Stimulation can include pacing by way of non-limiting example. Other advantages will become apparent from the teaching herein to those of skill in the art.

In some embodiments, a transducer-activation system may be summarized as including a data processing device system, an input-output device system communicatively connected to the data processing device system, and a memory device system communicatively connected to the data processing device system and storing a program executable by the data processing device system. The program includes display instructions configured to cause the input-output device system to display a graphical representation of at least a portion of a transducer-based device, at least part of the transducer-based device positionable within a bodily cavity. The graphical representation includes a first transducer graphical element, a second transducer graphical element, and a between graphical element. The first transducer graphical element is associated with a first transducer of the transducer-based device. The second transducer graphical element is associated with a second transducer of the transducer-based device different than and spaced apart from the first transducer. The between graphical element is associated with a region of space between the first transducer and the second transducer of the transducer-based device, the region of space not including any transducer. The program further includes selection instructions configured to cause reception of a selection from the input-output device system of the between graphical element and activation instructions configured to, in response to receiving the selection, cause activation of the first transducer and the second transducer via the input-output device system. In various ones of these embodiments, the region of space is not associated with any physical part of the transducer-based device.

The program may further include instructions configured to, in response to receiving the selection, cause the input-output device system to change a visual characteristic of the between graphical element. The graphical representation may include a first spatial relationship between the first transducer graphical element and the second transducer graphical element that is consistent with a second spatial relationship between the corresponding first transducer and the second transducer of the transducer-based device.

The between graphical element may be a first between graphical element and the graphical representation may further include a second between graphical element associated with a region of space between a pair of transducers of the transducer-based device that is associated with a physical part of the transducer-based device. The program may further include instructions configured to cause reception of a selection from the input-output device system of the second between graphical element, and instructions configured to, in response to receiving the selection of the second between graphical element, cause activation of the pair of transducers via the input-output device system. The program may further include instructions configured to, in response to receiving the selection of the second between graphical element, cause the input-output device system to change a visual characteristic of the second between graphical element. The display instructions may include instructions configured to display the second transducer graphical element in a first direction from the first transducer graphical element. The first between graphical element may be between the second transducer graphical element and the first transducer graphical element in the graphical representation and the second between graphical element may be between the second transducer graphical element and a third transducer graphical element in the graphical representation. The display instructions may include instructions for displaying the third transducer graphical element in a second direction from the second transducer graphical element. The first direction and the second direction may be non-parallel to each other. The first between graphical element may be formed, at least in part, at a location in the graphical representation intersected by the first direction from the first transducer graphical element and the second between graphical element may be formed, at least in part, at a location in the graphical representation intersected by the second direction from the second transducer graphical element. The first between graphical element may include an elongate portion extending along the first direction and the second between graphical element may include an elongate portion extending along the second direction. The first direction and the second direction may be oblique to each other. The first direction and the second direction may form an acute angle with each other.

The program may further include instructions configured to, in response to receiving the selection of the between graphical element, cause the input-output device system to change a visual characteristic of the first transducer graphical element, the second transducer graphical element, or both the first transducer graphical element and the second transducer graphical element. In some embodiments, the selection may not include any user-selected transducer graphical element.

The input-output device system may include the transducer-based device. The transducer-based device may be a catheter device. The bodily cavity may be an intra-cardiac cavity. The catheter device may include a structure that includes a plurality of elongate members, each elongate member of the plurality of elongate members including a proximal end, a distal end, and an intermediate portion positioned between the proximal and the distal ends. The structure may be selectively moveable between a delivery configuration in which the structure is sized to be percutaneously delivered to the bodily cavity and a deployed configuration in which the structure has a size too large to be percutaneously delivered to the bodily cavity, the first and the second transducers located on different ones of the plurality of elongate members. The respective intermediate portion of each elongate member of the plurality of elongate members may include a thickness, a front surface, and a back surface opposite across the thickness from the front surface, and the respective intermediate portions of the plurality of elongate members may be arranged front surface-toward-back surface in a stacked array when the structure is in the delivery configuration. The structure may further include a proximal portion and a distal portion, each of the proximal and the distal portions including a respective part of each of the plurality of elongate members, the proximal portion of the structure forming a first domed shape and the distal portion of the structure forming a second domed shape when the structure is in the deployed configuration.

The catheter device may include a structure that includes a proximal portion and a distal portion. The structure may be selectively moveable between a delivery configuration in which the structure is sized for percutaneous delivery to the bodily cavity, the structure arranged to be advanced distal portion first into the bodily cavity and a deployed configuration in which the structure is sized too large to be delivered percutaneously to the bodily cavity. The proximal portion of the structure may form a first domed shape and the distal portion of the structure may form a second domed shape when the structure is in the deployed configuration with the proximal and the distal portions of the structure arranged in a clam shell configuration when the structure is in the deployed configuration.

The transducer-based device may include a structure that includes a plurality of elongate members. The between graphical element may be a first between graphical element and the graphical representation may further include a third transducer graphical element and a second between graphical element, the third transducer graphical element associated with a third transducer of the transducer-based device and the second between graphical element associated with a region of space between the second transducer and the third transducer, the region of space between the second transducer and the third transducer not including any transducer. The second transducer and the third transducer may be located on a same elongate member of the plurality of elongate members and the first transducer and the second transducer may be located on different elongate members of the plurality of elongate members.

The input-output device system may include an energy source device system connected to the first transducer and the second transducer. The activation instructions may be further configured to cause energy from the energy source device system to be delivered to the first transducer and the second transducer in a manner that: (a) a portion of the energy delivered to the first transducer is transmitted by the first transducer, (b) a portion of the energy delivered to the second transducer is transmitted by the second transducer, or both (a) and (b). The activation instructions may be further configured to cause energy from the energy source device system to be delivered to the first transducer and the second transducer in a manner that, (a) a portion of the energy delivered to the first transducer is transmitted by the first transducer to the second transducer, or (b) a portion of the energy delivered to the second transducer is transmitted by the second transducer to the first transducer, or both (a) and (b). The activation instructions may be further configured to cause energy from the energy source device system to be delivered to the first transducer and the second transducer, the energy sufficient to cause ablation of tissue in the bodily cavity. The activation instructions may be further configured to cause a portion of the energy delivered to the first transducer and the second transducer to be delivered between the first transducer and the second transducer across at least part of the region of space. The energy may be sufficient to cause bipolar ablation of the tissue in the bodily cavity. The first transducer may be adjacently spaced from the second transducer along a physical path extending between the first transducer and the second transducer over at least part of an opening in a surface structure of the catheter device, and the energy may be sufficient to ablate a portion of the tissue extending along the physical path.

The between graphical element may be a first between graphical element of a group of between graphical elements included in the graphical representation, each between graphical element of the group of between graphical elements associated with a respective region of space between transducers of the transducer-based device that does not include any transducer and is not associated with any physical part of the transducer-based device. The program may further include determination instructions configured to cause determination, via input received from the input-output device system, of which of a plurality of regions of space, respectively between corresponding transducers of the transducer-based device and respectively not associated with any physical part of the transducer-based device, are and which are not acceptable for activation of the respectively corresponding transducers. The display instructions may be further configured to cause the input-output device system to display the between graphical elements associated with the regions of space determined, according to the determination instructions, to be acceptable for activation of the respectively corresponding transducers with different visual characteristics than visual characteristics of the between graphical elements associated with the regions of space determined, according to the determination instructions, to be not acceptable for activation of the respectively corresponding transducers.

The between graphical element may be a first between graphical element of a plurality of between graphical elements included in the graphical representation, each between graphical element of a first subset of the plurality of between graphical elements associated with a respective region of space between transducers of the transducer-based device that does not include any transducer and that is not associated with any physical part of the transducer-based device, and each between graphical element of a second subset of the plurality of between graphical elements associated with a respective region of space between transducers of the transducer-based device that does not include any transducer and that is associated with a physical part of the transducer-based device. The program may further include determination instructions configured to cause determination, via input received from the input-output device system, of which of a plurality of regions of space, respectively between corresponding transducers of the transducer-based device, are and which are not acceptable for activation of the respectively corresponding transducers. The display instructions may be further configured to cause the input-output device system to display the between graphical elements associated with the regions of space determined, according to the determination instructions, to be acceptable for activation of the respectively corresponding transducers with different visual characteristics than visual characteristics of the between graphical elements associated with the regions of space determined, according to the determination instructions, to be not acceptable for activation of the respectively corresponding transducers.

The transducer-based device may be a catheter device and the input-output device system may include an energy source device system connected to the transducers of the catheter device. The activation instructions may be further configured to cause energy from the energy source device system to be delivered to each of the transducers associated with the regions of space determined, according to the determination instructions, to be acceptable for activation of the respectively corresponding transducers, the energy sufficient to cause ablation of tissue in the bodily cavity. The determination instructions may be further configured to require that, in order for a between graphical element to be determined to be associated with a region of space acceptable for the activation of the respectively corresponding transducers, the corresponding region of space be determined to be associated with an anatomical feature of the bodily cavity that is acceptable for the ablation of the tissue in the bodily cavity. The activation may include bipolar transducer activation, monopolar transducer activation, or both bipolar transducer activation and monopolar transducer activation. The display instructions may be further configured to cause the input-output device system to display the between graphical elements only for the regions of space determined by the determination instructions, to be acceptable for activation of the respectively corresponding transducers.

Each of the first transducer graphical element and the second transducer graphical element may form part of a plurality of transducer graphical elements included in the graphical representation, each of the transducer graphical elements associated with a respective transducer of a plurality of transducers of the transducer-based device, the plurality of transducers arranged in a spaced apart distribution. The between graphical element may be a first between graphical element of a plurality of between graphical elements included in the graphical representation, each of the between graphical elements associated with a respective region of space between a corresponding pair of the transducers in the spaced apart distribution, each pair of the transducers in the spaced apart distribution having at least one different transducer than another of the other pairs of the transducers in the spaced apart distribution, each respective region of space not including any transducer. The selection instructions may be further configured to cause reception of independent selections from the input-output device system of each of at least two of the plurality of between graphical elements, the corresponding pairs of the transducers in the spaced apart distribution associated with the selected at least two of the plurality of between graphical elements having a same transducer. The activation instructions may be further configured to cause activation, via the input-output device system, of each corresponding pair of the transducers in the spaced apart distribution associated with the selected at least two of the plurality of between graphical elements.

The transducers in the spaced apart distribution associated with the selected at least two of the between graphical elements may be selected transducers. The input-output device system may include an energy source device system connected to at least the selected transducers and the activation instructions may further include instructions configured to cause the energy source device system to deliver energy to the selected transducers. The transducer-based device may be a catheter device and the energy may be sufficient for ablating tissue.

Each pair of transducers associated with the selected at least two of the between graphical elements may be a selected pair of transducers. The transducer-based device may be a catheter device and the bodily cavity may be an intra-cardiac cavity. Each transducer in each selected pair of transducers may be configured to detect electrophysiological activity in the intra-cardiac cavity at a location at least proximate the transducer in the selected pair of transducers, and the activation instructions may be further configured to respectively cause generation of a combined electrogram from each selected pair of transducers based at least on electrophysiological activity data received from the transducers of the selected pair of transducers.

The selected at least two of the plurality of between graphical elements may include the first between graphical element and a second between graphical element, the second between graphical element associated with a region of space between a pair of transducers of the transducer-based device that does not include any transducer and is associated with a physical part of the transducer-based device.

The program may further include instructions configured to cause generation of a combined electrogram from both the first transducer and the second transducer. The activation instructions may be further configured to cause bipolar activation between the first and the second transducers. The first transducer graphical element may have a different size than the second transducer graphical element, the different sizes corresponding to respectively different sizes of the first transducer and the second transducer.

Various systems may include combinations and subsets of all those summarized above.

In some embodiments, a catheter device system may be summarized as including a catheter device that includes a plurality of transducers and a structure that includes one or more surfaces, at least a portion of the one or more surfaces defining one or more openings in the structure. The plurality of transducers are arranged on the structure in a spaced apart distribution that is positionable within a bodily cavity, the spaced apart distribution including at least a first transducer, a second transducer, and a third transducer. The first transducer is adjacently spaced from the second transducer along a first physical path extending between the second and the first transducers, at least part of the first physical path extending over at least part of an opening of the one or more openings in the structure. The third transducer is adjacently spaced from the second transducer along a second physical path extending between the second and the third transducers over at least part of the one or more surfaces. The second physical path is non-parallel with the first physical path. The catheter device system further includes a data processing device system, an input-output device system that includes the catheter device and is communicatively connected to the data processing device system, a display device system, an energy source device system, and a memory device system communicatively connected to the data processing device system and storing a program. The program is executable by the data processing device system to cause the catheter device system to execute a method of activating at least some of a plurality of transducers of the catheter device. The method may be summarized as including generating an image via the display device system, the image at least depicting a spatial relationship between at least some of the transducers in the spaced apart distribution, the image including a plurality of transducer graphical elements and a plurality of between graphical elements. Each of the transducer graphical elements is associated with a respective one of the at least some of the transducers in the spaced apart distribution. Each of the between graphical elements includes a first end, a second end, and an elongate portion extending between the first and the second ends. A first one of the plurality of between graphical elements is representative of the first physical path and a second one of the plurality of between graphical elements representative of the second physical path, the elongate portions of the first and the second ones of the plurality of between graphical elements depicted extending along non-parallel directions at respective locations at least proximate the respective transducer graphical element associated with the second transducer. The method further includes processing one or more operations of the input-output device system according to a selection mode configured to allow a selection of at least the first one of the plurality of between graphical elements, and processing one or more operations of the input-output device system according to an activation mode configured to activate a pair of the transducers in the spaced apart distribution in response to the selection of the first one of the plurality of between graphical elements to cause energy provided by the energy source device system to be delivered to the pair of the transducers in the spaced apart distribution, the energy sufficient for ablating tissue along the first physical path represented by the first one of the plurality of between graphical elements in the selection.

The elongate portions of the first and the second ones of the plurality of between graphical elements may be depicted extending obliquely with respect to one another at the respective locations at least proximate the respective transducer graphical element associated with the second transducer. The elongate portions of the first and the second ones of the plurality of between graphical elements may be depicted extending with respect to one another to define an acute angle therebetween.

The method may include causing the input-output device system to vary a visual characteristic of at least the first one of the plurality of between graphical elements in response to the selection of the first one of the plurality of between graphical elements. The method may further include causing the input-output device system to vary a visual characteristic of at least one of the respective transducer graphical elements associated with the first transducer and the second transducer in response to the selection of the first one of the plurality of between graphical elements. In some embodiments, the selection may not include any user-selected transducer graphical element.

The structure may include a plurality of elongate members, each elongate member of the plurality of elongate members including a proximal end, a distal end and an intermediate portion positioned between the proximal and distal ends. The structure may be selectively moveable between a delivery configuration in which the structure is sized to be percutaneously delivered to the bodily cavity and a deployed configuration in which the structure has a size too large to be percutaneously delivered to the bodily cavity, the plurality of transducers located on at least some of the plurality of elongate members. Each of the first transducer and the second transducer may be located on a different elongate member of the at least some of the plurality of elongate members and each of the second transducer and the third transducer may be located on a same elongate member of the at least some of the plurality of elongate members. The respective intermediate portion of each elongate member of the plurality of elongate members may include a thickness, a front surface and a back surface opposite across the thickness from the front surface, and the respective intermediate portions of the plurality of elongate members may be arranged front surface-toward-back surface in a stacked array when the structure is in the delivery configuration. The structure may include a proximal portion and a distal portion, each of the proximal and the distal portions including a respective part of each of the plurality of elongate members, the proximal portion of the structure forming a first domed shape and the distal portion of the structure forming a second domed shape when the structure is in the deployed configuration.

A portion of the energy delivered to the pair of the transducers in the spaced apart distribution may be delivered between the transducers of the pair of the transducers in the spaced apart distribution.

Various methods may include combinations and subsets of all those summarized above.

In some embodiments, a transducer-activation system may be summarized as including a data processing device system, an input-output device system communicatively connected to the data processing device system, and a memory device system communicatively connected to the data processing device system and storing a program executable by the data processing device system. The data processing device system is configured by the program at least to cause the input-output device system to display a graphical representation of at least a portion of a transducer-based device, at least part of the transducer-based device positionable within a bodily cavity, and the graphical representation including a first transducer graphical element, a second transducer graphical element, and a between graphical element. The first transducer graphical element is associated with a first transducer of the transducer-based device, the second transducer graphical element is associated with a second transducer of the transducer-based device different than and spaced apart from the first transducer, and the between graphical element associated with a region of space between the first transducer and the second transducer of the transducer-based device, the region of space not including any transducer. The data processing device system is further configured by the program at least to receive a selection from the input-output device system of the between graphical element, and cause activation, in response to receiving the selection, of the first transducer and the second transducer via the input-output device system. The region of space may not be associated with any physical part of the transducer-based device. In some embodiments, the selection may not include any user-selected transducer graphical element.

In some embodiments, a memory device system is communicatively connected to a data processing device system, and the data processing device system is further communicatively connected to an input-output device system. A transducer-activation method executed by a data processing device system according to a program stored by the memory device system may be summarized as including causing the input-output device system to display a graphical representation of at least a portion of a transducer-based device, at least part of the transducer-based device positionable within a bodily cavity. The graphical representation includes a first transducer graphical element, a second transducer graphical element, and a between graphical element, the first transducer graphical element associated with a first transducer of the transducer-based device, the second transducer graphical element associated with a second transducer of the transducer-based device different than and spaced apart from the first transducer, and the between graphical element associated with a region of space between the first transducer and the second transducer of the transducer-based device, the region of space not including any transducer. The method further includes receiving a selection from the input-output device system of the between graphical element, and causing activation, in response to receiving the selection, of the first transducer and the second transducer via the input-output device system. The region of space may not be associated with any physical part of the transducer-based device. In some embodiments, the selection may not include any user-selected transducer graphical element.

In some embodiments, a computer-readable storage medium system may be summarized as including one or more computer-readable storage mediums storing a program executable by one or more data processing devices of a data processing device system communicatively connected to an input-output device system. The program includes a display module configured to cause the input-output device system to display a graphical representation of at least a portion of a transducer-based device, at least part of the transducer-based device positionable within a bodily cavity. The graphical representation includes a first transducer graphical element, a second transducer graphical element, and a between graphical element, the first transducer graphical element associated with a first transducer of the transducer-based device, the second transducer graphical element associated with a second transducer of the transducer-based device different than and spaced apart from the first transducer, and the between graphical element associated with a region of space between the first transducer and the second transducer of the transducer-based device, the region of space not including any transducer. The program further includes a selection module configured to cause reception of a selection from the input-output device system of the between graphical element, and an activation module configured to, in response to receiving the selection, cause activation of the first transducer and the second transducer via the input-output device system. The region of space may not be associated with any physical part of the transducer-based device. In some embodiments, the selection may not include any user-selected transducer graphical element. In some embodiments, the computer-readable storage medium system is a non-transitory computer-readable storage medium system including one or more non-transitory computer-readable storage mediums storing the program.

In some embodiments, a transducer-activation system may be summarized as including a data processing device system, an input-output device system communicatively connected to the data processing device system, and a memory device system communicatively connected to the data processing device system and storing a program executable by the data processing device system. The program includes graphical interface instructions configured to cause the input-output device system to display a graphical interface including a graphical representation of at least some of a plurality of graphical elements, each of the plurality of graphical elements respectively associated with a respective one of a plurality of transducer sets, each respective transducer set including at least one of a plurality of transducers included as part of a transducer-based device, and each respective transducer set having at least one different transducer than another of the other transducer sets. The program includes input instructions configured to cause reception of transducer data via the input-output device system, the transducer data indicating data acquired by the plurality of transducers. The program includes identification instructions configured to cause identification of ablation-ready transducers of the plurality of transducers as transducers that are adjacent a region of space deemed, based at least on an analysis of the transducer data, acceptable for ablation, and not-ablation-ready transducers of the plurality of transducers as transducers that are adjacent a region of space deemed, based at least on the analysis of the transducer data, not acceptable for ablation. The graphical interface includes a first set of visual characteristics associated with the graphical elements that are associated with each of the transducers sets that include the ablation-ready transducers, and includes a second set of visual characteristics associated with the graphical elements that are associated with the transducer sets that include the not-ablation-ready transducers, the first set of visual characteristics being different than the second set of visual characteristics. The program includes ablation request instructions configured to cause reception of an ablation request from the input-output device system, the ablation request configured to request ablation by at least some of the plurality of transducers. The program further includes activation instructions configured to, in response to receiving the ablation request from the input-output device system, cause energy from an energy source device system to be delivered to each of the plurality of ablation-ready transducers in the at least some of the plurality of transducers, and non-activation instructions configured to cause prevention of delivery of energy from the energy source device system to each of the plurality of not-ablation-ready transducers.

The ablation request instructions may be configured to cause reception of a selection from the input-output device system of the graphical elements associated with the respective transducer sets including the at least some of the plurality of transducers.

Each transducer set may include a single transducer of the plurality of transducers. Each transducer set may include at least a pair of the plurality of transducers. The plurality of transducers may be arranged in a distribution, the plurality of transducers positionable within a bodily cavity, and each pair of the plurality of transducers may be a pair of adjacent transducers in the distribution. Each of the transducers in the distribution may be spaced apart from each of the other transducers in the distribution. The first set of visual characteristics may be associated only with the graphical elements that are associated with the transducer sets each consisting of transducers identified by the identification instructions as only being ablation-ready transducers. The second set of visual characteristics may be associated only with the graphical elements that are associated with the transducer sets each having at least one transducer identified by the identification instructions as being a not-ablation-ready transducer. The graphical interface instructions may be further configured to cause the input-output device system to display only the graphical elements associated with transducer sets consisting of transducers identified by the identification instructions as only being ablation-ready transducers.

The at least some of the plurality of transducers may be an ablation-requested transducer set. The program may further include determination instructions configured to cause determination of whether the ablation-requested transducer set includes a not-ablation-ready transducer, and ablation denial instructions configured to, if it is determined according to the determination instructions that the ablation-requested transducer set includes the not-ablation-ready transducer, cause denial of the ablation request, at least with respect to the not-ablation-ready transducer in the ablation-requested transducer set. The program may further include determination instructions configured to cause determination of whether the ablation-requested transducer set includes a not-ablation-ready transducer, and ablation denial instructions configured to cause denial of the ablation request if it is determined according to the determination instructions that the ablation-requested transducer set includes the not-ablation-ready transducer.

The input-output device system may include the transducer-based device. The transducer-based device may be a catheter device with a portion thereof sized to be positionable within a bodily cavity. The bodily cavity may be an intra-cardiac cavity. The catheter device may include a structure that includes a plurality of elongate members, each elongate member of the plurality of elongate members including a proximal end, a distal end and an intermediate portion positioned between the proximal and the distal ends. The structure may be selectively moveable between a delivery configuration in which the structure is sized to be percutaneously delivered to the bodily cavity and a deployed configuration in which the structure has a size too large to be percutaneously delivered to the bodily cavity, the plurality of transducers located on at least some of the plurality of elongate members. At least one of the transducer sets may include at least two transducers identified by the identification instructions as being not-ablation-ready transducers, the at least two transducers located on different elongate members of the at least some of the plurality of elongate members. The respective intermediate portion of each elongate member of the plurality of elongate members may include a thickness, a front surface, and a back surface opposite across the thickness from the front surface, and the respective intermediate portions of the plurality of elongate members may be arranged front surface-toward-back surface in a stacked array when the structure is in the delivery configuration. The structure may further include a proximal portion and a distal portion, each of the proximal and the distal portions including a respective part of each of the plurality of elongate members, the proximal portion of the structure forming a first domed shape and the distal portion of the structure forming a second domed shape when the structure is in the deployed configuration.

The catheter device may include a structure that includes a proximal portion and a distal portion. The structure may be selectively moveable between a delivery configuration in which the structure is sized for percutaneous delivery to the bodily cavity, the structure arranged to be advanced distal portion first into the bodily cavity, and a deployed configuration in which the structure is sized too large to be delivered percutaneously to the bodily cavity. The proximal portion of the structure may form a first domed shape and the distal portion of the structure may form a second domed shape when the structure is in the deployed configuration, the proximal and the distal portions of the structure arranged in a clam shell configuration when the structure is in the deployed configuration.

The plurality of transducers may be arranged in a distribution, the plurality of transducers positionable within a bodily cavity. The transducer data may include data associated with an electrical characteristic of tissue in the bodily cavity. The electrical characteristic may be an electrical impedance of the tissue in the bodily cavity. The transducer data may include data associated with a flow characteristic of fluid in the bodily cavity.

The plurality of transducers may be arranged in a distribution, the plurality of transducers positionable within a bodily cavity. The identification instructions may include instructions configured to cause a requirement that, in order for a region of space to be deemed acceptable for ablation, the region of space be determined, based at least on the analysis of the transducer data, to be associated with a tissue in the bodily cavity that is acceptable for ablation, and the identification instructions may further include instructions configured to cause a requirement that, in order for a region of space to be deemed not acceptable for ablation, the region of space be determined, based at least on the analysis of the transducer data, to be associated with a tissue in the bodily cavity that is not acceptable for ablation. The bodily cavity may be an intra-cardiac cavity and the tissue in the bodily cavity that is not acceptable for ablation may be blood. The identification instructions may include instructions configured to cause a requirement that, in order for a region of space to be deemed acceptable for ablation, the region of space be determined, based at least on the analysis of the transducer data, to be associated with an anatomical feature of the bodily cavity that is acceptable for ablation, and the identification instructions may further include instructions configured to cause a requirement that, in order for a region of space to be deemed not acceptable for ablation, the region of space be determined, based at least on the analysis of the transducer data, to be associated with an anatomical feature of the bodily cavity that is not acceptable for ablation. The plurality of transducers may be arranged in a distribution, the plurality of transducers positionable within a bodily cavity that includes a tissue wall surface interrupted by one or more ports in fluid communication with the bodily cavity. The identification instructions may include instructions configured to cause a requirement that, in order for a region of space to be deemed not acceptable for ablation, the region of space be determined, based at least on the analysis of the transducer data, to overlie at least part of a port of the one or more ports.

Each respective transducer set may have at least one different transducer than each of the other transducer sets.

Various systems may include combinations and subsets of all those summarized above.

In some embodiments, a transducer-activation system may be summarized as including a data processing device system, an input-output device system communicatively connected to the data processing device system, and a memory device system communicatively connected to the data processing device system and storing a program executable by the data processing device system. The data processing device system is configured by the program at least to cause the input-output device system to display a graphical interface including a graphical representation of at least some of a plurality of graphical elements, each of the plurality of graphical elements respectively associated with a respective one of a plurality of transducer sets. Each respective transducer set includes at least one of a plurality of transducers included as part of a transducer-based device, and each respective transducer set has at least one different transducer than another of the other transducer sets. The data processing device system is configured by the program at least to receive transducer data via the input-output device system, the transducer data indicating data acquired by the plurality of transducers. The data processing device system is configured by the program at least to identify ablation-ready transducers of the plurality of transducers as transducers that are adjacent a region of space deemed, based at least on an analysis of the transducer data, acceptable for ablation, and not-ablation-ready transducers of the plurality of transducers as transducers that are adjacent a region of space deemed, based at least on the analysis of the transducer data, not acceptable for ablation. The graphical interface includes a first set of visual characteristics associated with the graphical elements that are associated with each of the transducers sets that include the ablation-ready transducers, and includes a second set of visual characteristics associated with the graphical elements that are associated with the transducer sets that include the not-ablation-ready transducers, the first set of visual characteristics being different than the second set of visual characteristics. The data processing device system is configured by the program at least to receive an ablation request from the input-output device system, the ablation request configured to request ablation by at least some of the plurality of transducers. The data processing device system is configured by the program at least to cause, in response to receiving the ablation request from the input-output device system, energy from an energy source device system to be delivered to each of the plurality of ablation-ready transducers in the at least some of the plurality of transducers, and prevent delivery of energy from the energy source device system to each of the plurality of not-ablation-ready transducers.

In some embodiments, a memory device system is communicatively connected to a data processing device system, the data processing device system further communicatively connected to an input-output device system. A transducer-activation method executed by the data processing device system according to a program stored by the memory device system may be summarized as including causing the input-output device system to display a graphical interface including a graphical representation of at least some of a plurality of graphical elements, each of the plurality of graphical elements respectively associated with a respective one of a plurality of transducer sets, each respective transducer set including at least one of a plurality of transducers included as part of a transducer-based device, and each respective transducer set having at least one different transducer than another of the other transducer sets. The transducer-activation method includes receiving transducer data via the input-output device system, the transducer data indicating data acquired by the plurality of transducers. The transducer-activation method includes identifying ablation-ready transducers of the plurality of transducers as transducers that are adjacent a region of space deemed, based at least on an analysis of the transducer data, acceptable for ablation, and not-ablation-ready transducers of the plurality of transducers as transducers that are adjacent a region of space deemed, based at least on the analysis of the transducer data, not acceptable for ablation. The graphical interface includes a first set of visual characteristics associated with the graphical elements that are associated with each of the transducers sets that includes the ablation-ready transducers, and includes a second set of visual characteristics associated with the graphical elements that are associated with the transducer sets that includes the not-ablation-ready transducers, the first set of visual characteristics being different than the second set of visual characteristics. The transducer-activation method includes receiving an ablation request from the input-output device system, the ablation request configured to request ablation by at least some of the plurality of transducers. The transducer-activation method further includes causing, in response to receiving the ablation request from the input-output device system, energy from an energy source device system to be delivered to each of the plurality of ablation-ready transducers in the at least some of the plurality of transducers, and preventing delivery of energy from the energy source device system to each of the plurality of not-ablation-ready transducers.

In some embodiments, a computer-readable storage medium system may be summarized as including one or more computer-readable storage mediums storing a program executable by one or more data processing devices of a data processing device system communicatively connected to an input-output device system. The program includes a graphical interface module configured to cause the input-output device system to display a graphical interface including a graphical representation of at least some of a plurality of graphical elements, each of the plurality of graphical elements respectively associated with a respective one of a plurality of transducer sets, each respective transducer set including at least one of a plurality of transducers included as part of a transducer-based device, and each respective transducer set having at least one different transducer than another of the other transducer sets. The program includes an input module configured to cause reception of transducer data via the input-output device system, the transducer data indicating data acquired by the plurality of transducers. The program includes an identification module configured to cause identification of ablation-ready transducers of the plurality of transducers as transducers that are adjacent a region of space deemed, based at least on an analysis of the transducer data, acceptable for ablation, and not-ablation-ready transducers of the plurality of transducers as transducers that are adjacent a region of space deemed, based at least on the analysis of the transducer data, not acceptable for ablation. The graphical interface includes a first set of visual characteristics associated with the graphical elements that are associated with each of the transducers sets that includes the ablation-ready transducers, and includes a second set of visual characteristics associated with the graphical elements that are associated with the transducer sets that includes the not-ablation-ready transducers, the first set of visual characteristics being different than the second set of visual characteristics. The program includes an ablation request module configured to cause reception of an ablation request from the input-output device system, the ablation request configured to request ablation by at least some of the plurality of transducers. The program further includes an activation module configured to, in response to receiving the ablation request from the input-output device system, cause energy from an energy source device system to be delivered to each of the plurality of ablation-ready transducers in the at least some of the plurality of transducers, and a non-activation module configured to cause prevention of delivery of energy from the energy source device system to each of the plurality of not-ablation-ready transducers. In some embodiments, the computer-readable storage medium system is a non-transitory computer-readable storage medium system including one or more non-transitory computer-readable storage mediums storing the program.

In some embodiments, a transducer-based device system may be summarized as including a data processing device system. The transducer-based device includes an input-output device system communicatively connected to the data processing device system. The input-output device system includes a transducer-based device, at least part of the transducer-based device positionable within a bodily cavity, and the transducer-based device including a structure that positions a plurality of transducers in a spaced apart distribution. The transducer-based device further includes a memory device system communicatively connected to the data processing device system and storing a program executable by the data processing device system. The program includes graphical representation instructions configured to cause the input-output device system to display a graphical representation of at least a portion of the transducer-based device. The graphical representation includes a plurality of transducer graphical elements and a plurality of between graphical elements. Each of the transducer graphical elements is associated with a respective transducer of the plurality of transducers of the transducer-based device, and each of the between graphical elements is associated with a region of space between a pair of the transducers in the spaced apart distribution, each region of space not including any transducer, and no two of the pairs of the transducers having an identical pair of the transducers. The plurality of transducer graphical elements and at least a portion of the plurality of between graphical elements are arranged in a plurality of rows and a plurality of columns. The transducer graphical elements and the between graphical elements in each respective one of the plurality of rows are interleaved with respect to one another along the respective one of the plurality of rows. The transducer graphical elements and the between graphical elements in each respective one of the plurality of columns are interleaved with respect to one another along the respective one of the plurality of columns. Each one of the plurality of columns shares a same transducer graphical element with one of the plurality of rows. The program further includes selection instructions configured to cause reception of independent selections from the input-output device system of each of at least two of the plurality of between graphical elements, and path-display instructions configured to, in response to receiving the independent selections, cause the graphical representation to include, during a time interval that occurs (a) during the receiving of the independent selections, (b) after a completion of the receiving of the independent selections, or both (a) and (b), a displayed visual representation of a path passing through at least a portion of each of the selected between graphical elements, the displayed visual representation of the path extending between at least two of the plurality of rows and between at least two of the plurality of columns.

The path-display instructions may be further configured to cause the displayed visual representation of the path to pass through at least some of the transducer graphical elements associated with the transducers in the pairs of transducers between which the regions of space associated with the selected between graphical elements respectively reside.

Each respective one of the plurality of columns may exclude any of the between graphical elements included in each of the plurality of rows. The displayed visual representation of the path may include a path segment that proceeds diagonally between a first node located at a first junction of a first one of the plurality of columns and a first one of the plurality of rows and a second node located at a second junction of a second one of the plurality of columns and a second one of the plurality of rows, the first junction being different than the second junction. The path-display instructions may include instructions configured to cause the displayed graphical representation to change a visual characteristic of the selected between graphical elements as at least part of forming the displayed visual representation of the path. The path-display instructions may include instructions configured to, in response to receiving the independent selections, cause the displayed graphical representation to change, during the time interval, a visual characteristic of the at least some of the transducer graphical elements associated with the transducers in the pairs of the transducers between which the regions of space associated with the selected between graphical elements respectively reside.

The graphical representation may be three-dimensional. The plurality of rows and the plurality of columns may be depicted as a three-dimensional arrangement in the graphical representation. At least two of the plurality of columns may be depicted in the graphical representation extending along respective directions that converge with respect to one another. At least two of the plurality of columns may be depicted in the graphical representation extending along non-parallel directions. At least two of the plurality of rows may be depicted in the graphical representation extending along parallel directions. The plurality of rows and the plurality of columns may be depicted in the graphical representation in an arrangement in which the columns are circumferentially arranged. The plurality of rows and the plurality of columns may be depicted in the graphical representation in an arrangement having a generally spherical shape.

At least a first one of the plurality of between graphical elements may be depicted in the graphical representation positioned between two adjacent ones of the plurality of rows, and at least a second one of the plurality of between graphical elements may be depicted in the graphical representation positioned between two adjacent ones of the plurality of columns. Each of at least some of the plurality of between graphical elements may include a first end, a second end and an elongate portion extending between the first end and the second end. Each of the first end and the second end of each of the at least some of the plurality of between graphical elements may connect to a transducer graphical element in the graphical representation. The elongate portions of at least two of the at least some of the plurality of between graphical elements may extend along respective directions defining an acute angle therebetween.

The program may further include activation instructions configured to, in response to receiving the independent selections, cause activation, via the input-output device system, of the transducers in the pairs of the transducers between which the regions of space associated with the selected between graphical elements respectively reside. The input-output device system may include an energy source device system configured to be connected to the transducers in the pairs of the transducers between which the regions of space associated with the selected between graphical elements respectively reside, the activation instructions configured to cause the activation to occur during the time interval. The activation instructions may include instructions configured to, in response to receiving the independent selections, cause the energy source device system to deliver energy to the transducers in the pairs of the transducers between which the regions of space associated with the selected between graphical elements respectively reside, the energy sufficient for ablating tissue, and the activation instructions configured to cause the energy to be delivered during the time interval. The input-output device system may include an indifferent electrode configured to receive a portion of the energy delivered to at least one of the transducers in the pairs of the transducers between which the regions of space associated with the selected between graphical elements respectively reside. The activation instructions may include instructions configured to, in response to receiving the independent selections, cause the energy source device system to deliver energy to the transducers in the pairs of the transducers between which the regions of space associated with the selected between graphical elements respectively reside, the energy to be delivered in a manner that (d) a portion of the energy delivered to a first transducer of each pair of the transducers is transmitted by the first transducer, (e) a portion of the energy delivered to a second transducer of each pair of the transducers is transmitted by the second transducer, or both (d) and (e), and the activation instructions configured to cause the energy to be delivered during the time interval. The transducer-based device may be a catheter device and the bodily cavity may be an intra-cardiac cavity. One of the pairs of the transducers between which one of the regions of space associated with one of the selected between graphical elements resides includes a first transducer and a second transducer and each of the first transducer and the second transducer may be configured to detect electrophysiological activity in the intra-cardiac cavity at a location at least proximate the respective transducer. The activation instructions may include instructions configured to, in response to receiving the independent selection of the one of the selected between graphical elements, cause generation of a combined electrogram based upon electrophysiological activity data received from the first transducer and the second transducer.

At least one of the regions of space associated with the between graphical elements may not be associated with any physical part of the transducer-based device. At least one of the regions of space associated with the between graphical elements may be associated with a physical part of the transducer-based device. The structure may include one or more surfaces, at least a portion of the one or more surfaces defining one or more openings in the structure. A first particular one of the plurality of between graphical elements may be associated with a region of space between a first particular one of the pairs of the transducers, the first particular one of the pairs of the transducers being spaced with respect to one another over a surface of the one or more surfaces, and a second particular one of the plurality of between graphical elements may be associated with a region of space between a second particular one of the pairs of the transducers, the second particular one of the pairs of the transducers being spaced with respect to one another over at least part of an opening of the one or more openings in the structure.

The transducer-based device may be a catheter device. The structure may include a plurality of elongate members, each elongate member of the plurality of elongate members including a proximal end, a distal end and an intermediate portion positioned between the proximal and the distal ends, the structure selectively moveable between a delivery configuration in which the structure is sized to be percutaneously delivered to the bodily cavity and a deployed configuration in which the structure has a size too large to be percutaneously delivered to the bodily cavity, the plurality of transducers located on at least some of the plurality of elongate members. A first particular one of the plurality of between graphical elements may be associated with a region of space between a first particular one of the pairs of the transducers. A second particular one of the plurality of between graphical elements may be associated with a region of space between a second particular one of the pairs of the transducers. Each transducer in the first particular one of the pairs of the transducers may be located on a same elongate member of the at least some of the plurality of elongate members, and each transducer in the second particular one of the pairs of the transducers may be located on a different elongate member of the at least some of the plurality of elongate members. The respective intermediate portion of each elongate member of the plurality of elongate members may include a thickness, a front surface, and a back surface opposite across the thickness from the front surface, and the respective intermediate portions of the plurality of elongate members may be arranged front surface-toward-back surface in a stacked array when the structure is in the delivery configuration. The structure may include a proximal portion and a distal portion, each of the proximal and the distal portions including a respective part of each of the plurality of elongate members, the proximal portion of the structure forming a first domed shape and the distal portion of the structure forming a second domed shape when the structure is in the deployed configuration.

The structure may include a proximal portion and a distal portion, and the structure may be selectively moveable between a delivery configuration in which the structure is sized for percutaneous delivery to the bodily cavity, the structure arranged to be advanced distal portion first into the bodily cavity, and a deployed configuration in which the structure is sized too large to be delivered percutaneously to the bodily cavity, the proximal portion of the structure forming a first domed shape and the distal portion of the structure forming a second domed shape when the structure is in the deployed configuration, the proximal and the distal portion of the structure arranged in a clam shell configuration when the structure is in the deployed configuration.

Various systems may include combinations and subsets of all those summarized above.

In some embodiments, a transducer-activation system may be summarized as including a data processing device system, an input-output device system communicatively connected to the data processing device system, the input-output device system including a transducer-based device, at least part of the transducer-based device positionable within a bodily cavity, and the transducer-based device including a structure that positions a plurality of transducers in a spaced apart distribution, and a memory device system communicatively connected to the data processing device system and storing a program executable by the data processing device system. The data processing device system is configured by the program at least to cause the input-output device system to display a graphical representation of at least a portion of the transducer-based device, the graphical representation including a plurality of transducer graphical elements and a plurality of between graphical elements. Each of the transducer graphical elements is associated with a respective transducer of the plurality of transducers of the transducer-based device, and each of the between graphical elements is associated with a region of space between a pair of the transducers in the spaced apart distribution, each region of space not including any transducer, and no two of the pairs of the transducers having an identical pair of the transducers. The plurality of transducer graphical elements and at least a portion of the plurality of between graphical elements are arranged in a plurality of rows and a plurality of columns. The transducer graphical elements and the between graphical elements in each respective one of the plurality of rows are interleaved with respect to one another along the respective one of the plurality of rows. The transducer graphical elements and the between graphical elements in each respective one of the plurality of columns are interleaved with respect to one another along the respective one of the plurality of columns. Each one of the plurality of columns shares a same transducer graphical element with one of the plurality of rows. The data processing device system is further configured by the program at least to receive independent selections from the input-output device system of each of at least two of the plurality of between graphical elements, and cause, in response to receiving the independent selections, the graphical representation to include, during a time interval that occurs (a) during the receiving of the independent selections, (b) after a completion of the receiving of the independent selections, or both (a) and (b), a displayed visual representation of a path passing through at least a portion of each of the selected between graphical elements, the displayed visual representation of the path extending between at least two of the plurality of rows and between at least two of the plurality of columns.

In some embodiments, a transducer-activation method is executed by a data processing device system according to a program stored by a memory device system communicatively connected to the data processing device system. The data processing device system is further communicatively connected to an input-output device system. The input-output device system includes a transducer-based device, at least part of the transducer-based device positionable within a bodily cavity, and the transducer-based device includes a structure that positions a plurality of transducers in a spaced apart distribution. The method may be summarized as including causing the input-output device system to display a graphical representation of at least a portion of the transducer-based device, the graphical representation including a plurality of transducer graphical elements and a plurality of between graphical elements. Each of the transducer graphical elements is associated with a respective transducer of the plurality of transducers of the transducer-based device, and each of the between graphical elements is associated with a region of space between a pair of the transducers in the spaced apart distribution, each region of space not including any transducer, and no two of the pairs of the transducers having an identical pair of the transducers. The plurality of transducer graphical elements and at least a portion of the plurality of between graphical elements are arranged in a plurality of rows and a plurality of columns. The transducer graphical elements and the between graphical elements in each respective one of the plurality of rows are interleaved with respect to one another along the respective one of the plurality of rows. The transducer graphical elements and the between graphical elements in each respective one of the plurality of columns are interleaved with respect to one another along the respective one of the plurality of columns. Each one of the plurality of columns shares a same transducer graphical element with one of the plurality of rows. The method further includes receiving independent selections from the input-output device system of each of at least two of the plurality of between graphical elements, and causing, in response to receiving the independent selections, the graphical representation to include, during a time interval that occurs (a) during the receiving of the independent selections, (b) after a completion of the receiving of the independent selections, or both (a) and (b), a displayed visual representation of a path passing through at least a portion of each of the selected between graphical elements, the displayed visual representation of the path extending between at least two of the plurality of rows and between at least two of the plurality of columns.

In some embodiments, a computer-readable storage medium system may be summarized as including one or more computer-readable storage mediums storing a program executable by one or more data processing devices of a data processing device system communicatively connected to an input-output device system. The input-output device system includes a transducer-based device, at least part of the transducer-based device positionable within a bodily cavity. The transducer-based device includes a structure that positions a plurality of transducers in a spaced apart distribution. The program includes a graphical representation module configured to cause the input-output device system to display a graphical representation of at least a portion of the transducer-based device. The graphical representation includes a plurality of transducer graphical elements and a plurality of between graphical elements. Each of the transducer graphical elements is associated with a respective transducer of the plurality of transducers of the transducer-based device, and each of the between graphical elements is associated with a region of space between a pair of the transducers in the spaced apart distribution, each region of space not including any transducer, and no two of the pairs of the transducers having an identical pair of the transducers. The plurality of transducer graphical elements and at least a portion of the plurality of between graphical elements are arranged in a plurality of rows and a plurality of columns. The transducer graphical elements and the between graphical elements in each respective one of the plurality of rows are interleaved with respect to one another along the respective one of the plurality of rows. The transducer graphical elements and the between graphical elements in each respective one of the plurality of columns are interleaved with respect to one another along the respective one of the plurality of columns. Each one of the plurality of columns shares a same transducer graphical element with one of the plurality of rows. The program further includes a selection module configured to cause reception of independent selections from the input-output device system of each of at least two of the plurality of between graphical elements, and a path-display module configured to, in response to receiving the independent selections, cause the graphical representation to include, during a time interval that occurs (a) during the receiving of the independent selections, (b) after a completion of the receiving of the independent selections, or both (a) and (b), a displayed visual representation of a path passing through at least a portion of each of the selected between graphical elements, the displayed visual representation of the path extending between at least two of the plurality of rows and between at least two of the plurality of columns. In some embodiments, the computer-readable storage medium system is a non-transitory computer-readable storage medium system including one or more non-transitory computer-readable storage mediums storing the program.

In some embodiments, a transducer-selection system may be summarized as including a data processing device system, an input-output device system communicatively connected to the data processing device system, and a memory device system communicatively connected to the data processing device system and storing a program executable by the data processing device system. The program includes input instructions configured to cause reception of transducer data via the input-output device system, the transducer data indicating data acquired by at least some of a plurality of transducers included in a transducer-based device, at least part of the transducer-based device positionable within a bodily cavity. The program includes graphical representation instructions configured to cause the input-output device system to display a graphical representation, the graphical representation including a plurality of transducer graphical elements respectively associated with the plurality of transducers of the transducer-based device. The program includes identification instructions configured to cause identification of a region of the graphical representation that corresponds to at least a portion of an anatomical feature based at least on an analysis of the transducer data, wherein the graphical representation instructions are configured to cause the input-output device system to visually display the identified region of the graphical representation. The program further includes selection instructions configured to cause reception of a selection from the input-output device system of the visually-displayed identified region, and path-display instructions configured to, in response to receiving the selection, cause the displayed graphical representation to include a displayed visual representation of an ablation path configured for the anatomical feature.

The displayed visual representation of the ablation path may surround the identified region in the graphical representation. The displayed visual representation of the ablation path may continuously surround the identified region in the graphical representation. The transducer-based device may be a catheter device, and the anatomical feature may be an anatomical feature that forms at least part of the bodily cavity. The bodily cavity may include a tissue wall surface interrupted by one or more ports in fluid communication with the bodily cavity, and the anatomical feature may include at least one port of the one or more ports.

The plurality of transducers may be arranged in a distribution, the plurality of transducers positionable within a bodily cavity. The transducer data may include data associated with an electrical characteristic of tissue in the bodily cavity. The electrical characteristic may be an electrical impedance of the tissue in the bodily cavity. The transducer data may include data associated with a flow characteristic of fluid in the bodily cavity.

The displayed visual representation of the ablation path may pass through a number of locations in the graphical representation, each of the number of locations positioned in the graphical representation at least proximate a respective one of at least some of the plurality of transducer graphical elements. The graphical representation instructions may include instructions configured to, in response to receiving the selection, cause the input-output device system to vary a visual characteristic of each of the at least some of the plurality of transducer graphical elements. The program may further include path-acceptance instructions configured to cause the data processing device system to receive an acceptance of the visual representation of the ablation path based at least on a user response communicated via the input-output device system. The program may further include activation instructions configured to, in response to receiving the acceptance, cause energy from an energy source device system to be delivered to each of the transducers associated with the at least some of the plurality of transducer graphical elements, the energy sufficient for ablating tissue.

The graphical representation may include a plurality of between graphical elements, each between graphical element associated with a region of space between a respective pair of the plurality of transducers, each region of space not including any transducer, and no two of the respective pairs of the plurality of transducers having an identical pair of the transducers. The graphical representation instructions may include instructions configured to, in response to receiving the selection, cause the input-output device system to vary a visual characteristic of each of at least some of the plurality of between graphical elements. The displayed visual representation of the ablation path may pass through each of the at least some of the plurality of between graphical elements. The program may further include path-acceptance instructions configured to cause reception of an acceptance of the visual representation of the ablation path based at least on a user response via the input-output device system, and activation instructions configured to, in response to receiving the acceptance, cause energy from an energy source device system to be delivered to each of the corresponding pairs of the plurality of transducers associated with each of the at least some of the plurality of between graphical elements, the energy sufficient for ablating tissue.

Various systems may include combinations and subsets of all those summarized above.

In some embodiments, a transducer-activation system includes a data processing device system, an input-output device system communicatively connected to the data processing device system, and a memory device system communicatively connected to the data processing device system and storing a program executable by the data processing device system. The data processing device system is configured by the program at least to receive transducer data via the input-output device system, the transducer data indicating data acquired by at least some of a plurality of transducers included in a transducer-based device, at least part of the transducer-based device positionable within a bodily cavity. The data processing device system is configured by the program at least to cause the input-output device system to display a graphical representation, the graphical representation including a plurality of transducer graphical elements respectively associated with the plurality of transducers of the transducer-based device. The data processing device system is configured by the program at least to identify a region of the graphical representation that corresponds to at least a portion of an anatomical feature based at least on an analysis of the transducer data. The data processing device system is configured by the program at least to cause the input-output device system to visually display the identified region of the graphical representation. The data processing device system is configured by the program at least to receive a selection from the input-output device system of the visually-displayed identified region, and cause, in response to receiving the selection, the displayed graphical representation to include a displayed visual representation of an ablation path configured for the anatomical feature.

In some example embodiments a transducer-activation method is executed by a data processing device system according to a program stored by a memory device system communicatively connected to the data processing device system, the data processing device system further communicatively connected to an input-output device system. The method may be summarized as including receiving transducer data via the input-output device system, the transducer data indicating data acquired by at least some of a plurality of transducers included in a transducer-based device, at least part of the transducer-based device positionable within a bodily cavity. The method includes causing the input-output device system to display a graphical representation, the graphical representation including a plurality of transducer graphical elements respectively associated with the plurality of transducers of the transducer-based device. The method includes identifying a region of the graphical representation that corresponds to at least a portion of an anatomical feature based at least on an analysis of the transducer data. The method includes causing the input-output device system to visually display the identified region of the graphical representation. The method further includes receiving a selection from the input-output device system of the visually-displayed identified region, and causing, in response to receiving the selection, the displayed graphical representation to include a displayed visual representation of an ablation path configured for the anatomical feature.

In some embodiments, a computer-readable storage medium system may be summarized as including one or more computer-readable storage mediums storing a program executable by one or more data processing devices of a data processing device system communicatively connected to an input-output device system. The program includes an input module configured to cause reception of transducer data via the input-output device system, the transducer data indicating data acquired by at least some of a plurality of transducers included in a transducer-based device, at least part of the transducer-based device positionable within a bodily cavity. The program includes a graphical representation module configured to cause the input-output device system to display a graphical representation, the graphical representation including a plurality of transducer graphical elements respectively associated with the plurality of transducers of the transducer-based device. The program further includes an identification module configured to cause identification of a region of the graphical representation that corresponds to at least a portion of an anatomical feature based at least on an analysis of the transducer data. The graphical representation module is configured to cause the input-output device system to visually display the identified region of the graphical representation. The program further includes a selection module configured to cause reception of a selection from the input-output device system of the visually-displayed identified region, and a path-display module configured to, in response to receiving the selection, cause the displayed graphical representation to include a displayed visual representation of an ablation path configured for the anatomical feature. In some embodiments, the computer-readable storage medium system is a non-transitory computer-readable storage medium system including one or more non-transitory computer-readable storage mediums storing the program.

A transducer-activation system may be summarized as including a data processing device system, an input-output device system communicatively connected to the data processing device system, and a memory device system communicatively connected to the data processing device system and storing a program executable by the data processing device system. The program includes graphical representation instructions configured to cause the input-output device system to display a graphical representation of at least a portion of a transducer-based device, at least part of the transducer-based device positionable within a bodily cavity. The graphical representation includes a between graphical element associated with a region of space between a first transducer and a second transducer of the transducer-based device, the region of space not including any transducer. The program includes activation instructions configured to cause, via the input-output device system, an energy source device system connected to at least the first transducer and the second transducer to deliver energy to each of the first transducer and the second transducer. The program includes determination instructions configured to cause determination of an energy-delivery status associated with at least one of the first transducer and the second transducer, the energy-delivery status indicating a status of the energy delivery by the energy source device system to the at least one of the first transducer and the second transducer. The program further includes energy-delivery-indication instructions configured to cause the input-output device system to change a displayed visual characteristic of the between graphical element based at least on the determined energy-delivery status of the at least one of the first transducer and the second transducer. The region of space may not be associated with any physical part of the transducer-based device.

The energy-delivery status associated with the at least one of the first transducer and the second transducer may include a pre-energy-delivery status associated with a state before a start of the energy delivery by the energy source device system to the at least one of the first transducer and the second transducer and a during-energy-delivery status associated with a state during the energy delivery by the energy source device system to the at least one of the first transducer and the second transducer. A first displayed visual characteristic of the between graphical element may be associated with the pre-energy-delivery status and a second displayed visual characteristic of the between graphical element may be associated with the during-energy-delivery status, the second displayed visual characteristic being different than the first displayed visual characteristic. The energy-delivery status associated with the at least one of the first transducer and the second transducer may include a post-energy-delivery status associated with a state after a completion of the energy delivery by the energy source device system to the at least one of the first transducer and the second transducer. A third displayed visual characteristic of the between graphical element may be associated with the post-energy delivery status, the third displayed visual characteristic being different than one of the first displayed visual characteristic and the second displayed visual characteristic. The third displayed visual characteristic may be different than the first displayed visual characteristic, the second displayed visual characteristic, or both the first displayed visual characteristic and the second displayed visual characteristic.

The graphical representation may include a first transducer graphical element associated with the first transducer and a second transducer graphical element associated with the second transducer. The energy-delivery-indication instructions may be further configured to cause the input-output device system to change a displayed visual characteristic of the first transducer graphical element, the second transducer graphical element, or both the first transducer graphical element and the second transducer graphical element based at least on the determined energy-delivery status associated with the at least one of the first transducer and the second transducer. The graphical representation may include a first spatial relationship between the first transducer graphical element and the second transducer graphical element that is consistent with a second spatial relationship between the corresponding first transducer and the second transducer of the transducer-based device. The graphical representation instructions may be further configured to display the second transducer graphical element in a first direction from the first transducer graphical element. The between graphical element may be between the second transducer graphical element and the first transducer graphical element in the graphical representation. The between graphical element may be formed, at least in part, at a location in the graphical representation intersected by the first direction from the first transducer graphical element. The between graphical element may include an elongate portion extending along the first direction.

The input-output device system may include the transducer-based device. The transducer-based device may be a catheter device. The bodily cavity may be an intra-cardiac cavity.

Various systems may include combinations and subsets of all those summarized above.

In some embodiments, a transducer-activation system may be summarized as including a data processing device system, an input-output device system communicatively connected to the data processing device system, and a memory device system communicatively connected to the data processing device system and storing a program executable by the data processing device system. The data processing device system is configured by the program at least to cause the input-output device system to display a graphical representation of at least a portion of a transducer-based device, at least part of the transducer-based device positionable within a bodily cavity, and the graphical representation including a between graphical element associated with a region of space between a first transducer and a second transducer of the transducer-based device, the region of space not including any transducer. The data processing device system is configured by the program at least to cause the input-output device system to cause, via the input-output device system, an energy source device system connected to at least the first transducer and the second transducer to deliver energy to each of the first transducer and the second transducer. The data processing device system is configured by the program at least to cause the input-output device system to determine an energy-delivery status associated with at least one of the first transducer and the second transducer, the energy-delivery status indicating a status of the energy delivery by the energy source device system to the at least one of the first transducer and the second transducer. The data processing device system is further configured by the program at least to cause the input-output device system to cause the input-output device system to change a displayed visual characteristic of the between graphical element based at least on the determined energy-delivery status of the at least one of the first transducer and the second transducer.

In some embodiments, a transducer-activation method is executed by a data processing device system according to a program stored by a memory device system communicatively connected to the data processing device system, the data processing device system further communicatively connected to an input-output device system. The method may be summarized as including causing the input-output device system to display a graphical representation of at least a portion of a transducer-based device, at least part of the transducer-based device positionable within a bodily cavity, and the graphical representation including a between graphical element associated with a region of space between a first transducer and a second transducer of the transducer-based device, the region of space not including any transducer. The method includes causing, via the input-output device system, an energy source device system connected to at least the first transducer and the second transducer to deliver energy to each of the first transducer and the second transducer. The method includes determining an energy-delivery status associated with at least one of the first transducer and the second transducer, the energy-delivery status indicating a status of the energy delivery by the energy source device system to the at least one of the first transducer and the second transducer. The method further includes causing the input-output device system to change a displayed visual characteristic of the between graphical element based at least on the determined energy-delivery status of the at least one of the first transducer and the second transducer.

In some embodiments, a computer-readable storage medium system may be summarized as including one or more computer-readable storage mediums storing a program executable by one or more data processing devices of a data processing device system communicatively connected to an input-output device system. The program includes a graphical representation module configured to cause the input-output device system to display a graphical representation of at least a portion of a transducer-based device, at least part of the transducer-based device positionable within a bodily cavity. The graphical representation includes a between graphical element associated with a region of space between a first transducer and a second transducer of the transducer-based device, the region of space not including any transducer. The program includes an activation module configured to cause, via the input-output device system, an energy source device system connected to at least the first transducer and the second transducer to deliver energy to each of the first transducer and the second transducer. The program includes a determination module configured to cause determination of an energy-delivery status associated with at least one of the first transducer and the second transducer, the energy-delivery status indicating a status of the energy delivery by the energy source device system to the at least one of the first transducer and the second transducer. The program further includes an energy-delivery-indication module configured to cause the input-output device system to change a displayed visual characteristic of the between graphical element based at least on the determined energy-delivery status of the at least one of the first transducer and the second transducer. In some embodiments, the computer-readable storage medium system is a non-transitory computer-readable storage medium system including one or more non-transitory computer-readable storage mediums storing the program.

In some embodiments, a transducer-selection system may be summarized as including a data processing device system, an input-output device system communicatively connected to the data processing device system, and a memory device system communicatively connected to the data processing device system and storing a program executable by the data processing device system. The program includes display instructions configured to cause the input-output device system to display a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical element sets, each graphical element set including one or more graphical elements and each graphical element set associated with a respective one of a plurality of pairs of adjacent ones of the transducers in the distribution, no two of the pairs of adjacent ones of the transducers in the distribution having an identical pair of adjacent ones of the transducers in the distribution. The program includes identification instructions configured to cause identification of which of the respective transducers of each of the pairs of adjacent ones of the transducers in the distribution are and which are not acceptable for concurrent selection. The display instructions are configured to cause the input-output device system to display each of the graphical element sets associated with each of the pairs of adjacent ones of the transducers in the distribution whose respective transducers have been identified, according to the identification instructions, to be acceptable for concurrent selection with a respective set of visual characteristics that distinguishes each of the graphical element sets associated with each of the pairs of adjacent ones of the transducers in the distribution whose respective transducers have been identified, according to the identification instructions, to be acceptable for concurrent selection from each of the graphical element sets associated with each of the pairs of adjacent ones of the transducers in the distribution whose respective transducers have been identified, according to the identification instructions, to be not acceptable for concurrent selection.

The program may further include first selection instructions configured to cause selection of at least one graphical element in a first set of the plurality of graphical element sets that is associated with a first pair of the plurality of pairs of adjacent ones of the transducers in the distribution whose respective transducers have been identified, according to the identification instructions, to be acceptable for concurrent selection, and to cause concurrent selection, in response to the selection of the at least one graphical element in the first set of the plurality of graphical element sets, of the respective transducers of the first pair of the plurality of pairs of adjacent ones of the transducers in the distribution. The selection of the at least one graphical element in the first set of the plurality of graphical element sets may include a selection of a particular graphical element in the first set of the plurality of graphical element sets made in response to a user instruction to select a user-selected graphical element in the first set of the plurality of graphical element sets. The program may further include activation instructions configured to, in response to the concurrent selection, cause concurrent activation, via the input-output device system, of each of the respective transducers of the first pair of the plurality of pairs of adjacent ones of the transducers in the distribution. The activation instructions may be configured to, in response to the concurrent selection, cause monopolar activation, via the input-output device system, of each of the respective transducers of the first pair of the plurality of pairs of adjacent ones of the transducers in the distribution. The input-output device system may include the transducer-based device and an energy source device system connected to each of the respective transducers of the first pair of the plurality of pairs of adjacent ones of the transducers in the distribution, and the activation instructions may be further configured to cause energy from the energy source device system to be delivered, for the monopolar activation, to each of the respective transducers of the first pair of the plurality of pairs of adjacent ones of the transducers in the distribution, the energy sufficient to cause ablation of tissue in the bodily cavity. The energy may be sufficient to cause an electrophysiological activity conduction block in the tissue between the respective transducers of the first pair of the plurality of pairs of adjacent ones of the transducers in the distribution.

The input-output device system may include the transducer-based device. The bodily cavity may be an intra-cardiac cavity, and each respective transducer of the first pair of the plurality of pairs of adjacent ones of the transducers in the distribution may be configured to detect electrophysiological activity in the intra-cardiac cavity at a location at least proximate the respective transducer of the first pair of the plurality of pairs of adjacent ones of the transducers in the distribution. The program may further include instructions configured to, in response to the concurrent selection, cause generation of a combined electrogram based at least on input received via the input-output device system from both of the respective transducers of the first pair of the plurality of pairs of adjacent ones of the transducers in the distribution.

The program may further include activation instructions configured to, in response to the concurrent selection, cause bipolar activation, via the input-output device system, between each of the respective transducers of the first pair of the plurality of pairs of adjacent ones of the transducers in the distribution. The input-output device system may include the transducer-based device and an energy source device system connected to each of the respective transducers of the first pair of the plurality of pairs of adjacent ones of the transducers in the distribution. The program may further include activation instructions configured to, in response to the concurrent selection, cause energy from the energy source device system to be delivered to each of the respective transducers of the first pair of the plurality of pairs of adjacent ones of the transducers in the distribution in a manner that, (a) a portion of the energy delivered to a first transducer of the first pair of the plurality of pairs of adjacent ones of the transducers in the distribution is transmitted by the first transducer to a second transducer of the first pair of the plurality of pairs of adjacent ones of the transducers in the distribution, (b) a portion of the energy delivered to the second transducer is transmitted by the second transducer to the first transducer, or both (a) and (b).

The program may further include second selection instructions configured to cause selection of at least one graphical element in a second set of the plurality of graphical element sets that is associated with a second pair of the plurality of pairs of adjacent ones of the transducers in the distribution whose respective transducers have been identified, according to the identification instructions, to be not acceptable for concurrent selection, and to cause non-concurrent selection, in response to the selection of the at least one graphical element in the second set of the plurality of graphical element sets, of the respective transducers of the second pair of the plurality of pairs of adjacent ones of the transducers in the distribution. The first and the second pairs of the plurality of pairs of adjacent ones of the transducers in the distribution may share a same transducer in the distribution. The selection of the at least one graphical element in the first set of the plurality of graphical element sets may be a selection, at one time, of each of the at least one graphical element in the first set of the plurality of graphical element sets, and the selection of the at least one graphical element in the second set of the plurality of graphical element sets may be a selection, over a time interval, of at least two of the graphical elements in the second set of the plurality of graphical element sets. The second set of the plurality of graphical element sets may have a different number of graphical elements than the first set of the plurality of graphical element sets.

The program may further include third selection instructions configured to, (a) in response to receiving a user instruction to select at least a first user-selected graphical element in the first graphical element set, cause the data processing device system to select at least a second graphical element in the first graphical element set, (b) in response to receiving a user instruction to select at least a first user-selected graphical element in the second graphical element set, cause the data processing device system to select at least a second graphical element in the second graphical element set, or both (a) and (b). The program may further include second activation instructions configured to, in response to the non-concurrent selection, cause activation, via the input-output device system, of each of the respective transducers of the second pair of the plurality of pairs of adjacent ones of the transducers in the distribution, the second activation instructions configured to preclude bipolar activation between each of the respective transducers of the second pair of the plurality of pairs of adjacent ones of the transducers in the distribution. The program may further include second activation instructions configured to, in response to the non-concurrent selection, cause non-concurrent activation, via the input-output device system, of each of the respective transducers of the second pair of the plurality of pairs of adjacent ones of the transducers in the distribution.

The graphical representation may include a plurality of transducer graphical elements and one or more between graphical elements, each transducer graphical element associated with a corresponding transducer in the distribution, and each between graphical element associated with a region of space located between the transducers of a corresponding pair of the plurality of pairs of adjacent ones of the transducers in the distribution, the region of space not including any transducer. In some embodiments, none of the plurality of graphical element sets respectively associated with the pairs of adjacent ones of the transducers in the distribution whose respective transducers have been identified, according to the identification instructions, to be not acceptable for concurrent selection include any of the one or more between graphical elements. The region of space associated with at least a first between graphical element of the one or more between graphical elements may not be associated with any physical part of the transducer-based device. The region of space associated with at least a second between graphical element of the one or more between graphical elements may be associated with a physical part of the transducer-based device. The graphical representation may include a first spatial relationship between the plurality of transducer graphical elements that is consistent with a second spatial relationship between the corresponding transducers in the distribution. Each of the one or more between graphical elements may be located in the graphical representation between a respective pair of the transducer graphical elements, each respective pair of the transducer graphical elements associated with a respective pair of adjacent ones of the transducers in the distribution whose respective transducers have been identified, according to the identification instructions, to be acceptable for concurrent selection.

The program may further include instructions configured to cause reception of transducer data via the input-output device system, the transducer data indicating data acquired by at least some of the plurality of transducers. The identification instructions may be further configured to cause, at least in part, the identification of the respective transducers of each of the pairs of adjacent ones of the transducers in the distribution which are acceptable for concurrent selection based at least on an analysis of the transducer data.

The respective transducers of each of the plurality of pairs of adjacent ones of the transducers in the distribution may be spaced with respect to one another across a corresponding region of space, each region of space not including any transducer. The program may further include determination instructions configured to cause determination, via input received from the input-output device system, of which of the regions of space are and which are not acceptable for activation of the corresponding respective transducers of each of the plurality of pairs of adjacent ones of the transducers in the distribution. The identification instructions may be further configured to cause, at least in part, the identification of the respective transducers of each of the pairs of adjacent ones of the transducers in the distribution which are acceptable for concurrent selection as the respective transducers of each of the plurality of pairs of adjacent ones of the transducers in the distribution whose corresponding regions of space have been determined, according to the determination instructions, to be acceptable for activation of the corresponding respective transducers, and cause identification, at least in part, of the respective transducers of each of the pairs of adjacent ones of the transducers in the distribution which are not acceptable for concurrent selection as the respective transducers of each of the plurality of pairs of adjacent ones of the transducers in the distribution whose corresponding regions of space have been determined, according to the determination instructions, to be not acceptable for activation of the corresponding respective transducers.

The program may further include determination instructions configured to cause, via input received from the input-output device system, identification of an activation-ready transducer of the transducer-based device as a transducer of the plurality of transducers that is deemed, based at least on the input, to be located within sufficient proximity to a region of space, the sufficient proximity deemed acceptable for ablation, and cause identification of a not-activation-ready transducer of the transducer-based device as a transducer of the plurality of transducers that is deemed, based at least on an analysis of the input, to not be located within sufficient proximity to a region of space, the sufficient proximity deemed acceptable for ablation. The identification instructions may be further configured to cause, at least in part, the identification of the respective transducers of each of the pairs of adjacent ones of the transducers in the distribution which are acceptable for concurrent selection as the respective transducers of each of the plurality of pairs of adjacent ones of the transducers in the distribution including only transducers which have been identified according to the determination instructions to be activation-ready transducers.

The respective transducers of each of the plurality of pairs of adjacent ones of the transducers in the distribution may be spaced with respect to one another by a respective transducer-to-transducer distance, and the identification instructions may be further configured to cause, at least in part, the identification of the respective transducers of each of the pairs of adjacent ones of the transducers in the distribution which are acceptable for concurrent selection as the respective transducers of each of the plurality of pairs of adjacent ones of the transducers in the distribution whose respective transducer-to-transducer distance is not greater than a target transducer-to-transducer distance, and cause identification, at least in part, of the respective transducers of each of the pairs of adjacent ones of the transducers in the distribution which are not acceptable for concurrent selection as the respective transducers of each of the plurality of pairs of adjacent ones of the transducers in the distribution whose transducer-to-transducer distance are greater than the target transducer-to-transducer distance.

Various systems may include combinations and subsets of all those summarized above.

In some embodiments, a transducer-selection system may be summarized as including a data processing device system, an input-output device system communicatively connected to the data processing device system, and a memory device system communicatively connected to the data processing device system and storing a program executable by the data processing device system. The data processing device system is configured by the program to display, via the input-output device system, a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical element sets, each graphical element set including one or more graphical elements and each graphical element set associated with a respective one of a plurality of pairs of adjacent ones of the transducers in the distribution, no two of the pairs of adjacent ones of the transducers in the distribution having an identical pair of adjacent ones of the transducers in the distribution. The data processing device system is further configured by the program to identify which of the respective transducers of each of the pairs of adjacent ones of the transducers in the distribution are and which are not acceptable for concurrent selection, and display, via the input-output device system, each of the graphical element sets associated with each of the pairs of adjacent ones of the transducers in the distribution whose respective transducers have been identified to be acceptable for concurrent selection with a respective set of visual characteristics that distinguishes each of the graphical element sets associated with each of the pairs of adjacent ones of the transducers in the distribution whose respective transducers have been identified to be acceptable for concurrent selection from each of the graphical element sets associated with each of the pairs of adjacent ones of the transducers in the distribution whose respective transducers have been identified to be not acceptable for concurrent selection.

In some embodiments, a transducer-selection method is executed by a data processing device system according to a program stored by a memory device system communicatively connected to the data processing device system, the data processing device system further communicatively connected to an input-output device system. The method includes displaying, via the input-output device system, a graphical representation of at least a portion of a transducer-based device, the transducer-based device including a structure and a plurality of transducers located on the structure, the plurality of transducers arranged in a distribution positionable in a bodily cavity, and the graphical representation including a plurality of graphical element sets, each graphical element set including one or more graphical elements and each graphical element set associated with a respective one of a plurality of pairs of adjacent ones of the transducers in the distribution, no two of the pairs of adjacent ones of the transducers in the distribution having an identical pair of adjacent ones of the transducers in the distribution. The method includes identifying which of the respective transducers of each of the pairs of adjacent ones of the transducers in the distribution are and which are not acceptable for concurrent selection. The method further includes displaying, via the input-output device system, each of the graphical element sets associated with each of the pairs of adjacent ones of the transducers in the distribution whose respective transducers have been identified to be acceptable for concurrent selection with a respective set of visual characteristics that distinguishes each of the graphical element sets associated with each of the pairs of adjacent ones of the transducers in the distribution whose respective transducers have been identified to be acceptable for concurrent selection from each of the graphical element sets associated with each of the pairs of adjacent ones of the transducers in the distribution whose respective transducers have been identified to be not acceptable for concurrent selection.

In some embodiments, a computer-readable storage medium system may be summarized as including one or more computer-readable storage mediums storing a program executable by one or more data processing devices of a data processing device system communicatively connected to an input-output device system. The program includes a display module configured to cause the input-output device system to display a graphical representation of at least a portion of a transducer-based device, the transducer-based device including a structure and a plurality of transducers located on the structure, the plurality of transducers arranged in a distribution positionable in a bodily cavity, and the graphical representation including a plurality of graphical element sets, each graphical element set including one or more graphical elements and each graphical element set associated with a respective one of a plurality of pairs of adjacent ones of the transducers in the distribution, no two of the pairs of adjacent ones of the transducers in the distribution having an identical pair of adjacent ones of the transducers in the distribution. The program further includes an identification module configured to cause identification of which of the respective transducers of each of the pairs of adjacent ones of the transducers in the distribution are and which are not acceptable for concurrent selection. The display module is configured to cause the input-output device system to display each of the graphical element sets associated with each of the pairs of adjacent ones of the transducers in the distribution whose respective transducers have been identified, according to the identification module, to be acceptable for concurrent selection with a respective set of visual characteristics that distinguishes each of the graphical element sets associated with each of the pairs of adjacent ones of the transducers in the distribution whose respective transducers have been identified, according to the identification module, to be acceptable for concurrent selection from each of the graphical element sets associated with each of the pairs of adjacent ones of the transducers in the distribution whose respective transducers have been identified, according to the identification module, to be not acceptable for concurrent selection. In some embodiments, the computer-readable storage medium system is a non-transitory computer-readable storage medium system including one or more non-transitory computer-readable storage mediums storing the program.

In some embodiments, a transducer-activation system may be summarized as including a data processing device system, an input-output device system communicatively connected to the data processing device system, and a memory device system communicatively connected to the data processing device system and storing a program executable by the data processing device system. The program includes display instructions configured to cause the input-output device system to display a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical elements, the plurality of graphical elements including a group of transducer graphical elements, each transducer graphical element in the group corresponding to a respective one of the transducers in the distribution. The program further includes first selection instructions configured to cause a first selection from the plurality of graphical elements of at least one graphical element in a first graphical element set from the plurality of graphical elements and first activation instructions configured to, in response to the first selection, cause activation, via the input-output device system, of each transducer of a first pair of the transducers in the distribution, the first pair of the transducers in the distribution having a first transducer and a second transducer. The program further includes second selection instructions configured to cause a second selection from the plurality of graphical elements of at least one graphical element in a second graphical element set from the plurality of graphical elements, and second activation instructions configured to, in response to the second selection, cause activation, via the input-output device system, of each transducer of a second pair of the transducers in the distribution, the second pair of the transducers in the distribution having the first transducer and a third transducer. Each of the first, the second, and the third transducers are different transducers in the distribution, and the first selection does not include a selection of a user-selected transducer graphical element in the group made in response to a user instruction to select the user-selected transducer graphical element in the group.

The first selection may include a selection of a user-selected graphical element in the first graphical element set made in response to a user instruction to select the user-selected graphical element in the first graphical element set. The program may further include third selection instructions configured to, in response to receiving a user instruction to select at least one user-selected graphical element in the first graphical element set, cause the data processing device system to select at least a second graphical element of the plurality of graphical elements. The second graphical element may be a particular one of the transducer graphical elements in the group. The first activation instructions may be further configured to, in response to the selection of the at least the second graphical element, cause activation, via the input-output device system, of each transducer of the first pair of the transducers in the distribution. The display instructions may be further configured to, in response to the first selection, cause the input-output device system to change a visual characteristic of at least a portion of the second graphical element.

The second selection may include a selection of a user-selected graphical element in the second graphical element set made in response to a user instruction to select the user-selected graphical element in the second graphical element set. The third selection instructions may be configured to, in response to receiving a user instruction to select at least one user-selected graphical element in the second graphical element set, cause the data processing device system to select at least a third graphical element of the plurality of graphical elements. The third graphical element may be the second graphical element.

Each of the first selection and the second selection may not include a selection of a transducer graphical element in the group made in response to a user instruction to select the transducer graphical element in the group. The second selection may include a selection of at least two transducer graphical elements in the group.

The first activation instructions may be further configured to, in response to the first selection, cause concurrent activation, via the input-output device system, of each transducer of the first pair of the transducers in the distribution. The second activation instructions may be configured to, in response to the second selection, cause non-concurrent activation, via the input-output device system, of each transducer of the second pair of the transducers in the distribution.

Each of the first and the second pairs of transducers in the distribution may be a respective pair of a plurality of pairs of adjacent ones of the transducers in the distribution. The plurality of graphical elements may include at least one between graphical element, each between graphical element associated with a region of space located between the transducers of a corresponding pair of the plurality of pairs of adjacent ones of the transducers in the distribution, the region of space not including any transducer. The first graphical element set, the second graphical element set, or each of both the first and the second graphical element sets may include one of the at least one between graphical element. The region of space associated with at least a first between graphical element of the at least one between graphical element may not be associated with any physical part of the transducer-based device. The region of space associated with at least a second between graphical element of the at least one between graphical element may be associated with a physical part of the transducer-based device.

The graphical representation may include a first spatial relationship between the plurality of transducer graphical elements that is consistent with a second spatial relationship between the corresponding ones of the transducers in the distribution.

Various systems may include combinations and subsets of all those summarized above.

In some embodiments, a transducer-activation system may be summarized as including a data processing device system, an input-output device system communicatively connected to the data processing device system, and a memory device system communicatively connected to the data processing device system and storing a program executable by the data processing device system. The data processing device system is configured by the program to display, via the input-output device system, a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical elements, the plurality of graphical elements including a group of transducer graphical elements, each transducer graphical element in the group corresponding to a respective one of the transducers in the distribution. The data processing device system is configured by the program to select, via a first selection from the plurality of graphical elements, at least one graphical element in a first graphical element set from the plurality of graphical elements and activate, in response to the first selection and via the input-output device system, each transducer of a first pair of the transducers in the distribution, the first pair of the transducers in the distribution having a first transducer and a second transducer. The data processing device system is configured by the program to select, via a second selection from the plurality of graphical elements, at least one graphical element in a second graphical element set from the plurality of graphical elements, and activate, in response to the second selection and via the input-output device system, each transducer of a second pair of the transducers in the distribution, the second pair of the transducers in the distribution having the first transducer and a third transducer. Each of the first, the second, and the third transducers are different transducers in the distribution, and the first selection does not include a selection of a user-selected transducer graphical element in the group made in response to a user instruction to select the user-selected transducer graphical element in the group.

In some embodiments, a transducer-activation method is executed by a data processing device system according to a program stored by a memory device system communicatively connected to the data processing device system, the data processing device system further communicatively connected to an input-output device system. The method includes displaying, via the input-output device system, a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical elements, the plurality of graphical elements including a group of transducer graphical elements, each transducer graphical element in the group corresponding to a respective one of the transducers in the distribution. The method further includes selecting, via a first selection from the plurality of graphical elements, at least one graphical element in a first graphical element set from the plurality of graphical elements and activating, in response to the first selection and via the input-output device system, each transducer of a first pair of the transducers in the distribution, the first pair of the transducers in the distribution having a first transducer and a second transducer. The method further includes selecting, via a second selection from the plurality of graphical elements, at least one graphical element in a second graphical element set from the plurality of graphical elements, and activating, in response to the second selection and via the input-output device system, each transducer of a second pair of the transducers in the distribution, the second pair of the transducers in the distribution having the first transducer and a third transducer. Each of the first, the second, and the third transducers are different transducers in the distribution, and the first selection does not include a selection of a user-selected transducer graphical element in the group made in response to a user instruction to select the user-selected transducer graphical element in the group.

In some embodiments, a computer-readable storage medium system may be summarized as including one or more computer-readable storage mediums storing a program executable by one or more data processing devices of a data processing device system communicatively connected to an input-output device system. The program includes a display module configured to cause the input-output device system to display a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical elements, the plurality of graphical elements including a group of transducer graphical elements, each transducer graphical element in the group corresponding to a respective one of the transducers in the distribution. The program includes a first selection module configured to cause selection of a first selection from the plurality of graphical elements of at least one graphical element in a first graphical element set from the plurality of graphical elements, and a first activation module configured to, in response to the first selection, cause activation, via the input-output device system, of each transducer of a first pair of the transducers in the distribution, the first pair of the transducers in the distribution having a first transducer and a second transducer. The program further includes a second selection module configured to cause selection of a second selection from the plurality of graphical elements of at least one graphical element in a second graphical element set from the plurality of graphical elements, and a second activation module configured to, in response to the second selection, cause activation, via the input-output device system, of each transducer of a second pair of the transducers in the distribution, the second pair of the transducers in the distribution having the first transducer and a third transducer. Each of the first, the second, and the third transducers are different transducers in the distribution, and the first selection does not include a selection of a user-selected transducer graphical element in the group made in response to a user instruction to select the user-selected transducer graphical element in the group. In some embodiments, the computer-readable storage medium system is a non-transitory computer-readable storage medium system including one or more non-transitory computer-readable storage mediums storing the program.

In some embodiments, a transducer-selection system may be summarized as including a data processing device system, an input-output device system communicatively connected to the data processing device system, and a memory device system communicatively connected to the data processing device system and storing a program executable by the data processing device system. The program includes display instructions configured to cause the input-output device system to display a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical element sets, each graphical element set including one or more graphical elements and each graphical element set associated with a respective one of a plurality of pairs of adjacent ones of the transducers in the distribution, no two of the pairs of adjacent ones of the transducers in the distribution having an identical pair of adjacent ones of the transducers in the distribution. The program includes identification instructions configured to cause identification of which of the respective transducers of each of the pairs of adjacent ones of the transducers in the distribution are and which are not acceptable for concurrent selection. The display instructions are configured to cause the input-output device system to display each of the graphical element sets associated with each of the pairs of adjacent ones of the transducers in the distribution whose respective transducers have been identified, according to the identification instructions, to be acceptable for concurrent selection with a respective set of visual characteristics that distinguishes each of the graphical element sets associated with each of the pairs of adjacent ones of the transducers in the distribution whose respective transducers have been identified, according to the identification instructions, to be acceptable for concurrent selection from each of the graphical element sets associated with each of the pairs of adjacent ones of the transducers in the distribution whose respective transducers have been identified, according to the identification instructions, to be not acceptable for concurrent selection.

The program may further include first selection instructions configured to cause selection of at least one graphical element in a first set of the plurality of graphical element sets that is associated with a first pair of the plurality of pairs of adjacent ones of the transducers in the distribution whose respective transducers have been identified, according to the identification instructions, to be acceptable for concurrent selection, and to cause concurrent selection, in response to the selection of the at least one graphical element in the first set of the plurality of graphical element sets, of the respective transducers of the first pair of the plurality of pairs of adjacent ones of the transducers in the distribution. The selection of the at least one graphical element in the first set of the plurality of graphical element sets may include a selection of a particular graphical element in the first set of the plurality of graphical element sets made in response to a user instruction to select a user-selected graphical element in the first set of the plurality of graphical element sets. The program may further include activation instructions configured to, in response to the concurrent selection, cause concurrent activation, via the input-output device system, of each of the respective transducers of the first pair of the plurality of pairs of adjacent ones of the transducers in the distribution. The activation instructions may be configured to, in response to the concurrent selection, cause monopolar activation, via the input-output device system, of each of the respective transducers of the first pair of the plurality of pairs of adjacent ones of the transducers in the distribution. The input-output device system may include the transducer-based device and an energy source device system connected to each of the respective transducers of the first pair of the plurality of pairs of adjacent ones of the transducers in the distribution, and the activation instructions may be further configured to cause energy from the energy source device system to be delivered, for the monopolar activation, to each of the respective transducers of the first pair of the plurality of pairs of adjacent ones of the transducers in the distribution, the energy sufficient to cause ablation of tissue in the bodily cavity. The energy may be sufficient to cause an electrophysiological activity conduction block in the tissue between the respective transducers of the first pair of the plurality of pairs of adjacent ones of the transducers in the distribution.

The input-output device system may include the transducer-based device. The bodily cavity may be an intra-cardiac cavity, and each respective transducer of the first pair of the plurality of pairs of adjacent ones of the transducers in the distribution may be configured to detect electrophysiological activity in the intra-cardiac cavity at a location at least proximate the respective transducer of the first pair of the plurality of pairs of adjacent ones of the transducers in the distribution. The program may further include instructions configured to, in response to the concurrent selection, cause generation of a combined electrogram based at least on input received via the input-output device system from both of the respective transducers of the first pair of the plurality of pairs of adjacent ones of the transducers in the distribution.

The program may further include activation instructions configured to, in response to the concurrent selection, cause bipolar activation, via the input-output device system, between each of the respective transducers of the first pair of the plurality of pairs of adjacent ones of the transducers in the distribution. The input-output device system may include the transducer-based device and an energy source device system connected to each of the respective transducers of the first pair of the plurality of pairs of adjacent ones of the transducers in the distribution. The program may further include activation instructions configured to, in response to the concurrent selection, cause energy from the energy source device system to be delivered to each of the respective transducers of the first pair of the plurality of pairs of adjacent ones of the transducers in the distribution in a manner that, (a) a portion of the energy delivered to a first transducer of the first pair of the plurality of pairs of adjacent ones of the transducers in the distribution is transmitted by the first transducer to a second transducer of the first pair of the plurality of pairs of adjacent ones of the transducers in the distribution, (b) a portion of the energy delivered to the second transducer is transmitted by the second transducer to the first transducer, or both (a) and (b).

The program may further include second selection instructions configured to cause selection of at least one graphical element in a second set of the plurality of graphical element sets that is associated with a second pair of the plurality of pairs of adjacent ones of the transducers in the distribution whose respective transducers have been identified, according to the identification instructions, to be not acceptable for concurrent selection, and to cause non-concurrent selection, in response to the selection of the at least one graphical element in the second set of the plurality of graphical element sets, of the respective transducers of the second pair of the plurality of pairs of adjacent ones of the transducers in the distribution. The first and the second pairs of the plurality of pairs of adjacent ones of the transducers in the distribution may share a same transducer in the distribution. The selection of the at least one graphical element in the first set of the plurality of graphical element sets may be a selection, at one time, of each of the at least one graphical element in the first set of the plurality of graphical element sets, and the selection of the at least one graphical element in the second set of the plurality of graphical element sets may be a selection, over a time interval, of at least two of the graphical elements in the second set of the plurality of graphical element sets. The second set of the plurality of graphical element sets may have a different number of graphical elements than the first set of the plurality of graphical element sets.

The program may further include third selection instructions configured to, (a) in response to receiving a user instruction to select at least a first user-selected graphical element in the first graphical element set, cause the data processing device system to select at least a second graphical element in the first graphical element set, (b) in response to receiving a user instruction to select at least a first user-selected graphical element in the second graphical element set, cause the data processing device system to select at least a second graphical element in the second graphical element set, or both (a) and (b). The program may further include second activation instructions configured to, in response to the non-concurrent selection, cause activation, via the input-output device system, of each of the respective transducers of the second pair of the plurality of pairs of adjacent ones of the transducers in the distribution, the second activation instructions configured to preclude bipolar activation between each of the respective transducers of the second pair of the plurality of pairs of adjacent ones of the transducers in the distribution. The program may further include second activation instructions configured to, in response to the non-concurrent selection, cause non-concurrent activation, via the input-output device system, of each of the respective transducers of the second pair of the plurality of pairs of adjacent ones of the transducers in the distribution.

The graphical representation may include a plurality of transducer graphical elements and one or more between graphical elements, each transducer graphical element associated with a corresponding transducer in the distribution, and each between graphical element associated with a region of space located between the transducers of a corresponding pair of the plurality of pairs of adjacent ones of the transducers in the distribution, the region of space not including any transducer. In some embodiments, none of the plurality of graphical element sets respectively associated with the pairs of adjacent ones of the transducers in the distribution whose respective transducers have been identified, according to the identification instructions, to be not acceptable for concurrent selection include any of the one or more between graphical elements. The region of space associated with at least a first between graphical element of the one or more between graphical elements may not be associated with any physical part of the transducer-based device. The region of space associated with at least a second between graphical element of the one or more between graphical elements may be associated with a physical part of the transducer-based device. The graphical representation may include a first spatial relationship between the plurality of transducer graphical elements that is consistent with a second spatial relationship between the corresponding transducers in the distribution. Each of the one or more between graphical elements may be located in the graphical representation between a respective pair of the transducer graphical elements, each respective pair of the transducer graphical elements associated with a respective pair of adjacent ones of the transducers in the distribution whose respective transducers have been identified, according to the identification instructions, to be acceptable for concurrent selection.

The program may further include instructions configured to cause reception of transducer data via the input-output device system, the transducer data indicating data acquired by at least some of the plurality of transducers. The identification instructions may be further configured to cause, at least in part, the identification of the respective transducers of each of the pairs of adjacent ones of the transducers in the distribution which are acceptable for concurrent selection based at least on an analysis of the transducer data.

The respective transducers of each of the plurality of pairs of adjacent ones of the transducers in the distribution may be spaced with respect to one another across a corresponding region of space, each region of space not including any transducer. The program may further include determination instructions configured to cause determination, via input received from the input-output device system, of which of the regions of space are and which are not acceptable for activation of the corresponding respective transducers of each of the plurality of pairs of adjacent ones of the transducers in the distribution. The identification instructions may be further configured to cause, at least in part, the identification of the respective transducers of each of the pairs of adjacent ones of the transducers in the distribution which are acceptable for concurrent selection as the respective transducers of each of the plurality of pairs of adjacent ones of the transducers in the distribution whose corresponding regions of space have been determined, according to the determination instructions, to be acceptable for activation of the corresponding respective transducers, and cause identification, at least in part, of the respective transducers of each of the pairs of adjacent ones of the transducers in the distribution which are not acceptable for concurrent selection as the respective transducers of each of the plurality of pairs of adjacent ones of the transducers in the distribution whose corresponding regions of space have been determined, according to the determination instructions, to be not acceptable for activation of the corresponding respective transducers.

The program may further include determination instructions configured to cause, via input received from the input-output device system, identification of an activation-ready transducer of the transducer-based device as a transducer of the plurality of transducers that is deemed, based at least on the input, to be located within sufficient proximity to a region of space, the sufficient proximity deemed acceptable for ablation, and cause identification of a not-activation-ready transducer of the transducer-based device as a transducer of the plurality of transducers that is deemed, based at least on an analysis of the input, to not be located within sufficient proximity to a region of space, the sufficient proximity deemed acceptable for ablation. The identification instructions may be further configured to cause, at least in part, the identification of the respective transducers of each of the pairs of adjacent ones of the transducers in the distribution which are acceptable for concurrent selection as the respective transducers of each of the plurality of pairs of adjacent ones of the transducers in the distribution including only transducers which have been identified according to the determination instructions to be activation-ready transducers.

The respective transducers of each of the plurality of pairs of adjacent ones of the transducers in the distribution may be spaced with respect to one another by a respective transducer-to-transducer distance, and the identification instructions may be further configured to cause, at least in part, the identification of the respective transducers of each of the pairs of adjacent ones of the transducers in the distribution which are acceptable for concurrent selection as the respective transducers of each of the plurality of pairs of adjacent ones of the transducers in the distribution whose respective transducer-to-transducer distance is not greater than a target transducer-to-transducer distance, and cause identification, at least in part, of the respective transducers of each of the pairs of adjacent ones of the transducers in the distribution which are not acceptable for concurrent selection as the respective transducers of each of the plurality of pairs of adjacent ones of the transducers in the distribution whose transducer-to-transducer distance are greater than the target transducer-to-transducer distance.

Various systems may include combinations and subsets of all those summarized above.

In some embodiments, a transducer-selection system may be summarized as including a data processing device system, an input-output device system communicatively connected to the data processing device system, and a memory device system communicatively connected to the data processing device system and storing a program executable by the data processing device system. The data processing device system is configured by the program to display, via the input-output device system, a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical element sets, each graphical element set including one or more graphical elements and each graphical element set associated with a respective one of a plurality of pairs of adjacent ones of the transducers in the distribution, no two of the pairs of adjacent ones of the transducers in the distribution having an identical pair of adjacent ones of the transducers in the distribution. The data processing device system is further configured by the program to identify which of the respective transducers of each of the pairs of adjacent ones of the transducers in the distribution are and which are not acceptable for concurrent selection, and display, via the input-output device system, each of the graphical element sets associated with each of the pairs of adjacent ones of the transducers in the distribution whose respective transducers have been identified to be acceptable for concurrent selection with a respective set of visual characteristics that distinguishes each of the graphical element sets associated with each of the pairs of adjacent ones of the transducers in the distribution whose respective transducers have been identified to be acceptable for concurrent selection from each of the graphical element sets associated with each of the pairs of adjacent ones of the transducers in the distribution whose respective transducers have been identified to be not acceptable for concurrent selection.

In some embodiments, a transducer-selection method is executed by a data processing device system according to a program stored by a memory device system communicatively connected to the data processing device system, the data processing device system further communicatively connected to an input-output device system. The method includes displaying, via the input-output device system, a graphical representation of at least a portion of a transducer-based device, the transducer-based device including a structure and a plurality of transducers located on the structure, the plurality of transducers arranged in a distribution positionable in a bodily cavity, and the graphical representation including a plurality of graphical element sets, each graphical element set including one or more graphical elements and each graphical element set associated with a respective one of a plurality of pairs of adjacent ones of the transducers in the distribution, no two of the pairs of adjacent ones of the transducers in the distribution having an identical pair of adjacent ones of the transducers in the distribution. The method includes identifying which of the respective transducers of each of the pairs of adjacent ones of the transducers in the distribution are and which are not acceptable for concurrent selection. The method further includes displaying, via the input-output device system, each of the graphical element sets associated with each of the pairs of adjacent ones of the transducers in the distribution whose respective transducers have been identified to be acceptable for concurrent selection with a respective set of visual characteristics that distinguishes each of the graphical element sets associated with each of the pairs of adjacent ones of the transducers in the distribution whose respective transducers have been identified to be acceptable for concurrent selection from each of the graphical element sets associated with each of the pairs of adjacent ones of the transducers in the distribution whose respective transducers have been identified to be not acceptable for concurrent selection.

In some embodiments, a computer-readable storage medium system may be summarized as including one or more computer-readable storage mediums storing a program executable by one or more data processing devices of a data processing device system communicatively connected to an input-output device system. The program includes a display module configured to cause the input-output device system to display a graphical representation of at least a portion of a transducer-based device, the transducer-based device including a structure and a plurality of transducers located on the structure, the plurality of transducers arranged in a distribution positionable in a bodily cavity, and the graphical representation including a plurality of graphical element sets, each graphical element set including one or more graphical elements and each graphical element set associated with a respective one of a plurality of pairs of adjacent ones of the transducers in the distribution, no two of the pairs of adjacent ones of the transducers in the distribution having an identical pair of adjacent ones of the transducers in the distribution. The program further includes an identification module configured to cause identification of which of the respective transducers of each of the pairs of adjacent ones of the transducers in the distribution are and which are not acceptable for concurrent selection. The display module is configured to cause the input-output device system to display each of the graphical element sets associated with each of the pairs of adjacent ones of the transducers in the distribution whose respective transducers have been identified, according to the identification module, to be acceptable for concurrent selection with a respective set of visual characteristics that distinguishes each of the graphical element sets associated with each of the pairs of adjacent ones of the transducers in the distribution whose respective transducers have been identified, according to the identification module, to be acceptable for concurrent selection from each of the graphical element sets associated with each of the pairs of adjacent ones of the transducers in the distribution whose respective transducers have been identified, according to the identification module, to be not acceptable for concurrent selection. In some embodiments, the computer-readable storage medium system is a non-transitory computer-readable storage medium system including one or more non-transitory computer-readable storage mediums storing the program.

In some embodiments, a transducer-activation system may be summarized as including a data processing device system, an input-output device system communicatively connected to the data processing device system, and a memory device system communicatively connected to the data processing device system and storing a program executable by the data processing device system. The program includes display instructions configured to cause the input-output device system to display a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical elements, the plurality of graphical elements including a group of transducer graphical elements, each transducer graphical element in the group corresponding to a respective one of the transducers in the distribution. The program further includes first selection instructions configured to cause a first selection from the plurality of graphical elements of at least one graphical element in a first graphical element set from the plurality of graphical elements and first activation instructions configured to, in response to the first selection, cause activation, via the input-output device system, of each transducer of a first pair of the transducers in the distribution, the first pair of the transducers in the distribution having a first transducer and a second transducer. The program further includes second selection instructions configured to cause a second selection from the plurality of graphical elements of at least one graphical element in a second graphical element set from the plurality of graphical elements, and second activation instructions configured to, in response to the second selection, cause activation, via the input-output device system, of each transducer of a second pair of the transducers in the distribution, the second pair of the transducers in the distribution having the first transducer and a third transducer. Each of the first, the second, and the third transducers are different transducers in the distribution, and the first selection does not include a selection of a user-selected transducer graphical element in the group made in response to a user instruction to select the user-selected transducer graphical element in the group.

The first selection may include a selection of a user-selected graphical element in the first graphical element set made in response to a user instruction to select the user-selected graphical element in the first graphical element set. The program may further include third selection instructions configured to, in response to receiving a user instruction to select at least one user-selected graphical element in the first graphical element set, cause the data processing device system to select at least a second graphical element of the plurality of graphical elements. The second graphical element may be a particular one of the transducer graphical elements in the group. The first activation instructions may be further configured to, in response to the selection of the at least the second graphical element, cause activation, via the input-output device system, of each transducer of the first pair of the transducers in the distribution. The display instructions may be further configured to, in response to the first selection, cause the input-output device system to change a visual characteristic of at least a portion of the second graphical element.

The second selection may include a selection of a user-selected graphical element in the second graphical element set made in response to a user instruction to select the user-selected graphical element in the second graphical element set. The third selection instructions may be configured to, in response to receiving a user instruction to select at least one user-selected graphical element in the second graphical element set, cause the data processing device system to select at least a third graphical element of the plurality of graphical elements. The third graphical element may be the second graphical element.

Each of the first selection and the second selection may not include a selection of a transducer graphical element in the group made in response to a user instruction to select the transducer graphical element in the group. The second selection may include a selection of at least two transducer graphical elements in the group.

The first activation instructions may be further configured to, in response to the first selection, cause concurrent activation, via the input-output device system, of each transducer of the first pair of the transducers in the distribution. The second activation instructions may be configured to, in response to the second selection, cause non-concurrent activation, via the input-output device system, of each transducer of the second pair of the transducers in the distribution.

Each of the first and the second pairs of transducers in the distribution may be a respective pair of a plurality of pairs of adjacent ones of the transducers in the distribution. The plurality of graphical elements may include at least one between graphical element, each between graphical element associated with a region of space located between the transducers of a corresponding pair of the plurality of pairs of adjacent ones of the transducers in the distribution, the region of space not including any transducer. The first graphical element set, the second graphical element set, or each of both the first and the second graphical element sets may include one of the at least one between graphical element. The region of space associated with at least a first between graphical element of the at least one between graphical element may not be associated with any physical part of the transducer-based device. The region of space associated with at least a second between graphical element of the at least one between graphical element may be associated with a physical part of the transducer-based device.

The graphical representation may include a first spatial relationship between the plurality of transducer graphical elements that is consistent with a second spatial relationship between the corresponding ones of the transducers in the distribution.

Various systems may include combinations and subsets of all those summarized above.

In some embodiments, a transducer-activation system may be summarized as including a data processing device system, an input-output device system communicatively connected to the data processing device system, and a memory device system communicatively connected to the data processing device system and storing a program executable by the data processing device system. The data processing device system is configured by the program to display, via the input-output device system, a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical elements, the plurality of graphical elements including a group of transducer graphical elements, each transducer graphical element in the group corresponding to a respective one of the transducers in the distribution. The data processing device system is configured by the program to select, via a first selection from the plurality of graphical elements, at least one graphical element in a first graphical element set from the plurality of graphical elements and activate, in response to the first selection and via the input-output device system, each transducer of a first pair of the transducers in the distribution, the first pair of the transducers in the distribution having a first transducer and a second transducer. The data processing device system is configured by the program to select, via a second selection from the plurality of graphical elements, at least one graphical element in a second graphical element set from the plurality of graphical elements, and activate, in response to the second selection and via the input-output device system, each transducer of a second pair of the transducers in the distribution, the second pair of the transducers in the distribution having the first transducer and a third transducer. Each of the first, the second, and the third transducers are different transducers in the distribution, and the first selection does not include a selection of a user-selected transducer graphical element in the group made in response to a user instruction to select the user-selected transducer graphical element in the group.

In some embodiments, a transducer-activation method is executed by a data processing device system according to a program stored by a memory device system communicatively connected to the data processing device system, the data processing device system further communicatively connected to an input-output device system. The method includes displaying, via the input-output device system, a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical elements, the plurality of graphical elements including a group of transducer graphical elements, each transducer graphical element in the group corresponding to a respective one of the transducers in the distribution. The method further includes selecting, via a first selection from the plurality of graphical elements, at least one graphical element in a first graphical element set from the plurality of graphical elements and activating, in response to the first selection and via the input-output device system, each transducer of a first pair of the transducers in the distribution, the first pair of the transducers in the distribution having a first transducer and a second transducer. The method further includes selecting, via a second selection from the plurality of graphical elements, at least one graphical element in a second graphical element set from the plurality of graphical elements, and activating, in response to the second selection and via the input-output device system, each transducer of a second pair of the transducers in the distribution, the second pair of the transducers in the distribution having the first transducer and a third transducer. Each of the first, the second, and the third transducers are different transducers in the distribution, and the first selection does not include a selection of a user-selected transducer graphical element in the group made in response to a user instruction to select the user-selected transducer graphical element in the group.

In some embodiments, a computer-readable storage medium system may be summarized as including one or more computer-readable storage mediums storing a program executable by one or more data processing devices of a data processing device system communicatively connected to an input-output device system. The program includes a display module configured to cause the input-output device system to display a graphical representation of at least a portion of a transducer-based device, the transducer-based device including a structure and a plurality of transducers located on the structure, the plurality of transducers arranged in a distribution positionable in a bodily cavity. The graphical representation includes a plurality of graphical elements, the plurality of graphical elements including a group of transducer graphical elements, each transducer graphical element in the group corresponding to a respective one of the transducers in the distribution. The program includes a first selection module configured to cause selection of a first selection from the plurality of graphical elements of at least one graphical element in a first graphical element set from the plurality of graphical elements, and a first activation module configured to, in response to the first selection, cause activation, via the input-output device system, of each transducer of a first pair of the transducers in the distribution, the first pair of the transducers in the distribution having a first transducer and a second transducer. The program further includes a second selection module configured to cause selection of a second selection from the plurality of graphical elements of at least one graphical element in a second graphical element set from the plurality of graphical elements, and a second activation module configured to, in response to the second selection, cause activation, via the input-output device system, of each transducer of a second pair of the transducers in the distribution, the second pair of the transducers in the distribution having the first transducer and a third transducer. Each of the first, the second, and the third transducers are different transducers in the distribution, and the first selection does not include a selection of a user-selected transducer graphical element in the group made in response to a user instruction to select the user-selected transducer graphical element in the group. In some embodiments, the computer-readable storage medium system is a non-transitory computer-readable storage medium system including one or more non-transitory computer-readable storage mediums storing the program.

Various systems may include combinations and subsets of all the systems summarized above. Various methods may include combinations and subsets of all the methods summarized above.

BRIEF DESCRIPTION OF THE DRAWINGS

It is to be understood that the attached drawings are for purposes of illustrating aspects of various embodiments and may include elements that are not to scale.

DETAILED DESCRIPTION

Figure 1:
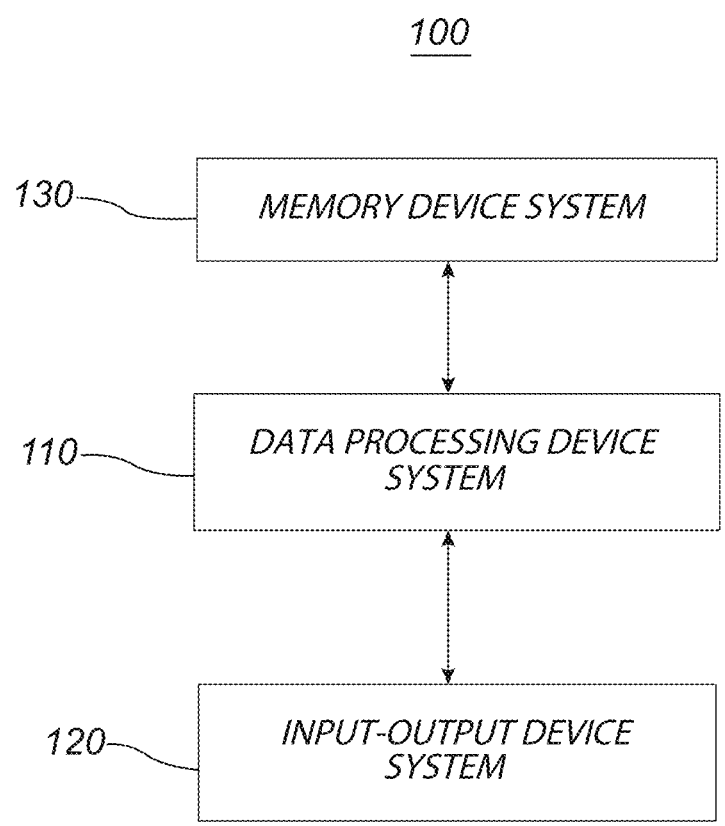
FIG. 1 illustrates a schematic representation of a transducer-activation system according to various example embodiments, the transducer-activation system including a data processing device system, an input-output device system, and a memory device system.

In the following description, certain specific details are set forth in order to provide a thorough understanding of various embodiments of the invention. However, one skilled in the art will understand that the invention may be practiced without these details. In other instances, well-known structures (e.g., structures associated with radio-frequency (RF) ablation and electronic controls such as multiplexers) have not been shown or described in detail to avoid unnecessarily obscuring descriptions of various embodiments of the invention.

Reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, the appearances of the phrases "in one embodiment" or "in an embodiment" or "in an example embodiment" or "in this illustrated embodiment" or "in this particular embodiment" and the like in various places throughout this specification are not necessarily all referring to one embodiment or a same embodiment. Furthermore, the particular features, structures or characteristics of different embodiments may be combined in any suitable manner to form one or more other embodiments.

It is noted that, unless otherwise explicitly noted or required by context, the word "or" is used in this disclosure in a non-exclusive sense. In addition, unless otherwise explicitly noted or required by context, the word "set" is intended to mean one or more.

Further, the phrase "at least" is used herein at times to emphasize the possibility that other elements can exist besides those explicitly listed. However, unless otherwise explicitly noted (such as by the use of the term "only") or required by context, non-usage herein of the phrase "at least" does not exclude the possibility that other elements can exist besides those explicitly listed. For example, the phrase, "activation of at least transducer A" includes activation of transducer A by itself, as well as activation of transducer A and activation of one or more other additional elements besides transducer A. In the same manner, the phrase, "activation of transducer A" includes activation of transducer A by itself, as well as activation of transducer A and activation of one or more other additional elements besides transducer A. However, the phrase, "activation of only transducer A" includes only activation of transducer A, and excludes activation of any other transducers besides transducer A.

The word "ablation" as used in this disclosure should be understood to include any disruption to certain properties of tissue. Most commonly, the disruption is to the electrical conductivity and is achieved by heating, which can be generated with resistive or radio-frequency (RF) techniques for example. Other properties, such as mechanical or chemical, and other means of disruption, such as optical, are included when the term "ablation" is used.

The word "fluid" as used in this disclosure should be understood to include any fluid that can be contained within a bodily cavity or can flow into or out of, or both into and out of a bodily cavity via one or more bodily openings positioned in fluid communication with the bodily cavity. In the case of cardiac applications, fluid such as blood will flow into and out of various intra-cardiac cavities (e.g., a left atrium or right atrium).

The words "bodily opening" as used in this disclosure should be understood to include a naturally occurring bodily opening or channel or lumen; a bodily opening or channel or lumen formed by an instrument or tool using techniques that can include, but are not limited to, mechanical, thermal, electrical, chemical, and exposure or illumination techniques; a bodily opening or channel or lumen formed by trauma to a body; or various combinations of one or more of the above. Various elements having respective openings, lumens or channels and positioned within the bodily opening (e.g., a catheter sheath) may be present in various embodiments. These elements may provide a passageway through a bodily opening for various devices employed in various embodiments.

The words "bodily cavity" as used in this disclosure should be understood to mean a cavity in a body. The bodily cavity may be a cavity provided in a bodily organ (e.g., an intra-cardiac cavity of a heart).

The word "tissue" as used in some embodiments in this disclosure should be understood to include any surface-forming tissue that is used to form a surface of a body or a surface within a bodily cavity, a surface of an anatomical feature or a surface of a feature associated with a bodily opening positioned in fluid communication with the bodily cavity. The tissue can include part or all of a tissue wall or membrane that defines a surface of the bodily cavity. In this regard, the tissue can form an interior surface of the cavity that surrounds a fluid within the cavity. In the case of cardiac applications, tissue can include tissue used to form an interior surface of an intra-cardiac cavity such as a left atrium or right atrium. In some embodiments, the word tissue can refer to a tissue having fluidic properties (e.g., blood).

The term "transducer" as used in this disclosure should be interpreted broadly as any device capable of distinguishing between fluid and tissue, sensing temperature, creating heat, ablating tissue, measuring electrical activity of a tissue surface, stimulating tissue, or any combination thereof. A transducer can convert input energy of one form into output energy of another form. Without limitation, a transducer can include an electrode that functions as, or as part of, a sensing device included in the transducer, an energy delivery device included in the transducer, or both a sensing device and an energy delivery device included in the transducer. A transducer may be constructed from several parts, which may be discrete components or may be integrally formed. In this regard, although transducers, electrodes, or both transducers and electrodes are referenced with respect to various embodiments, it is understood that other transducers or transducer elements may be employed in other embodiments. It is understood that a reference to a particular transducer in various embodiments may also imply a reference to an electrode, as an electrode may be part of the transducer as shown, e.g., with FIG. 4 discussed below.

The term "activation" as used in this disclosure should be interpreted broadly as making active a particular function as related to various transducers disclosed in this disclosure. Particular functions can include, but are not limited to, tissue ablation, sensing electrophysiological activity, sensing temperature and sensing electrical characteristics (e.g., tissue impedance). For example, in some embodiments, activation of a tissue ablation function of a particular transducer is initiated by causing energy sufficient for tissue ablation from an energy source device system to be delivered to the particular transducer. Alternatively, in this example, the activation can be deemed to be initiated when the particular transducer causes a temperature sufficient for the tissue ablation due to the energy provided by the energy source device system. Also in this example, the activation can last for a duration of time concluding when the ablation function is no longer active, such as when energy sufficient for the tissue ablation is no longer provided to the particular transducer. Alternatively, in this example, the activation period can be deemed to be concluded when the temperature caused by the particular transducer is below the temperature sufficient for the tissue ablation. In some contexts, however, the word "activation" can merely refer to the initiation of the activating of a particular function, as opposed to referring to both the initiation of the activating of the particular function and the subsequent duration in which the particular function is active. In these contexts, the phrase or a phrase similar to "activation initiation" may be used.

The term "program" in this disclosure should be interpreted as a set of instructions or modules that can be executed by one or more components in a system, such a controller system or data processing device system, in order to cause the system to perform one or more operations. The set of instructions or modules can be stored by any kind of memory device, such as those described subsequently with respect to the memory device system 130 shown in FIG. 1. In addition, this disclosure sometimes describes that the instructions or modules of a program are configured to cause the performance of a function. The phrase "configured to" in this context is intended to include at least (a) instructions or modules that are presently in a form executable by one or more data processing devices to cause performance of the function (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the function (e.g., in the case where the instructions or modules are encrypted in a non-executable manner, but through performance of a decryption process, would be translated into a form ready for execution). The word "module" can be defined as a set of instructions.

The word "device" and the phrase "device system" both are intended to include one or more physical devices or sub-devices (e.g., pieces of equipment) that interact to perform one or more functions, regardless of whether such devices or sub-devices are located within a same housing or different housings. In this regard, for example, this disclosure sometimes refers to a "catheter device", but such catheter device could equivalently be referred to as a "catheter device system".

In some contexts, the term "adjacent" is used in this disclosure to refer to objects that do not have another substantially similar object between them. For example, object A and object B could be considered adjacent if they contact each other (and, thus, it could be considered that no other object is between them), or if they do not contact each other, but no other object that is substantially similar to object A, object B, or both objects A and B, depending on context, is between them.

Further, the phrase "in response to" commonly is used in this disclosure. For example, this phrase might be used in the following context, where an event A occurs in response to the occurrence of an event B. In this regard, such phrase can include, for example, that at least the occurrence of the event B causes or triggers the event A.

Further still, example methods are described herein with respect to FIGS. 7A, 7B, 8, 9, and 10. Such figures are described to include blocks associated with instructions. It should be noted that the respective instructions associated, e.g., with each of blocks 807 and 808, or any other method blocks herein, need not be separate instructions and may be combined with other instructions to form a combined instruction set. In this regard, the blocks shown in each of the method figures herein are not intended to illustrate an actual structure of any program or set of instructions, and such method figures, according to some embodiments, merely illustrate the tasks that instructions are configured to perform upon execution by a data processing device system in conjunction with interactions with one or more other devices or device systems.

FIG. 1 schematically illustrates a system 100 for activating transducers, according to some embodiments. The system 100 includes a data processing device system 110, an input-output device system 120, and a processor-accessible memory device system 130. The processor-accessible memory device system 130 and the input-output device system 120 are communicatively connected to the data processing device system 110.

The data processing device system 110 includes one or more data processing devices that implement or execute, in conjunction with other devices, such as those in the system 100, the methods of various embodiments, including the example methods of FIGS. 7A, 7B, 8, 9, and 10 described herein. Each of the phrases "data processing device", "data processor", "processor", and "computer" is intended to include any data processing device, such as a central processing unit ("CPU"), a desktop computer, a laptop computer, a mainframe computer, tablet computer, a personal digital assistant, a cellular phone, and any other device for processing data, managing data, or handling data, whether implemented with electrical, magnetic, optical, biological components, or otherwise.

The memory device system 130 includes one or more processor-accessible memory devices configured to store information, including the information needed to execute the methods of various embodiments, including the example methods of FIGS. 7A, 7B, 8, 9, and 10 described herein. The memory device system 130 may be a distributed processor-accessible memory device system including multiple processor-accessible memory devices communicatively connected to the data processing device system 110 via a plurality of computers and/or devices. On the other hand, the memory device system 130 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. And in some embodiments, the memory device system 130 can be considered a non-transitory computer-readable storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 130 is shown separately from the data processing device system 110 and the input-output device system 120, one skilled in the art will appreciate that the memory device system 130 may be located completely or partially within the data processing device system 110 or the input-output device system 120. Further in this regard, although the input-output device system 120 is shown separately from the data processing device system 110 and the memory device system 130, one skilled in the art will appreciate that such system may be located completely or partially within the data processing system 110 or the memory device system 130, depending upon the contents of the input-output device system 120. Further still, the data processing device system 110, the input-output device system 120, and the memory device system 130 may be located entirely within the same device or housing or may be separately located, but communicatively connected, among different devices or housings. In the case where the data processing device system 110, the input-output device system 120, and the memory device system 130 are located within the same device, the system 100 of FIG. 1 can be implemented by a single application-specific integrated circuit (ASIC) in some embodiments.

The input-output device system 120 may include a mouse, a keyboard, a touch screen, another computer, or any device or combination of devices from which a desired selection, desired information, instructions, or any other data is input to the data processing device system 110. The input-output device system may include a user-activatable control system that is responsive to a user action. The input-output device system 120 may include any suitable interface for receiving information, instructions or any data from other devices and systems described in various ones of the embodiments. In this regard, the input-output device system 120 may include various ones of other systems described in various embodiments. For example, the input-output device system 120 may include at least a portion a transducer-based device system. The phrase "transducer-based device system" is intended to include one or more physical systems that include various transducers. The phrase "transducer-based device" is intended to include one or more physical devices that include various transducers.

The input-output device system 120 also may include an image generating device system, a display device system, a processor-accessible memory device, or any device or combination of devices to which information, instructions, or any other data is output by the data processing device system 110. In this regard, if the input-output device system 120 includes a processor-accessible memory device, such memory device may or may not form part or all of the memory device system 130. The input-output device system 120 may include any suitable interface for outputting information, instructions or data to other devices and systems described in various ones of the embodiments. In this regard, the input-output device system may include various other devices or systems described in various embodiments.

Various embodiments of transducer-based devices are described herein. Some of the described devices are medical devices that are percutaneously or intravascularly deployed. Some of the described devices are moveable between a delivery or unexpanded configuration (e.g., FIG. 3A, discussed below) in which a portion of the device is sized for passage through a bodily opening leading to a bodily cavity, and an expanded or deployed configuration (e.g., FIG. 3B, discussed below) in which the portion of the device has a size too large for passage through the bodily opening leading to the bodily cavity. An example of an expanded or deployed configuration is when the portion of the transducer-based device is in its intended-deployed-operational state inside the bodily cavity. Another example of the expanded or deployed configuration is when the portion of the transducer-based device is being changed from the delivery configuration to the intended-deployed-operational state to a point where the portion of the device now has a size too large for passage through the bodily opening leading to the bodily cavity.

In some example embodiments, the device includes transducers that sense characteristics (e.g., convective cooling, permittivity, force) that distinguish between fluid, such as a fluidic tissue (e.g., blood), and tissue forming an interior surface of the bodily cavity. Such sensed characteristics can allow a medical system to map the cavity, for example using positions of openings or ports into and out of the cavity to determine a position or orientation (e.g., pose), or both of the portion of the device in the bodily cavity. In some example embodiments, the described devices are capable of ablating tissue in a desired pattern within the bodily cavity.

In some example embodiments, the devices are capable of sensing characteristics (e.g., electrophysiological activity) indicative of whether an ablation has been successful. In some example embodiments, the devices are capable of providing stimulation (e.g., electrical stimulation) to tissue within the bodily cavity. Electrical stimulation may include pacing.

Figure 2:
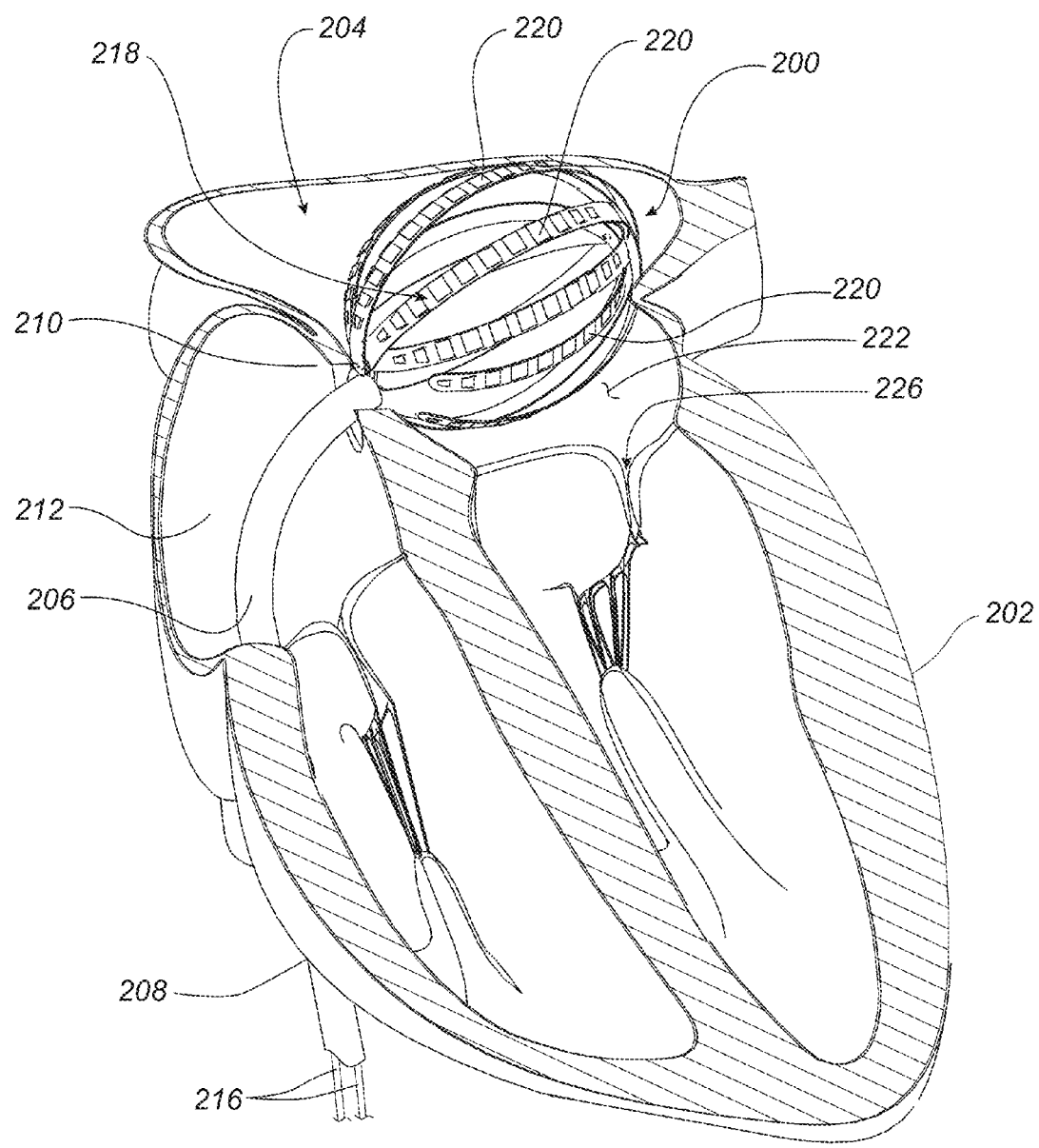
FIG. 2 illustrates a cutaway diagram of a heart showing a transducer-based device percutaneously placed in a left atrium of the heart according to various example embodiments.

FIG. 2 is a representation of a transducer-based device 200 useful in investigating or treating a bodily organ, for example a heart 202, according to one example embodiment.

Transducer-based device 200 can be percutaneously or intravascularly inserted into a portion of the heart 202, such as an intra-cardiac cavity like left atrium 204. In this example, the transducer-based device 200 is part of a catheter 206 inserted via the inferior vena cava 208 and penetrating through a bodily opening in transatrial septum 210 from right atrium 212. In other embodiments, other paths may be taken.

Catheter 206 includes an elongated flexible rod or shaft member appropriately sized to be delivered percutaneously or intravascularly. Various portions of catheter 206 may be steerable. Catheter 206 may include one or more lumens (not shown). The lumen(s) may carry one or more communications or power paths, or both. For example, the lumens(s) may carry one or more electrical conductors 216 (two shown in this embodiment). Electrical conductors 216 provide electrical connections to device 200 that are accessible externally from a patient in which the transducer-based device 200 is inserted.

Transducer-based device 200 includes a frame or structure 218 which assumes an unexpanded configuration for delivery to left atrium 204. Structure 218 is expanded (e.g., shown in a deployed or expanded configuration in FIG. 2) upon delivery to left atrium 204 to position a plurality of transducers 220 (three called out in FIG. 2) proximate the interior surface formed by tissue 222 of left atrium 204. In this example embodiment, at least some of the transducers 220 are used to sense a physical characteristic of a fluid (e.g., blood) or tissue 222, or both, that may be used to determine a position or orientation (e.g., pose), or both, of a portion of a device 200 within, or with respect to left atrium 204. For example, transducers 220 may be used to determine a location of pulmonary vein ostia (not shown) or a mitral valve 226, or both. In this example embodiment, at least some of the transducers 220 may be used to selectively ablate portions of the tissue 222. For example, some of the transducers 220 may be used to ablate a pattern around the bodily openings, ports or pulmonary vein ostia, for instance to reduce or eliminate the occurrence of atrial fibrillation.

Figure 3A:
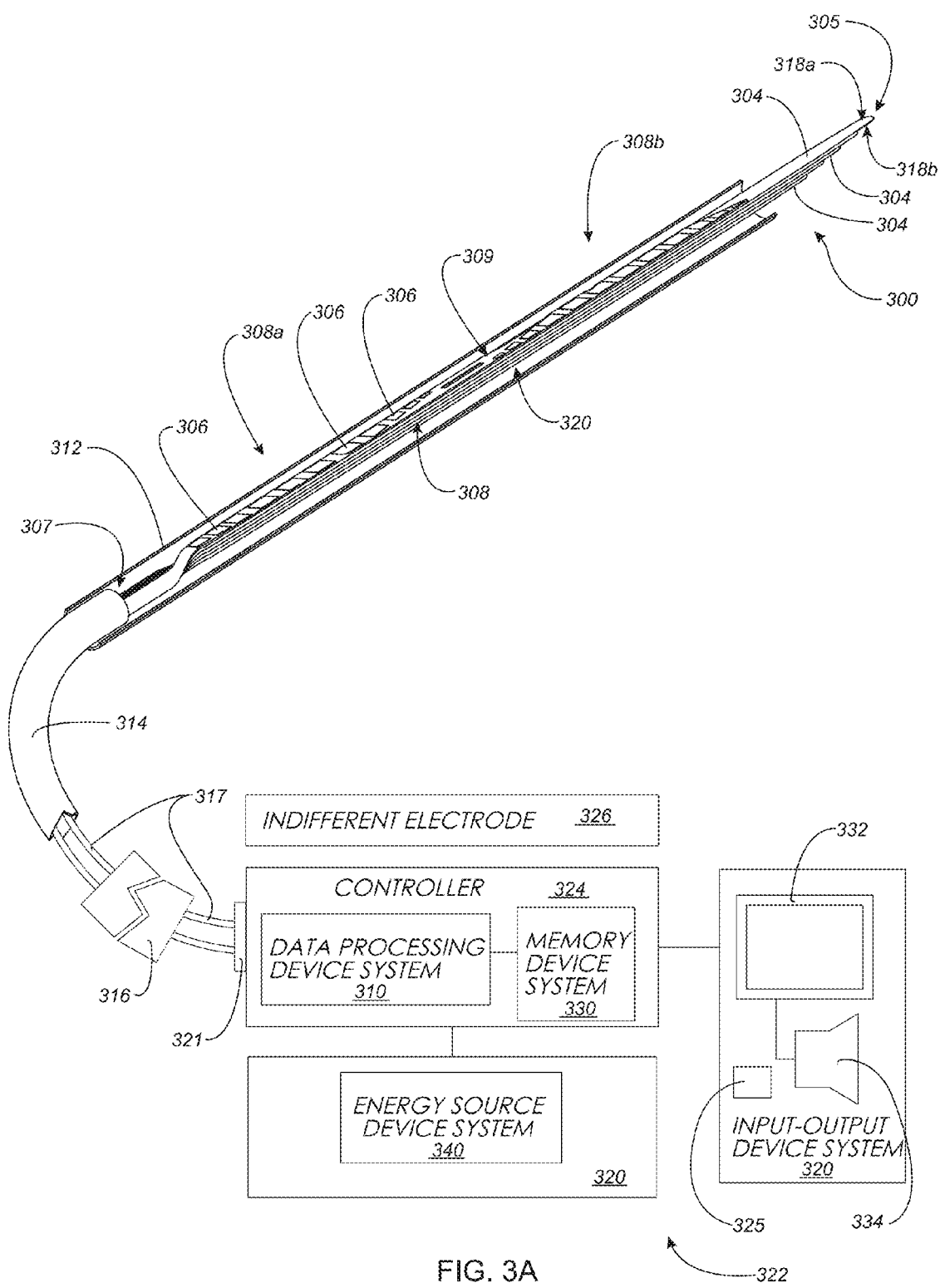
FIG. 3A illustrates a partially schematic representation of a medical system according to various example embodiments, the medical system including a data processing device system, an input-output device system, a memory device system, and a transducer-based device having a plurality of transducers and an expandable structure shown in a delivery or unexpanded configuration.
Figure 3B:
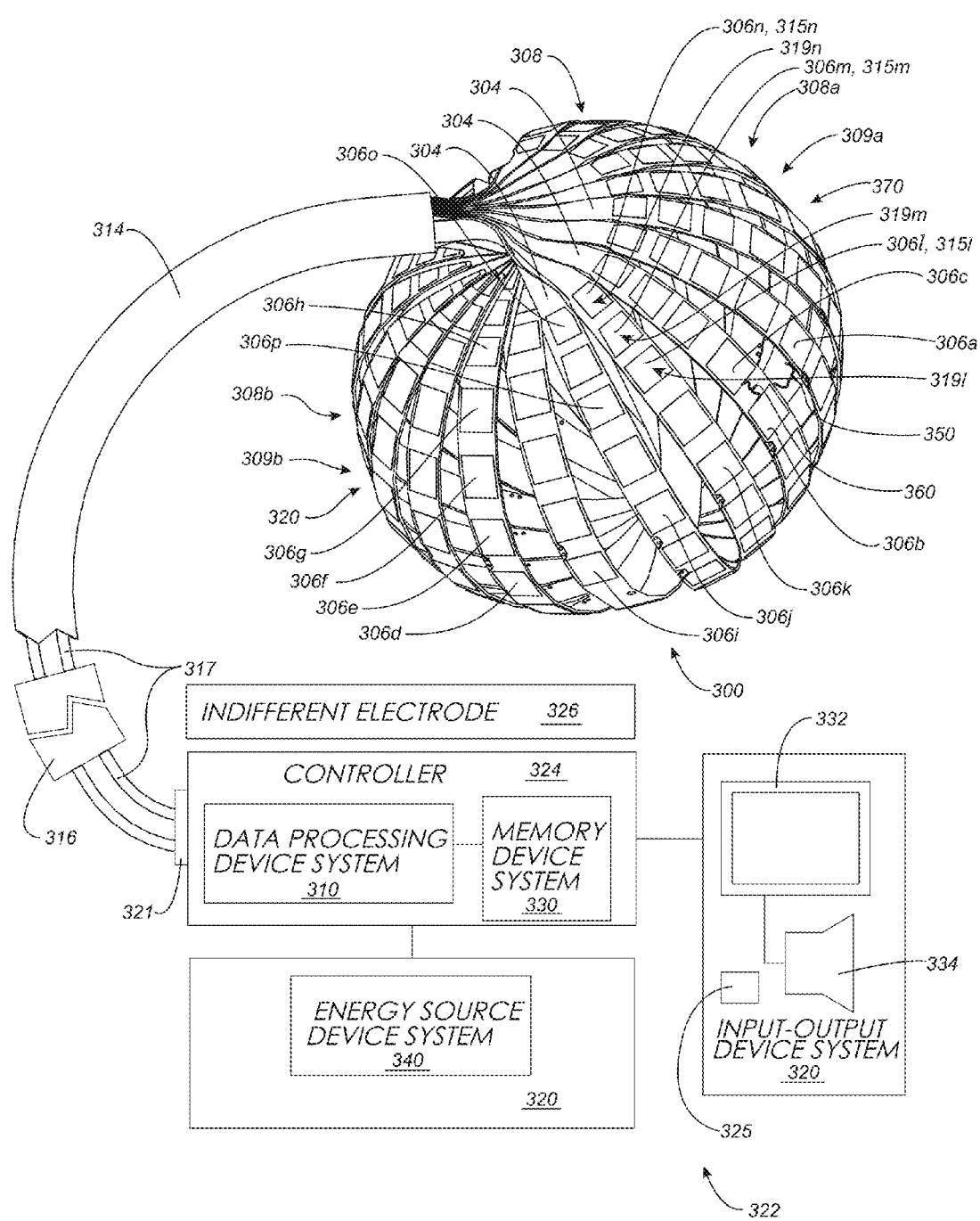
FIG. 3B illustrates the representation of the medical system of FIG. 3A with the expandable structure shown in a deployed or expanded configuration.

FIGS. 3A and 3B show a transducer-based device system (e.g., a portion thereof shown schematically) that includes a transducer-based device 300 according to one illustrated embodiment. Transducer-based device 300 includes a plurality of elongate members 304 (three called out in each of FIGS. 3A and 3B) and a plurality of transducers 306 (three called out in FIG. 3A and three called out in FIG. 3B as 306a, 306b and 306c). As will become apparent, the plurality of transducers 306 are positionable within a bodily cavity. For example, in some embodiments, the transducers 306 are able to be positioned in a bodily cavity by movement into, within, or into and within the bodily cavity, with or without a change in a configuration of the plurality of transducers 306. In some embodiments, the plurality of transducers 306 are arranged to form a two- or three-dimensional distribution, grid or array of the transducers capable of mapping, ablating or stimulating an inside surface of a bodily cavity or lumen without requiring mechanical scanning. As shown, for example, in FIG. 3A, the plurality of transducers 306 are arranged in a distribution receivable in a bodily cavity (not shown).

The elongate members 304 are arranged in a frame or structure 308 that is selectively movable between an unexpanded or delivery configuration (e.g., as shown in FIG. 3A) and an expanded or deployed configuration (i.e., as shown in FIG. 3B) that may be used to position elongate members 304 against a tissue surface within the bodily cavity or position the elongate members 304 in the vicinity of the tissue surface. In this embodiment, structure 308 has a size in the unexpanded or delivery configuration suitable for delivery through a bodily opening (e.g., via catheter sheath 312) to the bodily cavity. In this embodiment, structure 308 has a size in the expanded or deployed configuration too large for delivery through a bodily opening (e.g., via catheter sheath 312) to the bodily cavity. The elongate members 304 may form part of a flexible circuit structure (e.g., also known as a flexible printed circuit board (PCB) circuit). The elongate members 304 can include a plurality of different material layers. Each of the elongate members 304 can include a plurality of different material layers. The structure 308 can include a shape memory material, for instance Nitinol. The structure 308 can include a metallic material, for instance stainless steel, or non-metallic material, for instance polyimide, or both a metallic and non metallic material by way of non-limiting example. The incorporation of a specific material into structure 308 may be motivated by various factors including the specific requirements of each of the unexpanded or delivery configuration and expanded or deployed configuration, the required position or orientation (e.g., pose), or both of structure 308 in the bodily cavity or the requirements for successful ablation of a desired pattern.

Figure 4:
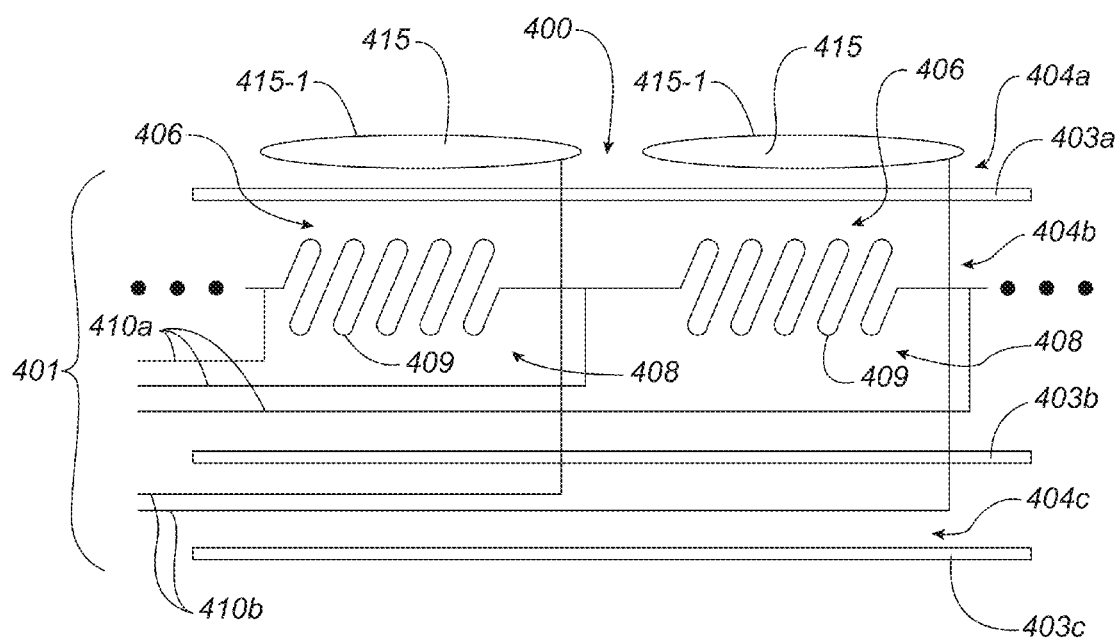
FIG. 4 illustrates a schematic representation of a transducer-based device that includes a flexible circuit structure according to various example embodiments.

FIG. 4 is a schematic side elevation view of at least a portion of a transducer-based device 400 that includes a flexible circuit structure 401 that is employed to provide a plurality of transducers 406 (two called out) according to an example embodiment. In some embodiments, the flexible circuit structure 401 may form part of a structure (e.g., structure 308) that is selectively movable between a delivery configuration sized for percutaneous delivery and expanded or deployed configurations sized too large for percutaneous delivery. In some embodiments, the flexible circuit structure 401 may be located on, or form at least part of, of a structural component (e.g., elongate member 304) of a transducer-based device system.

The flexible circuit structure 401 can be formed by various techniques including flexible printed circuit techniques. In some embodiments, the flexible circuit structure 401 includes various layers including flexible layers 403a, 403b and 403c (i.e., collectively flexible layers 403). In some embodiments, each of flexible layers 403 includes an electrical insulator material (e.g., polyimide). One or more of the flexible layers 403 can include a different material than another of the flexible layers 403. In some embodiments, the flexible circuit structure 401 includes various electrically conductive layers 404a, 404b and 404c (collectively electrically conductive layers 404) that are interleaved with the flexible layers 403. In some embodiments, each of the electrically conductive layers 404 is patterned to form various electrically conductive elements. For example, electrically conductive layer 404a is patterned to form a respective electrode 415 of each of the transducers 406. Electrodes 415 have respective electrode edges 415-1 that form a periphery of an electrically conductive surface associated with the respective electrode 415.

Electrically conductive layer 404b is patterned, in some embodiments, to form respective temperature sensors 408 for each of the transducers 406 as well as various leads 410a arranged to provide electrical energy to the temperature sensors 408. In some embodiments, each temperature sensor 408 includes a patterned resistive member 409 (two called out) having a predetermined electrical resistance. In some embodiments, each resistive member 409 includes a metal having relatively high electrical conductivity characteristics (e.g., copper). In some embodiments, electrically conductive layer 404c is patterned to provide portions of various leads 410b arranged to provide an electrical communication path to electrodes 415. In some embodiments, leads 410b are arranged to pass though vias (not shown) in flexible layers 403a and 403b to connect with electrodes 415. Although FIG. 4 shows flexible layer 403c as being a bottom-most layer, some embodiments may include one or more additional layers underneath flexible layer 403c, such as one or more structural layers, such as a steel or composite layer. These one or more structural layers, in some embodiments, are part of the flexible circuit structure 401 and can be part of, e.g., elongate member 304. In addition, although FIG. 4 shows only three flexible layers 403a-403c and only three electrically conductive layers 404a-404c, it should be noted that other numbers of flexible layers, other numbers of electrically conductive layers, or both, can be included.

In some embodiments, electrodes 415 are employed to selectively deliver RF energy to various tissue structures within a bodily cavity (not shown) (e.g., an intra-cardiac cavity). The energy delivered to the tissue structures may be sufficient for ablating portions of the tissue structures. The energy delivered to the tissue may be delivered to cause monopolar tissue ablation, bipolar tissue ablation or blended monopolar-bipolar tissue ablation by way of non-limiting example. In some embodiments, each electrode 415 is employed to sense an electrical potential in the tissue proximate the electrode 415. In some embodiments, each electrode 415 is employed in the generation of an intra-cardiac electrogram. In some embodiments, each resistive member 409 is positioned adjacent a respective one of the electrodes 415. In some embodiments, each of the resistive members 409 is positioned in a stacked or layered array with a respective one of the electrodes 415 to form a respective one of the transducers 406. In some embodiments, the resistive members 409 are connected in series to allow electrical current to pass through all of the resistive members 409. In some embodiments, leads 410a are arranged to allow for a sampling of electrical voltage in between each resistive members 409. This arrangement allows for the electrical resistance of each resistive member 409 to be accurately measured. The ability to accurately measure the electrical resistance of each resistive member 409 may be motivated by various reasons including determining temperature values at locations at least proximate the resistive member 409 based at least on changes in the resistance caused by convective cooling effects (e.g., as provided by blood flow).

Referring to FIGS. 3A, 3B, transducer-based device 300 can communicate with, receive power from or be controlled by a transducer-activation system 322. In some embodiments, elongate members 304 can form a portion of an elongated cable 316 of control leads 317, for example by stacking multiple layers, and terminating at a connector 321 or other interface with transducer-activation system 322. The control leads 317 may correspond to the electrical connectors 216 in FIG. 2 in some embodiments. The transducer-activation device system 322 may include a controller 324 that includes a data processing device system 310 (e.g., from FIG. 1) and a memory device system 330 (e.g., from FIG. 1) that stores data and instructions that are executable by the data processing device system 310 to process information received from transducer-based device 300 or to control operation of transducer-based device 300, for example activating various selected transducers 306 to ablate tissue. Controller 324 may include one or more controllers.

Transducer-activation device system 322 includes an input-output device system 320 (e.g., from FIG. 1) communicatively connected to the data processing device system 310 (e.g., via controller 324 in this embodiment). Input-output device system 320 may include a user-activatable control that is responsive to a user action. Input-output device system 320 may include one or more user interfaces or input/output (I/O) devices, for example one or more display device systems 332, speaker device systems 334, keyboards, mice, joysticks, track pads, touch screens or other transducers to transfer information to, from, or both to and from a user, for example a care provider such as a physician or technician. For example, output from a mapping process may be displayed on a display device system 332. Input-output device system 320 may include a sensing device system 325 configured to detect various characteristics including, but not limited to, at least one of tissue characteristics (e.g., electrical characteristics such as tissue impedance, tissue type, tissue thickness) and thermal characteristics such as temperature. In this regard, the sensing device system 325 may include one, some, or all of the transducers 306 (or 406 of FIG. 4) of the transducer based device 300, including the internal components of such transducers shown in FIG. 4, such as the electrodes 315 and temperature sensors 408.

Transducer-activation device system 322 may also include an energy source device system 340 including one or more energy source devices connected to transducers 306. In this regard, although FIG. 3A shows a communicative connection between the energy source device system 340 and the controller 324 (and its data processing device system 310), the energy source device system 340 may also be connected to the transducers 306 via a communicative connection that is independent of the communicative connection with the controller 324 (and its data processing device system 310). For example, the energy source device system 340 may receive control signals via the communicative connection with the controller 324 (and its data processing device system 310), and, in response to such control signals, deliver energy to, receive energy from, or both deliver energy to and receive energy from one or more of the transducers 306 via a communicative connection with such transducers 306 (e.g., via one or more communication lines through catheter body 314, elongated cable 316 or catheter sheath 312) that does not pass through the controller 324. In this regard, the energy source device system 340 may provide results of its delivering energy to, receiving energy from, or both delivering energy to and receiving energy from one or more of the transducers 306 to the controller 324 (and its data processing device system 310) via the communicative connection between the energy source device system 340 and the controller 324.

In any event, the number of energy source devices in the energy source device system 340 is fewer than the number of transducers in some embodiments. The energy source device system 340 may, for example, be connected to various selected transducers 306 to selectively provide energy in the form of electrical current or power (e.g., RF energy), light or low temperature fluid to the various selected transducers 306 to cause ablation of tissue. The energy source device system 340 may, for example, selectively provide energy in the form of electrical current to various selected transducers 306 and measure a temperature characteristic, an electrical characteristic, or both at a respective location at least proximate each of the various transducers 306. The energy source device system 340 may include as its energy source devices various electrical current sources or electrical power sources. In some embodiments, an indifferent electrode 326 is provided to receive at least a portion of the energy transmitted by at least some of the transducers 306. Consequently, although not shown in FIG. 3A, the indifferent electrode 326 may be communicatively connected to the energy source device system 340 via one or more communication lines in some embodiments. In addition, although shown separately in FIG. 3A, indifferent electrode 326 may be considered part of the energy source device system 340 in some embodiments.

It is understood that input-output device system 320 may include other systems. In some embodiments, input-output device system 320 may optionally include energy source device system 340, transducer-based device 300 or both energy source device system 340 and transducer-based device 300 by way of non-limiting example. Input-output device system 320 may include the memory device system 330 in some embodiments.

Structure 308 can be delivered and retrieved via a catheter member, for example a catheter sheath 312. In some embodiments, a structure provides expansion and contraction capabilities for a portion of the medical device (e.g., an arrangement, distribution or array of transducers 306). The transducers 306 can form part of, be positioned or located on, mounted or otherwise carried on the structure and the structure may be configurable to be appropriately sized to slide within catheter sheath 312 in order to be deployed percutaneously or intravascularly. FIG. 3A shows one embodiment of such a structure. In this example embodiment, each of the elongate members 304 includes a respective distal end 305 (only one called out), a respective proximal end 307 (only one called out) and an intermediate portion 309 (only one called out) positioned between the proximal end 307 and the distal end 305. The respective intermediate portion 309 of each elongate member 304 includes a first or front surface 318a that is positionable to face an interior tissue surface within a bodily cavity (not shown) and a second or back surface 318b opposite across a thickness of the intermediate portion 309 from the front surface 318a. In some embodiments, each of the elongate members 304 is arranged front surface 318a-toward-back surface 318b in a stacked array during an unexpanded or delivery configuration similar to that described in co-assigned International Application No.: PCT/US2012/022061 and co-assigned International Application No: PCT/US2012/022062, both of which are hereby incorporated herein by reference in their entirety. In many cases a stacked array allows the structure 308 to have a suitable size for percutaneous or intravascular delivery. In this embodiment, the elongate members 304 are arranged to be introduced into a bodily cavity (again not shown) distal end 305 first. For clarity, not all of the elongate members 304 of structure 308 are shown in FIG. 3A. A flexible catheter body 314 is used to deliver structure 308 through catheter sheath 312.

In a manner similar to that described in co-assigned International Application No.: PCT/US2012/022061 and co-assigned International Application No.: PCT/US2012/022062, each of the elongate members 304 is arranged in a fanned arrangement 370 in FIG. 3B. In this embodiment, the fanned arrangement 370 is formed during the expanded or deployed configuration in which structure 308 is manipulated to have a size too large for percutaneous or intravascular delivery. In this example embodiment, structure 308 includes a proximal portion 308a having a first domed shape 309a and a distal portion 308b having a second domed shape 309b. In this example embodiment, the proximal and the distal portions 308a, 308b include respective portions of elongate members 304. In this example embodiment, the structure 308 is arranged to be delivered distal portion 308b first into a bodily cavity (again not shown) when the structure is in the unexpanded or delivery configuration as shown in FIG. 3A. In this example embodiment, the proximal and the distal portions 308a, 308b are arranged in a clam shell configuration in the expanded or deployed configuration shown in FIG. 3B.

The transducers 306 can be arranged in various distributions or arrangements in various embodiments. In this example embodiment, various ones of the transducers 306 are spaced apart from one another in a spaced apart distribution in the delivery configuration shown in FIG. 3A. In this example embodiment, various ones of the transducers 306 are arranged in a spaced apart distribution in the deployed configuration shown in FIG. 3B. In this example embodiment, various pairs of transducers 306 are spaced apart with respect to one another. In this example embodiment, various regions of space are located between various pairs of the transducers 306. For example, in FIG. 3B the transducer-based device 300 includes at least a first transducer 306a, a second transducer 306b and a third transducer 306c (all collectively referred to as transducers 306). In this example embodiment each of the first, the second and the third transducers 306a, 306b and 306c are adjacent transducers in the spaced apart distribution. In this example embodiment, the first and the second transducers 306a, 306b are located on different elongate members 304 while the second and the third transducers 306b, 306c are located on a same elongate member 304. In this example embodiment, a first region of space 350 is between the first and the second transducers 306a, 306b. In this example embodiment, the first region of space 350 is not associated with any physical portion of structure 308. In this example embodiment, a second region of space 360 associated with a physical portion of device 300 (e.g., a portion of an elongate member 304) is between the second and the third transducers 306b, 306c. In this example embodiment, each of the first and the second regions of space 350, 360 does not include a transducer of transducer-based device 300. In this example embodiment, each of the first and the second regions of space 350, 360 does not include any transducer. It is noted that other embodiments need not employ a group of elongate members 304 as employed in the illustrated embodiment. For example, other embodiments may employ a structure having a one or more surfaces, at least a portion of the one or more surfaces defining one or more openings in the structure. In these embodiments, a region of space not associated with any physical portion of the structure may extend over at least part of an opening of the one or more openings. In other example embodiments, other structures may be employed to support or carry transducers of a transducer-based device such as a transducer-based catheter. For example, an elongated catheter member may be used to distribute the transducers in a linear or curvilinear array. Basket catheters or balloon catheters may be used to distribute the transducers in a two-dimensional or three-dimensional array.

Figure 7A:
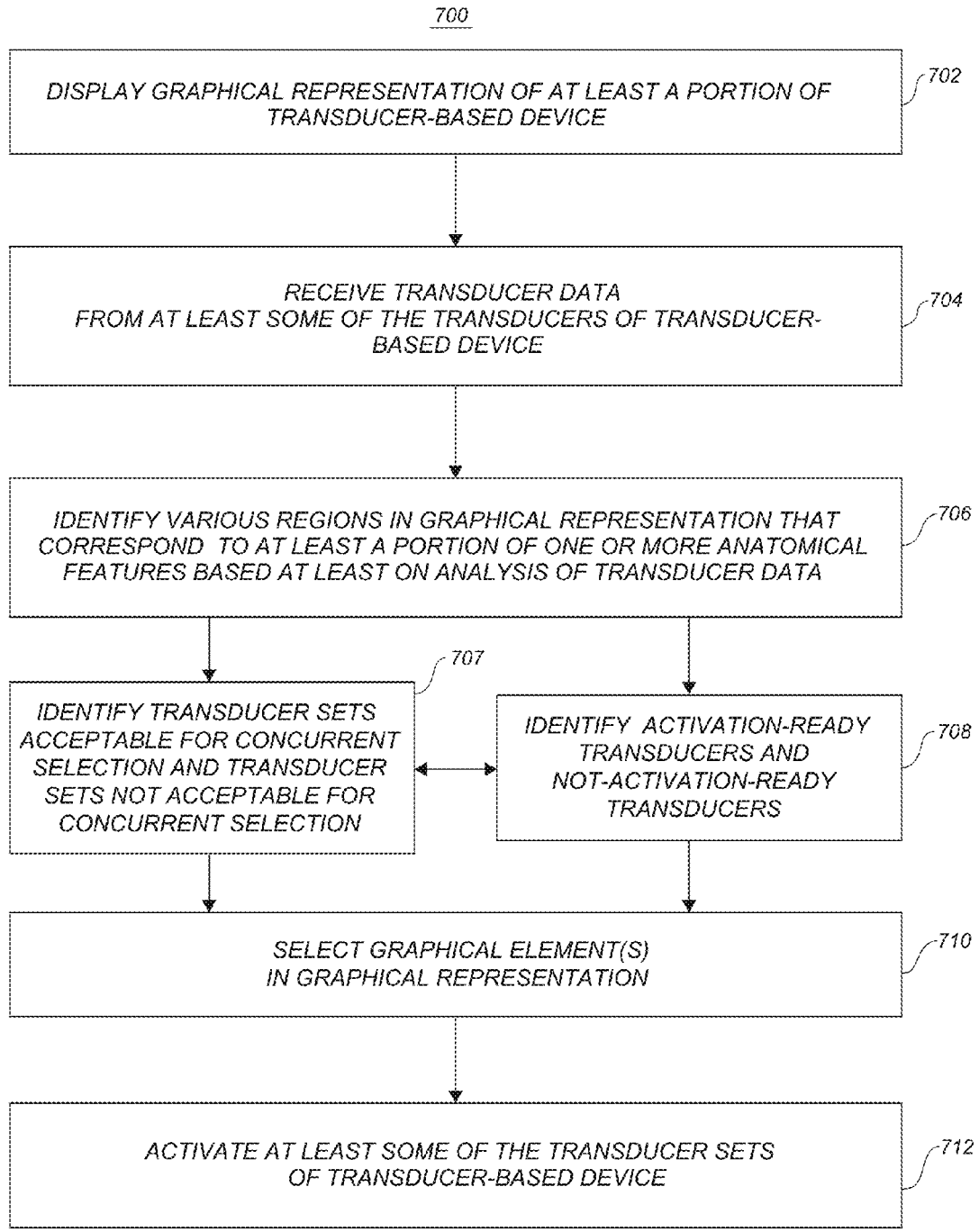
FIG. 7A illustrates a block diagram of a method for activating transducers of a transducer-based device according to some example embodiments.

FIG. 7A is a block diagram of a method 700 employed according to some example embodiments. In various example embodiments, a memory device system (e.g., memory device systems 130, 330) is communicatively connected to a data processing device system (e.g., data processing device systems 110 or 310) and stores a program executable by the data processing device system to cause the data processing device system to execute method 700 via interaction with at least, for example, a transducer-based device (e.g., transducer-based devices 200, 300, or 400). In these various embodiments, the program may include instructions configured to perform, or cause to be performed, various ones of the instructions associated with method 700. In some embodiments, method 700 may include a subset of the associated blocks or additional blocks than those shown in FIG. 7A. In some embodiments, method 700 may include a different sequence between various ones of the associated blocks than those shown in FIG. 7A.

Figure 5A:
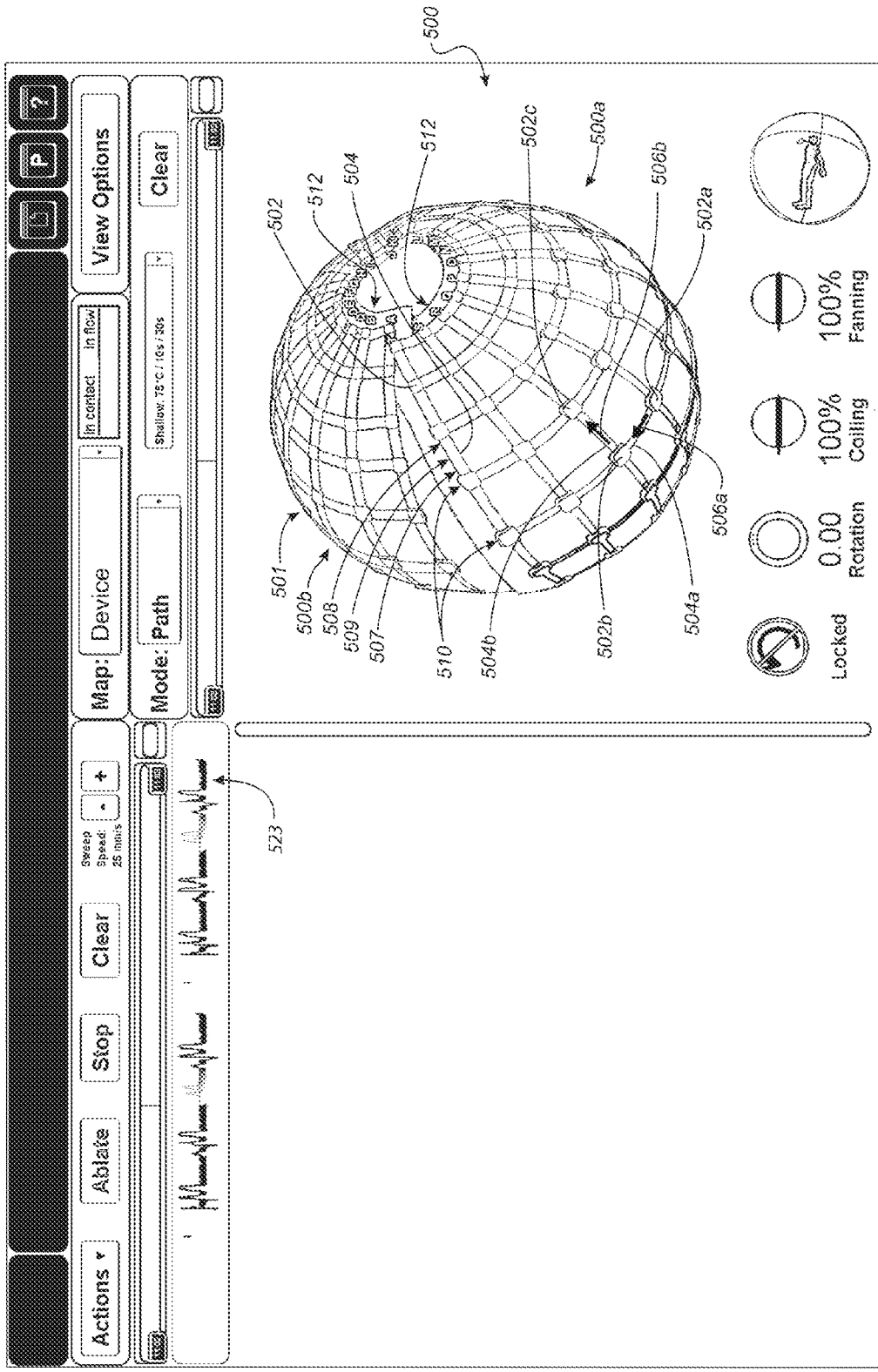
FIG. 5A illustrates a graphical interface providing a graphical representation of at least a portion of a transducer-based device according to various example embodiments, the graphical representation including a plurality of graphical elements including a plurality of transducer graphical elements and a plurality of between graphical elements.

Block 702 includes instructions (e.g., graphical representation instructions or graphical interface instructions provided by a program) configured to cause an input-output device system (e.g., input-output device system 120 or 320) to display a graphical representation of at least a portion of a transducer-based device. For example, FIG. 5A illustrates a graphical interface including a graphical representation 500 provided by the input-output device system according to one example embodiment provided in accordance with block 702. In this embodiment, the transducer-based device is a catheter-based device similar to devices 200 and 300 shown respectively in FIGS. 2 and 3. In this example embodiment, the graphical interface depicts graphical representation 500 of the transducer-based device as including a first domed portion 500a associated with a first domed portion of the transducer-based device (e.g., proximal portion 308a when having the first domed shape 309a) and a second domed portion 500b associated with a second domed portion of the transducer-based device (e.g., distal portion 308b having the second domed shape 309b). Various other transducer-based devices may be depicted in other embodiments. FIGS. 5A, 5B, 5C, 5D, 5E, 5F, 5G, 5H, 5I and 5J (collectively FIG. 5) are presented in this disclosure in association with various different embodiments. It is understood that each of the different embodiments need not be associated with all of the FIG. 5, and in some cases will only be associated with a subset of the FIG. 5.

In this embodiment, the graphical representation 500 includes a plurality of graphical elements 501. Each of the graphical elements 501 is respectively associated with a respective one of a plurality of transducer sets. Each respective transducer set includes at least one of a plurality of transducers included as part of the transducer-based device (e.g., transducer-based devices 200, 300, or 400) and each respective transducer set has at least one different transducer than another of the other transducer sets. In this particular embodiment, each respective transducer set has at least one different transducer than each of the others of the other transducer sets.

In this example embodiment, each of at least some of the graphical elements 501 are provided by a respective one of a plurality of transducer graphical elements 502 that include at least a first transducer graphical element 502a, a second transducer graphical element 502b, and a third transducer graphical element 502c (e.g., all the transducer graphical elements collectively referred to as transducer graphical elements 502). In this example embodiment, each transducer graphical element 502 is associated with a single respective transducer of the transducer-based device. In some example embodiments, each transducer graphical element 502 is representative of a respective transducer of the transducer-based device. In some example embodiments, each transducer graphical element 502 is representative of a location or position of a respective transducer of the transducer-based device. In this example embodiment, the graphical representation 500 includes a first spatial relationship between the transducer graphical elements 502 that is consistent with a second spatial relationship between the corresponding transducers associated with the transducer graphical elements 502. An electrocardiogram (ECG/EKG) signal 523 is also shown in the graphical interface of FIG. 5A.

In this example embodiment, each of at least some of the graphical elements 501 are provided by a respective one of a plurality of between graphical elements 504 including a first between graphical element 504a and a second between graphical element 504b (e.g., all the between graphical elements collectively referred to as between graphical elements 504). In various embodiments, each of the between graphical elements 504 is associated with a set of at least two of the transducers of the transducer-based device. In some example embodiments, each of the between graphical elements 504 is associated with a pair of transducers in the transducer-based device. In some example embodiments, each between graphical element 504 is associated with a region of space between a respective pair of transducers in the transducer-based device. In some example embodiments, each between graphical element 504 is associated with a region of space between a respective pair of adjacent ones of the transducers in the transducer-based device.

In this example embodiment, first transducer graphical element 502a is associated with a first transducer (e.g., first transducer 306a) of the transducer-based device, second transducer graphical element 502b associated with a second transducer (e.g., second transducer 306b) of the transducer-based device, and third transducer graphical element 502c associated with a third transducer (e.g., third transducer 306c) of the transducer-based device. In this example embodiment, the first between graphical element 504a is associated with a first region of space that is between the first and the second transducers and the second between graphical element 504b is associated with a second region of space that is between the second and the third transducers. In this illustrated embodiment, the first region of space is a region of space that is not associated with any physical part of the transducer-based device (e.g., first region of space 350) and the second region of space is a region of space that is associated with a physical part of the transducer-based device (e.g., second region of space 360). In this example embodiment, each of the first and the second between graphical elements 504a, 504b is associated with a region of space that does not include a transducer of the transducer-based device. In this example embodiment, each of the first and the second between graphical elements 504a, 504b is associated with a region of space that does not include any transducer. It is understood that a "region of space" need not be a vacant space but can include physical matter therein.

In this example embodiment, the second transducer graphical element 502b is depicted in a first direction (e.g., represented by arrow 506a) from the first transducer graphical element 502a, and the first between graphical element 504a is positioned between the second and the first transducer graphical elements 502b, 502a in the graphical representation. In this example embodiment, the third transducer graphical element 502c is depicted in a second direction (e.g., represented by arrow 506b) from the second transducer graphical element 502b, and the second between graphical element 504b is positioned between the second and the third transducer graphical elements 502b, 502c. In this example embodiment, the first and the second directions are non-parallel to each other. In this example embodiment, the first between graphical element 504a is formed, at least in part, at a location in the graphical representation intersected by the first direction from the first graphical transducer element 502a and the second between graphical element 504b is formed, at least in part at a location in the graphical representation intersected by the second direction from the second transducer graphical element 502b. In other example embodiments, other spatial relationships exist between the transducer graphical elements 502 and the between graphical elements 504 in the graphical representation. It is understood that arrows 506a, 506b do not form part of the graphical representation in this embodiment.

Figure 6:
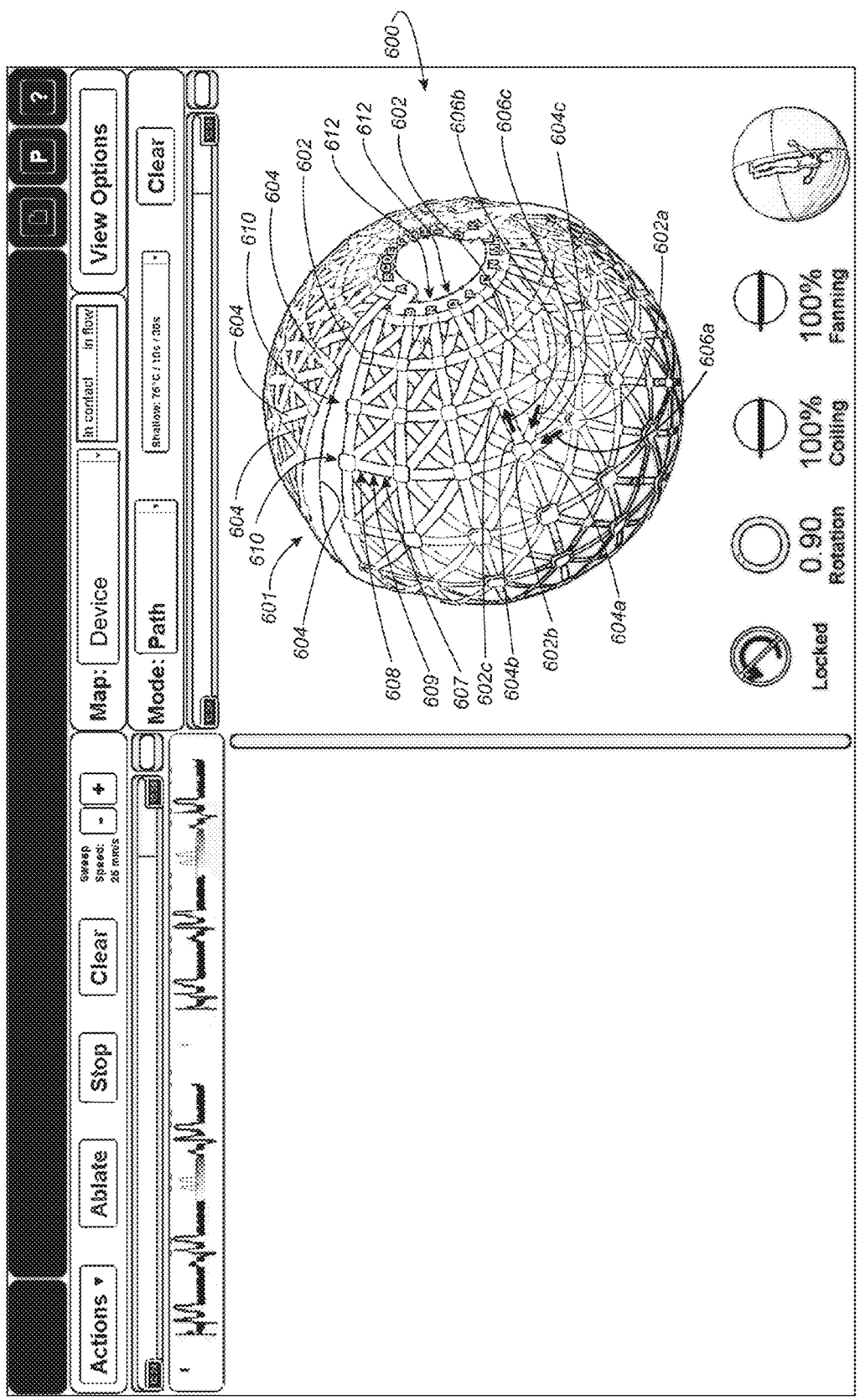
FIG. 6 illustrates a graphical interface providing a graphical representation of at least a portion of a transducer-based device according to various example embodiments.

In this example embodiment, each of the between graphical elements 504 includes a first end 507 (only one called out), a second end 508 (only one called out) and an elongate portion 509 (only one called out) extending between the first and the second ends 507, 508. The transducer graphical elements 502, the between graphical elements 504, or both may have different sizes, shapes or forms than those shown in the illustrated embodiment. In some embodiments, different ones of the transducer graphical elements 502 may be depicted with different shapes, sizes or forms in the graphical representation. In some embodiments, different ones of the between graphical elements 504 may be depicted with different shapes, sizes or forms in the graphical representation. In this embodiment, the respective elongate portion 509 of the first between graphical element 504a is depicted extending along the first direction (e.g., again represented by arrow 506a) and the respective elongate portion 509 of the second between graphical element 504b is depicted extending along the second direction (e.g., again represented by arrow 506b). In this example embodiment the first direction is depicted generally orthogonal to the second direction in the three-dimensional graphical representation. Other orientations between the first and the second direction are possible in other embodiments. For example, FIG. 6 illustrates a graphical interface including a graphical representation 600 provided by an input-output device system (e.g., input-output device system 120 or 320) according to another example embodiment. In a manner similar to FIG. 5A, the graphical interface of FIG. 6 provides a graphical representation 600 that includes a plurality of graphical elements 601, each of the graphical elements 601 associated with a respective one of a plurality of transducer sets. Each respective transducer set includes at least one of a plurality of the transducers included as part of the transducer-based device and each respective transducer set has at least one different transducer than another of the other transducer sets. In this particular embodiment, each respective transducer set has at least one different transducer than each of the others of the other transducer sets.

In a manner similar to the embodiment of FIG. 5A, the plurality of graphical elements 601 include a plurality of transducer graphical elements 602 (e.g., including transducer graphical elements 602a, 602b and 602c) and a plurality of between graphical elements 604. In a manner similar to the embodiment of FIG. 5A, each of the transducer graphical elements 602 is associated with a transducer of a transducer-based device and each of the between graphical elements 604 is associated with a region of space between a pair of transducers of a transducer based-device. In a manner similar to the embodiment of FIG. 5A, each of at least some of the between graphical elements (e.g., first between graphical element 604a and a third between graphical element 604c) is associated with a respective region of space that is not associated with any physical part of the transducer-based device. In a manner similar to the embodiment shown in FIG. 5A, each of at least some of the between graphical elements (e.g., second between graphical elements 604b) is associated with a respective region of space that is associated with a physical portion of the transducer-based device (e.g., an elongate member 304). In a manner similar to the embodiment shown in FIG. 5A, each of the between graphical elements 604 includes a first end 607 (only one called out), a second end 608 (only one called out) and an elongate portion 609 (only one called out) extending between the first and the second ends 607, 608. In this example embodiment, the respective elongate portion 609 of each of two of first ones of the between graphical element (e.g., between graphical elements 604a, 604b) is depicted extending along a respective first direction (e.g., represented by respective ones of arrows 606a, 606b), and the respective elongate portion 609 of a second one of the between graphical elements 604 (e.g., between graphical element 604c) is depicted extending along a second direction (e.g., represented by arrow 606c). In this example embodiment, the second direction is oblique to each of the first directions.

In this example embodiment, the second direction forms an acute angle with respect to each of the first directions. In this illustrated embodiment, each between graphical element 604 is associated with a region of space that does not include a transducer of a transducer-based device. In this illustrated embodiment, each between graphical element 604 is associated with a region of space that does not include any transducer.

Referring back to FIG. 5A, at least a portion of the transducer graphical elements 502, and at least a portion of the between graphical elements 504 are arranged in a plurality of rows 510 (two called out) and a plurality of columns 512 (two called out, each column 512 identified in the graphical representation by a respective one of letters "A", "B", "C", "D", "E", "F", "G", "H", "I", "J", "K", "L", "M", "N", "O", "P", "Q", "R", "S", and "T"). In this example embodiment, a portion of each of the columns 512 corresponds to region of space associated with a physical portion of the transducer-based device (e.g., an elongate member 304). In this example embodiment, each of the columns 512 corresponds to at least a portion of the transducers located on a particular elongate member of a transducer-based device (e.g., an elongate member 304). In this example embodiment, each of the columns 512 corresponds to at least a portion of the transducers located on a respective one of a pair of domed portions arranged in a clam shell configuration similar to the embodiments of FIG. 3B. In embodiments in which each domed portion is formed by a respective portion of each of a plurality of elongate members (e.g., elongate members 304), a set of two or more of the columns 512 may correspond to the transducers located on a single one of the elongate members.

In this example embodiment, a portion of each of the rows 510 corresponds to regions of space not associated with any physical portion of the transducer-based device (e.g., regions of space 350 between adjacent ones of the elongate members 304). In other example embodiments, different numbers of transducer graphical elements 502 and different numbers and spatial arrangements of between graphical elements 504 may be depicted in the graphical representation. In other example embodiments, different numbers and spatial arrangements of rows 510 and columns 512 may be depicted in the graphical representation. In various embodiments, each of the between graphical elements (e.g., between graphical elements 504, 604) depicted in the graphical representation are representative of a respective physical path extending between a respective pair of transducers of the transducer-based device. Each of the physical paths may extend over a physical surface of the transducer-based device or over a portion of an opening defined by a physical surface of the transducer-based device. In the embodiment shown in FIG. 6, each between graphical element 604 is representative of a respective physical path extending between the respective transducers associated with the adjacent pair of transducer graphical elements 602 that the between graphical element 604 extends between. In the embodiment shown in FIG. 6, each adjacent pair of the transducer graphical elements 602 may be provided along a row 610 (two called out) of the graphical elements 601, along a column 612 (two called out) of the graphical elements 601, or diagonally between a row 610 and a column 612.

Referring back to FIG. 5A, the transducer graphical elements 502 and the between graphical elements 504 in each respective one of the rows 510 are interleaved with respect to one another along the respective one of the rows 510. In this illustrated embodiment, the transducer graphical elements 502 and the between graphical elements 504 in each respective one of the columns 512 are interleaved with respect to one another along the respective one of the columns 512. In this illustrated embodiment, each one of the plurality of columns 512 shares a same transducer graphical element 502 with one of the plurality of rows 510. In this illustrated embodiment, each respective one of the plurality of columns 512 excludes any of the between graphical elements 504 included in each of the plurality of rows 510. In this illustrated embodiment, at least a first one of the between graphical elements 504 (e.g., second between graphical element 504b) is depicted in the graphical representation between two adjacent ones of the plurality of rows 510 and at least a second one of the plurality of between graphical elements 504 (e.g., first between graphical element 504a) is positioned between two adjacent ones of the plurality of columns 512. In this example embodiment, the plurality of rows 510 and the plurality of columns 512 are depicted as a three-dimensional arrangement in the graphical representation. In this example embodiment, at least two of the plurality of columns 512 are depicted in the graphical representation extending along respective directions that converge with respect to one another. In this illustrated embodiment, at least two of the plurality of columns 512 are depicted in the graphical representation extending along non-parallel directions and at least two of the plurality of rows 510 are depicted extending along parallel directions. In this illustrated embodiment, the rows 510 and the columns 512 are depicted in the graphical representation in an arrangement in which the columns 512 are circumferentially arranged. In this illustrated embodiment, the rows 510 and the columns 512 are depicted in the graphical representation in an arrangement having a generally spherical shape. In this illustrated embodiment, the respective first end 507 and the respective second end 508 of each of at least some of the plurality of between graphical elements 504 connects to a transducer graphical element 502 in the graphical representation. The transducer graphical elements 602 and a portion of the between graphical elements 604 in the embodiment of FIG. 6 are arranged in a similar manner to the embodiment shown in FIG. 5A. In the embodiment of FIG. 6, at least some of the between graphical elements 604 extend along respective directions that form acute angles with the respective directions extended along by others of the between graphical elements 604. In the embodiment of FIG. 6, at least some of the between graphical elements 604 extend along respective directions that form acute angles with the respective directions extended along by a row 610 or a column 612.

Figure 5B:
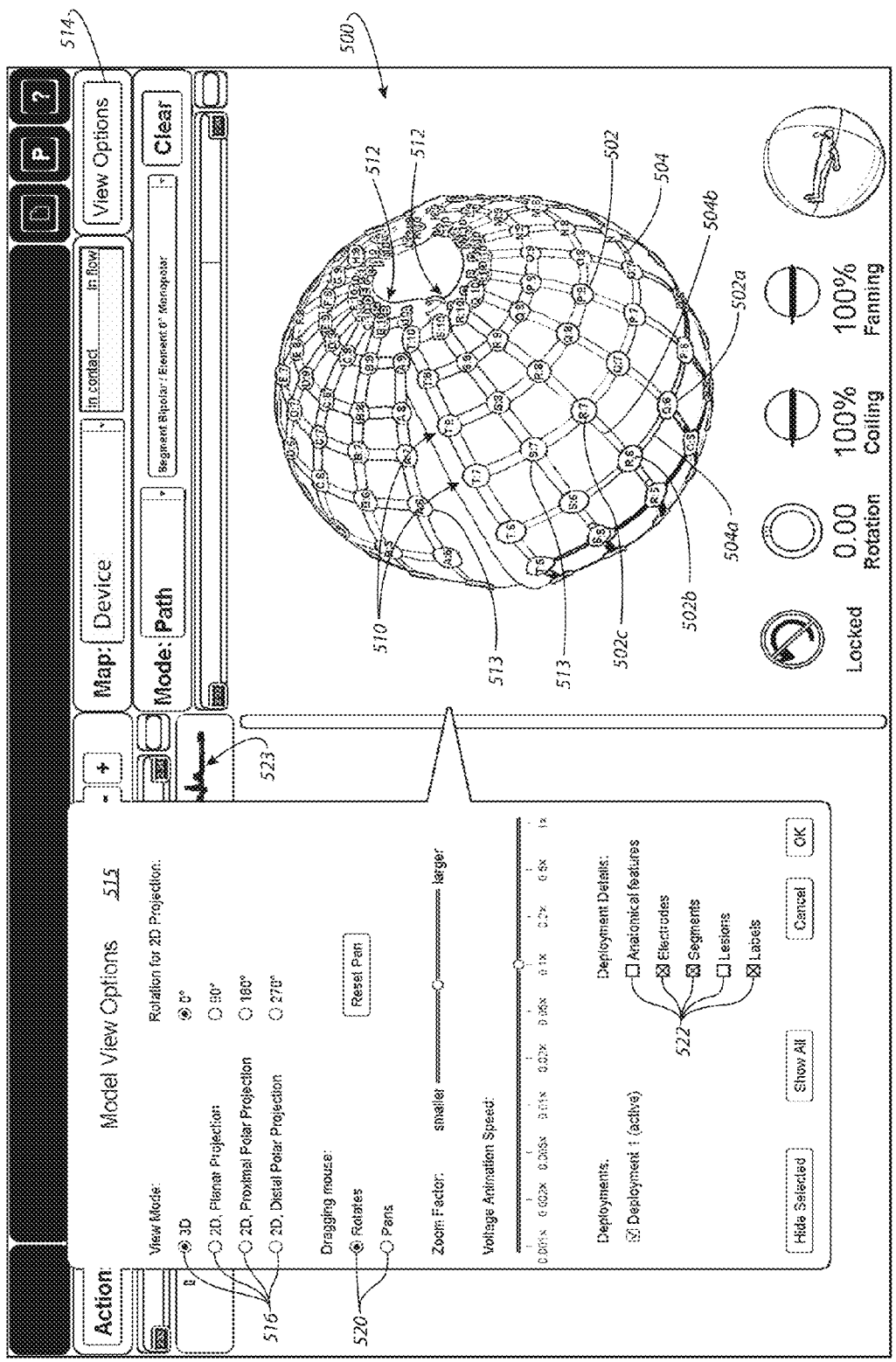
FIG. 5B illustrates the graphical representation provided by the graphical interface of FIG. 5A with at least some of the transducer graphical elements identified by identification labels.

The graphical interface of FIG. 5B includes the graphical representation 500 with the addition of identification labels 513 (two called out) to each of the transducer graphical elements 502. In this example embodiment identification labels are applied by operating the input-output device system to activate a control button 514 identified as "View Options". Selection, activation, or both selection and activation of a control button, a selection box or other graphical element provided in the various embodiments may be accomplished via various input-output device system controls that can include a touch screen, keyboard or computer mouse by way of non-limiting example. In this embodiment, selection of control button 514 causes the selection menu 515 identified as "Model View Options" to appear in the graphical representation. Selection menu 515 provides various selection boxes 516 that are selectable to vary the graphical representation of the portion of the transducer-based device between a three-dimensional representation (e.g., as depicted in FIGS. 5A and 5B) and a two dimensional representation (e.g., as depicted in FIG. 5D). Various two-dimensional representations are possible in various embodiments. For example, the two-dimensional representation depicted in FIG. 5D is shown in a "Mercator-type" representation in which the first domed portion 500a (e.g., shown in FIG. 5A) of the depicted transducer-based device is depicted as first Mercator projection 518a and the second domed portion 500b (e.g., shown in FIG. 5A) of the depicted transducer-based device is a depicted as a second Mercator projection 518b. The first and the second Mercator projections 518a and 518b advantageously allow for simultaneous viewing of all the transducer graphical elements 502 and the between graphical elements 504. Other two-dimensional representations including polar projections are also selectable.

Selection menu 515 provides various selection boxes 520 that can control mouse drag functions between rotating and panning modes. A rotating mode may be advantageously used for manipulation of a three-dimensional representation of the transducer-based device to allow for viewing a portion of the three-dimensional representation that was not previously viewable. Selection menu 515 includes a plurality of selection boxes 522 that allow for variations in the viewable content of the graphical representation. In this embodiment, a selection box 522 allows for the selective inclusion in the graphical representation of graphical elements associated with various anatomical features. In some example embodiments, the graphical elements associated with the anatomical features are selectable from a menu and may be tailored to a particular procedure in which the transducer-based device is employed. Various ones of the selection boxes 522 allow for selective inclusions of the transducer graphical elements 502 (e.g., indicated as "Electrodes" in this illustrated embodiment) and the selective inclusion of the between graphical elements 504 (e.g., indicated as "Segments" in this illustrated embodiment). In this embodiment, a selection box 522 allows for the selective inclusion in the graphical representation of graphical elements associated with lesions which may be of particular interest in embodiments in which various transducers of the transducer based-device ablate tissue to form the lesions therein.

In this example embodiment, a selection box 522 allows for the selective inclusion of identification labels 513 (e.g., indicated as "Labels" in this illustrated embodiment). In this example embodiment, each of the identification labels 513 is employs an alpha-numeric format including a letter representative of the column 512 in which a corresponding transducer graphical element is located and a number representative of a location of the transducer graphical element 502 in the corresponding column 514. Other identification schemes may be employed in other embodiments.

Having described examples of the graphical representation displayed according to the instructions of block 702 in FIG. 7A, the selection of one or more graphical elements in the graphical representation according to some embodiments will now be described with respect to block 710 in FIG. 7A. Accordingly, although FIG. 7A shows block 710 located after blocks 707 and 708, the invention is not limited to this arrangement, and the selection of one or more graphical elements according to block 710 can occur at any time the graphical elements are selectable, such as when they are displayed in the graphical representation displayed according to block 702. Blocks 704, 706, 707, and 708 in FIG. 7A are described afterwards.

In this regard, the selection according to the instructions of block 710 includes, in some embodiments, multiple constituent or sub-selections (although in other embodiments, the selection according to the instructions of block 710 includes only a single selection). For instance, in some embodiments, block 710 includes selection instructions configured to cause, due to execution of the selection instructions by the data processing device system (e.g., exemplified by data processing device systems 110 or 310), selection of a graphical element. In some embodiments, such selection instructions include a first group of instructions configured to cause the data processing device system to receive or process, via the input-output device system, a user instruction to select a graphical element. In some of these embodiments, such selection instructions also include a second group of instructions configured to cause the data processing device system to perform its own selection of the graphical element in response to receiving the user instruction. For instance, the user instruction to select the graphical element might originate from a user clicking a mouse button (e.g., a first constituent selection) while a cursor is above a user-selected graphical element. In this case, the first group of instructions could configure the data processing device system to recognize this user instruction when it is received via the data input-output device system as a user instruction to select the user-selected graphical element below the cursor at the time of the mouse-button click. In some embodiments, the second group of instructions may configure the data processing device system, in response to the first group of instructions recognizing this user instruction, to perform its own selection (e.g., a second constituent selection) of the user-selected graphical element at least by causing, via the input output device system, the display of the user-selected graphical element to change one or more visual characteristics of the user-selected graphical element. Accordingly, the selection according to the instructions of block 710 may be deemed, in some embodiments, to involve a first, user-based constituent selection and a second, machine-based or automatic constituent selection triggered by the user-based constituent selection.

Although a mouse-click was provided above as an example of a user-based constituent selection, and the changing of a visual characteristic of the user-selected graphical element was provided as an example of a machine-based constituent selection, it should be noted, however, that any form of user-based selection or machine-based selection of a graphical element known in the art can be used. In this regard, direct interaction with a graphical element itself (e.g., by way of a mouse click on the graphical element) is not required to directly select the graphical element or its corresponding transducer. For example, a user might type a unique identifier associated with a graphical element or transducer via a keyboard, which can cause direct selection of that graphical element or transducer.

Further, although a user-based constituent selection of a user-selected graphical element followed by a machine-based constituent selection of that user-selected graphical element was provided above as an example of constituent selections involved with block 710, it should be noted that a user-based constituent selection of a first user-selected graphical element can also cause a machine-based constituent selection of a second, different, non-user-selected graphical element. For example, a user-performed mouse-click while the mouse cursor is above a user-selected between-graphical element 504 (e.g., a user-based constituent selection) can cause, possibly among other things, a machine-based constituent selection of the non-user-selected transducer graphical elements 502 at each end of the user-selected between graphical element 504. In this regard, the phrase, "user-selected", when used herein to describe a selected graphical element (e.g., a transducer graphical element or a between graphical element), is intended to refer to a graphical element directly selected by a user, as opposed to a non-user-selected graphical element, which is a machine-selected graphical element that is machine-selected either in response to no user instruction to select any graphical element or in response to a user-instruction to select a user-selected graphical element different than the machine-selected graphical element. In cases where a user selection of a user-selected graphical element causes a machine-selection of a different graphical element, it can be said that the different graphical element is indirectly selected by the user.

Further still, although a user-based constituent selection followed by a machine-based constituent selection was provided above as an example of constituent selections involved with block 710, it should be noted that any number of constituent selections, whether user-based or machine-based, can be involved with block 710. For example, depending upon how the user-interface is structured, one or more user-based constituent selections may result in one or more machine-based constituent selections. For instance, multiple user gestures (e.g., a double-fingered gesture on a touch screen, a mouse click-drag-and-release sequence, or other multiple user-gesture technique) might be required to identify a particular user-selected graphical element in order to cause the data processing device system to change the visual characteristics of (or provide another form of selection of) the particular user-selected graphical element. For another example, multiple user-based constituent selections might be a mouse click-and-hold followed by a dragging of a cursor to expand a selection box originating from the initial mouse click location, followed by a releasing of the mouse button to define the final size of the selection box. This initial user-based selection (comprised of the multiple user-based constituent selections) could be recognized by the data processing device system according to the above-discussed first group of instructions, and cause multiple machine-based or automatic constituent selections performed by the data processing device system according to the above-discussed second group of instructions. For instance, these multiple machine-based or automatic constituent selections could include a first constituent selection by the data processing device system of all graphical elements residing within the selection box, followed by a second constituent selection of only those graphical elements deemed to reside within the selection box whose corresponding transducers have been deemed acceptable for concurrent selection (see, e.g., the discussions below regarding block 707 in FIG. 7A, as well as the discussions below regarding FIG. 7B) or activation (see, e.g., the discussions below regarding block 708 in FIG. 7A and block 804 in FIG. 8).

Further still, although one or more user-based constituent selections followed by one or more machine-based constituent selections was provided above as an example of constituent selections involved with block 710, it should be noted that block 710 might not involve any user-based constituent selections. For example, graphical element selection according to block 710 might occur based upon data received from transducers, and this data might result in one or more machine-based or automatic constituent selections performed by the data processing device system.

It should be noted that, whenever a selection of a graphical element is discussed herein, such selection, in some embodiments, can include the above-discussed constituent selections. However, the above-discussed constituent selections are not limited to just selections of graphical elements and can apply to any selection described herein. For example, one or more user-based constituent selections of a user-selected graphical element can lead to one or more machine-based constituent selections of the user-selected graphical element or some other graphical element(s), which can lead to one or more machine-based selections of one or more transducers corresponding to the machine-selected graphical elements, the machine-based selection(s) of the one or more transducers possibly causing an activation of the one or more transducers. For another example, one or more user-based constituent selections of a user-selected graphical element can lead to one or more machine-based constituent selections of one or more data objects associated with the user-selected graphical element, one or more other associated graphical elements, one or more transducers associated with the user-selected graphical element, or one or more other objects associated with the user-selected graphical element, such as for purposes of viewing or changing properties of the one or more data objects or causing an activation based upon information provided by the one or more data objects. It should also be noted that the above-discussion regarding block 710 and user and machine based selections and constituent selections may apply, in some embodiments, to block 710 in FIG. 7B, block 808 in FIG. 8, block 908 in FIG. 9, blocks 807 and 808 in FIG. 10, or any other selection-based discussions herein.

In view of the above-discussion regarding selection types involved with block 710, in some embodiments, the instructions of block 710 are provided in a program that includes instructions configured to cause the data processing device system to receive a selection from the input-output device system of a transducer graphical element (e.g., transducer graphical element 502 or 602).

The selection of one or more graphical elements according to instructions of block 710 in FIG. 7A may cause, in some embodiments, an activation of at least some transducer sets of a transducer-based device (e.g., 200, 300, or 400) according to instructions of block 712. In some embodiments, block 712 includes instructions configured to cause an activation of each of at least some of the transducer sets of the transducer-based device (e.g., again exemplified by transducer based devices 200, 300, or 400) in response to receiving a selection of a corresponding one of the graphical elements (e.g., graphical elements 501, 601) in accordance with selection instructions included in block 710.

In some embodiments, the program can include activation instructions (e.g., in accordance with block 712) configured to, in response to receiving the selection of a transducer graphical element (e.g., transducer graphical element 502, 602), cause, via the input-output device system, activation of the respective transducer of the transducer-based device corresponding to the selected transducer graphical element. In various embodiments, the instructions configured to activate the respective transducer corresponding to the selected transducer graphical element include instructions that are configured to cause energy from an energy source device system (e.g., energy source device system 340) to be delivered to the respective transducer. In some embodiments, a sensing device system (e.g., provided at least in part by a number of the transducers) is arranged to sense at least one tissue electrical characteristic (e.g., tissue impedance) at a respective location at least proximate the respective transducer corresponding to the selected transducer graphical element with the energy delivered to the transducer (e.g., in some embodiments, tissue impedance may be measured between transducers on the structure 308 or between a transducer on the structure 308 and the indifferent electrode 326). In some of these various embodiments, the energy is sufficient for ablating tissue (e.g., tissue-ablating energy). In some of these various embodiments, an indifferent electrode (e.g., indifferent electrode 326) is provided (e.g., usually to an external surface of a body) while the transducer-based device is received in a bodily cavity within the body. A portion of the tissue-ablating energy delivered to the respective transducer corresponding to the selected transducer graphical element may be transmitted from the respective transducer to the indifferent electrode in a process typically referred to as monopolar ablation. In some embodiments, the instructions of block 712 that are configured to activate the respective transducer corresponding to the selected transducer graphical element includes instructions that are configured to cause a sensing device system (e.g., sensing device system 325) to detect electrophysiological activity in an intra-cardiac cavity at a location at least proximate the respective transducer. The detected electrophysiological activity can be displayed as an electrogram via the input-output device system (e.g. electrograms 535 in various ones of FIG. 5). In some embodiments, detection of electrophysiological activity in an intra-cardiac cavity at a location at least proximate various ones of the transducers occurs continuously. Other forms of activation of the respective transducer corresponding to the selected transducer graphical element are possible in other embodiments. In some embodiments, activation of the respective transducer corresponding to the selected transducer graphical element under the influence of the instructions configured to activate the respective transducer is referred to as monopolar activation. Monopolar activation can include activation for monopolar ablation or monopolar electrogram generation by way of non-limiting example.

For another example, in some embodiments, the instructions of block 710 are provided in a program that includes selection instructions configured to cause, due to execution of the selection instructions by the data processing device system (e.g., again exemplified by data processing device systems 110 or 310), reception of a selection from the input-output device system of a between graphical element (e.g., between graphical elements 504 or 604). In accordance with the instructions of block 712 the program can include activation instructions configured to, in response to receiving the selection, cause activation, via the input-output device system, of a respective set of two or more of the transducers (e.g., a pair of the transducers in some embodiments) of the transducer-based device corresponding to the between graphical element.

Advantageously, activating a set of two or more of the transducers based on a selection of a single graphical element (e.g., between graphical element 504 or 604) provides for a workflow that is less cumbersome and more expeditious than individually selecting the respective graphical elements (e.g., transducer graphical elements 502 or 602) associated with each transducer of the set of two or more of the transducers, especially when 50, 100, 200 or even over 300 or more transducer graphical elements are provided in the graphical representation. This is even more advantageous, when a single graphical element (e.g., between graphical element 504 or 604) provides additional information (e.g., spatial information) relating each of the transducers in the set of two or more of the transducers. For example, a between graphical element 504 or 604 can indicate a distance between or acceptability-of-activation of transducers of a corresponding transducer pair, and, accordingly, the between graphical element 504 or 604 provides, in some embodiments, information about the corresponding pair of transducers and, thereby, makes the selection process more efficient. In addition, allowing selection of the between-graphical elements for corresponding transducer activation can provide a more intuitive user-interface in certain applications. For example, such an arrangement allows a user to make selections along an ablation path or a path along which data is to be obtained, without having to focus on the transducers required to make that ablation path or acquire that data. The user can, for example, just select a path using between graphical elements (e.g., user-based selection(s)/constituent selection(s)), and the corresponding transducers are automatically selected (e.g., machine-based selection(s)/constituent selection(s)) in response. Since various ones of the between graphical elements need not be tied to any physical portion of the transducer-based device, they can be freely designed to reflect the path (e.g., over tissue or fluid) in which their corresponding transducers will interact when activated (e.g., by causing ablation or gathering data). In this regard, if the between graphical elements are configured to accurately represent their respective path segments in which ablation or data gathering will occur, according to some embodiments, the user can gain an even better understanding of the expected results of activation of the corresponding transducers.

In some of the embodiments where the instructions according to block 712 are configured to cause a data processing device system to activate a respective set of two or more of the transducers, the instructions according to block 712 include instructions that are configured to cause energy from an energy source device system (e.g., energy source device system 340) to be delivered to the respective set of two or more of the transducers. In some embodiments, a sensing device system (e.g., sensing device system 325) is arranged to sense at least one tissue electrical characteristic (e.g., tissue impedance) at respective locations at least proximate each transducer of the respective set of two or more of the transducers with the energy delivered to the respective set of two or more of the transducers (e.g., in some embodiments, tissue impedance may be measured between transducers on the structure 308 or between a transducer on the structure 308 and the indifferent electrode 326). In some embodiments, (a) a portion of the energy delivered to a first transducer of the respective set of two or more of the transducers (e.g., first transducer 306*a*) is transmitted by the first transducer, (b) a portion of the energy delivered to a second transducer of the respective set of two or more of the transducers (e.g., second transducer 306*b*) is transmitted by the second transducer, or both (a) or (b). In some of embodiments, (a) a portion of the energy delivered to a first transducer of the respective set of two or more of the transducers (e.g., first transducer 306*a*) is transmitted by the first transducer to a second transducer of the respective set of two or more of the transducers (e.g., second transducer 306*b*), (b) a portion of the energy delivered to the second transducer of the respective set of two or more of the transducers is transmitted by the second transducer to the first transducer, or both (a) or (b). In some embodiments, the energy is sufficient for ablating tissue (e.g., tissue ablating energy). In some example embodiments, a selected between graphical element (e.g., between graphical elements 504 or 604) is representative of a physical path extending between a respective pair of the transducers associated with the selected between graphical element and the energy is sufficient for ablating a portion of tissue extending along the physical path. A portion of the tissue-ablating energy may be transmitted between the respective pair of the transducers in a process typically referred to as bipolar ablation. In some embodiments, an indifferent electrode (e.g., indifferent electrode 326) is provided (e.g., usually to an external surface of a body) while the transducer-based device is received in a bodily cavity within the body. Some of the tissue-ablating energy may be transmitted between the respective pair of the transducers while some of the tissue-ablating energy may be transmitted from various ones of the respective pair of the transducers to the indifferent electrode in a process typically referred to as blended monopolar-bipolar ablation. The term "bipolar ablation" as used in this disclosure is to be interpreted broadly to include blended monopolar-bipolar ablation in some embodiments.

In addition to embodiments where the instructions according to block 712 are configured to cause a data processing device system to cause bipolar ablation, the instructions according to block 712, in some embodiments, are configured to cause a data processing device system to cause multi-transducer monopolar ablation with the respective set of two or more of the transducers, e.g., dual monopolar ablation for two transducers, or triple monopolar ablation for three transducers. In such cases, for example, the respective set of two or more of the transducers may be 'queued' for monopolar ablation, such that monopolar ablation occurs for each transducer in the respective set of two or more of the transducers within some period of time, but not necessarily at the same time or even contiguously one right after another. In this regard, references herein to the occurrence of monopolar ablation for more than one transducer may include this multi-transducer monopolar ablation according to some embodiments. In addition, any reference herein to the occurrence of bipolar ablation may be replaced with the occurrence of dual monopolar ablation (or other multi-transducer monopolar ablation when more than two transducers are involved), according to some embodiments.

In some embodiments, the instructions, according to block 712, configured to activate the respective set of two or more of the transducers include instructions that are configured to cause a sensing device system to detect electrophysiological activity in an intra-cardiac cavity at each of respective locations at least proximate each of the transducers of the set. The detected electrophysiological activity detected at each of the respective locations can be displayed as an electrogram via the input-output device system (e.g., electrograms 535 shown in various ones of FIG. 5). In some example embodiments, a combined electrogram (e.g., a bipolar electrogram) (not shown) may be determined (e.g., by instructions provided by a program) from the respective electrograms associated with each transducer of the respective set of two or more of the transducers. The program may include instructions configured to display the combined electrogram via the input-output device system. Other forms of activation are possible in other embodiments involving activation of a respective set of two or more of the transducers. In some embodiments, activation under the influence of the instructions configured to activate a respective pair of transducers associated with a selected between graphical element may be referred to as bipolar activation when the pair of the transducers is activated in a bipolar manner (e.g., bipolar ablation or bipolar electrogram generation). Selection of each of at least some of the plurality of graphical elements 501 or 601 in accordance with the instructions of block 710 may include independent selections of each of the at least some of the graphical elements 501 or 601.

Having discussed embodiments where blocks 710 and 712 follow block 702 in FIG. 7A, a discussion will now begin regarding embodiments where block 704 follows block 702. Block 704 of method 700, in some embodiments, includes instructions (e.g., input instructions included in a program) that cause the data processing device system (e.g., data processing device systems 110 or 310) to receive transducer data from at least some of the transducers via the input-output device system. This transducer data can take various forms, such as one or more of various detected characteristics including, but not limited to, e.g., electrical characteristics (such as electrical potential or impedance), thermal characteristics (such as temperature), and force.

Various embodiments can process or analyze the transducer data received by the data processing device system according to the instructions of block 704 in order to, for example, generate and possibly display one or more electrograms, determine the acceptability of selection or activation of particular transducers, generate a map (e.g., a map of anatomical features), determine the status of tissue ablation, or combinations of these tasks. Accordingly, it should be noted that some embodiments need not be limited to any particular form of processing or analysis of the transducer data received by the data processing device system according to the instructions of block 704. In this regard, although various embodiments need not be limited to any particular processing or analysis of the transducer data received according to the instructions of block 704, block 706 of method 700 pertains to some embodiments where the transducer data is analyzed to identify various regions that correspond to at least a portion of one or more anatomical features. For example, according to some embodiments, block 706 includes instructions (e.g., determination or identification instructions included in a program) that are configured to identify various regions 525 (e.g., FIGS. 5C-5I) in the graphical representation (generated according to the instructions of block 702) that correspond to at least a portion of one or more anatomical features based at least on an analysis of the transducer data.

In embodiments such as these, where the transducer-based device is deployed in a bodily cavity (e.g., when the transducer-based device takes the form of a catheter device arranged to be percutaneously or intravascularly delivered to a bodily cavity), it may be desirable to perform various mapping procedures in the bodily cavity. Although these mapping procedures can be implemented according to the instructions of block 706, these mapping procedures can be performed at other times, such as any time during the generation of or after the display of the graphical representation of at least a portion of the transducer-based device (e.g., block 702, 802, or 902). It is noted that in some embodiments, the mapping procedure need not be limited to the mapping of various anatomical landmarks. For example, when the bodily cavity is an intra-cardiac cavity, the mapping procedure may include mapping electrophysiological activity in the intra-cardiac cavity. In some embodiments, the mapping procedure may include mapping varying degrees of contact between various ones of the transducers (e.g., electrodes) and a tissue surface of a bodily cavity into which the transducers are located.

An example of the mapping performed by devices according to various embodiments (such as those represented by block 706 in FIG. 7A) would be to locate the position of the ports of various bodily openings positioned in fluid communication with a bodily cavity. For example, in some embodiments, it may be desired to determine the locations of various ones of the pulmonary veins or the mitral valve that each interrupt an interior surface of an intra-cardiac cavity such as a left atrium.

In some example embodiments, the mapping is based at least on locating such bodily openings by differentiating between fluid and tissue (e.g., tissue defining a surface of a bodily cavity). There are many ways to differentiate tissue from a fluid such as blood or to differentiate tissue from a bodily opening in case a fluid is not present. Four approaches may include by way of non-limiting example:

1. The use of convective cooling of heated transducer elements by fluid. A slightly heated arrangement of transducers that is positioned adjacent to the tissue that forms the interior surface(s) of a bodily cavity and across the ports of the bodily cavity will be cooler at the areas which are spanning the ports carrying the flow of fluid.

2. The use of tissue impedance measurements. A set of transducers positioned adjacently to tissue that forms the interior surface(s) of a bodily cavity and across the ports of the bodily cavity can be responsive to electrical tissue impedance. Typically, heart tissue will have higher associated tissue impedance values than the impedance values associated with blood.

3. The use of the differing change in dielectric constant as a function of frequency between blood and tissue. A set of transducers positioned around the tissue that forms the interior surface(s) of the atrium and across the ports of the atrium monitors the ratio of the dielectric constant from 1 KHz to 100 KHz. Such can be used to determine which of those transducers are not proximate to tissue, which is indicative of the locations of the ports.

4. The use of transducers that sense force (e.g., force sensors). A set of force detection transducers positioned around the tissue that forms the interior surface of the bodily cavity and across the bodily openings or ports of the bodily cavity can be used to determine which of the transducers are not engaged with the tissue, which is indicative of the locations of the ports.

Figure 5C:
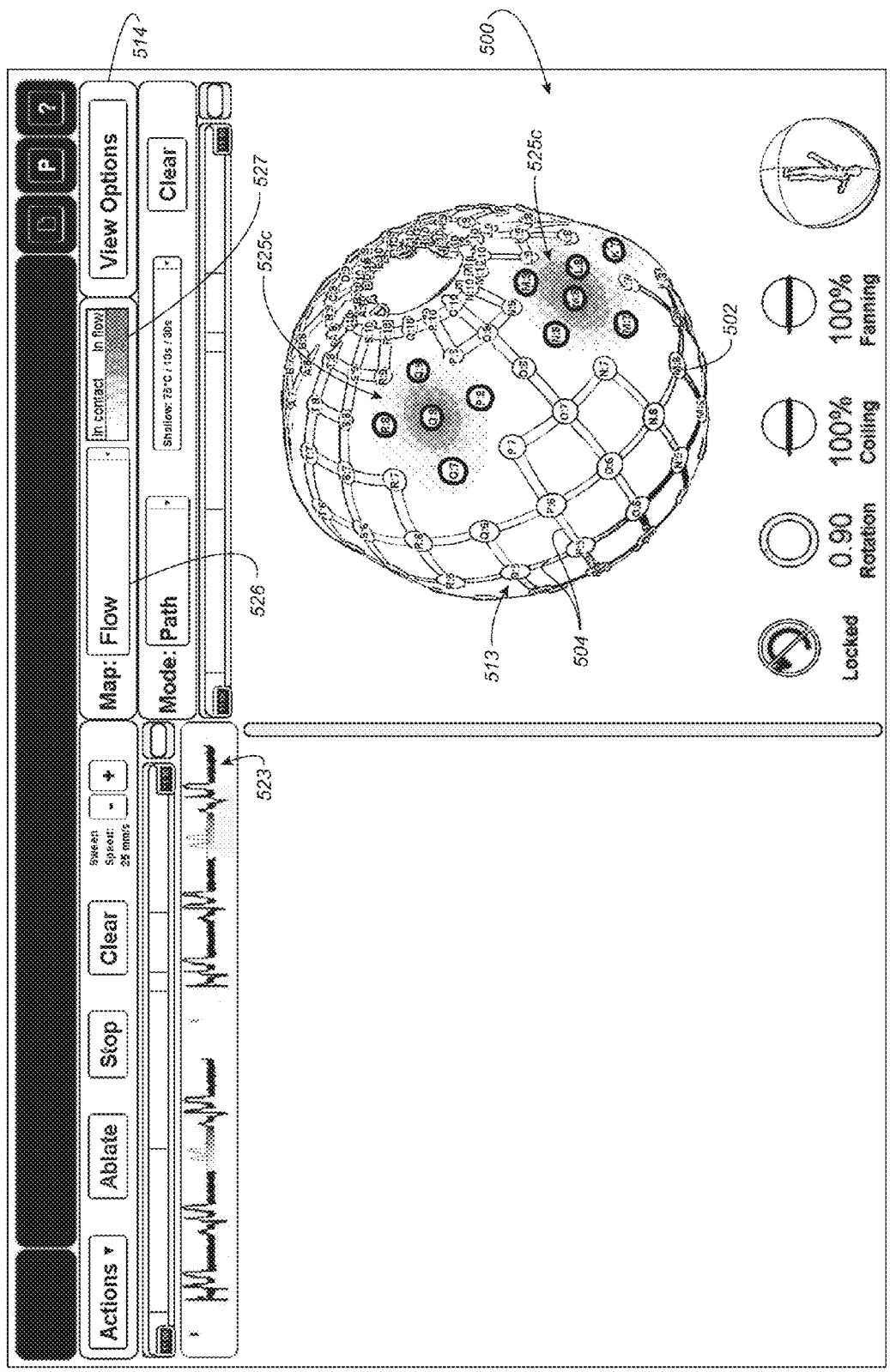
FIG. 5C illustrates the graphical representation provided by the graphical interface of FIG. 5A with the addition of various regions determined based at least on an analysis of transducer data.
Figure 5D:
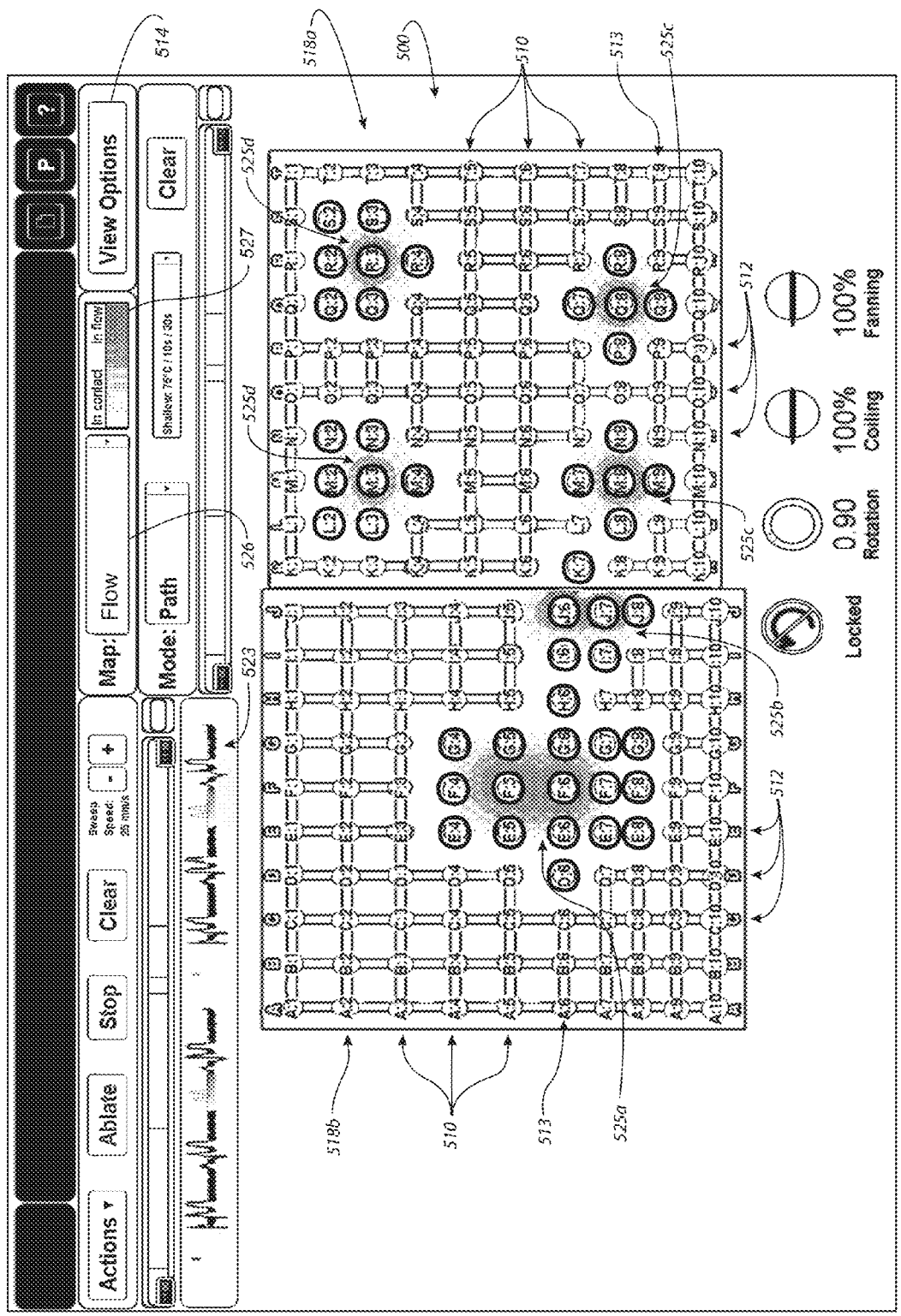
FIG. 5D illustrates the graphical representation of FIG. 5C depicted two-dimensionally.

The graphical interface of FIG. 5C includes various regions 525*c* (e.g., part of a plurality of regions collectively referred to as regions 525 when considering all of the FIG. 5) added to the graphical representation 500 of the transducer-based device. The regions 525 could be identified and displayed according to the instructions of block 706 in FIG. 7A in some embodiments. Although, such regions 525 could be identified and displayed at other times or according to other instructions. In some embodiments, the graphical interface depicted in FIG. 5C is generated after the transducer-based device was received in a bodily cavity having various anatomical features of interest and the control button 526 identified as "Map" was activated via the input-output device system to select a mode referred to as "Flow". Techniques for flow-based mapping techniques are disclosed in commonly assigned U.S. Patent Application Publication No.: US 2008/0004534. In various embodiments associated with various ones of FIG. 5, the anatomical features of interest are ports of a mitral valve and various pulmonary veins positioned in fluid communication with an intra-cardiac cavity (e.g., a left atrium in this embodiment). In these various embodiments, the transducers of the transducer-based device are distributed adjacent respective regions in the intra-cardiac cavity that can include relatively lower blood flow regions (e.g., adjacent a tissue surface of the intra-cardiac cavity), relatively higher flow regions (e.g., over the ports of the intra-cardiac cavity). It is noted that relatively lower blood flow regions in the intra-cardiac cavity may occur when a transducer is positioned in contact with a tissue surface to restrict blood flow at the contacted tissue. In some example embodiments, the relatively large number of transducers in the distribution advantageously allows for each of the transducers to be positioned adjacent their corresponding regions with little or no repositioning of the transducer-based device thereby facilitating obtaining transducer-based data concurrently from a multitude of locations in the bodily cavity. In this example embodiment, activation via the input-output device system of the control button 526 identified as "Map" can allow for other types of maps, including but not limited to, tissue contact maps, isochronal maps, isopotential maps, propagation maps, and various other voltage maps associated with intra-cardiac electrical activity.

Returning to the specific case of block 706 in FIG. 7A, one or more of the above-discussed mapping procedures may be implemented according to instructions of block 706 to identify various regions 525 in the graphical representation that correspond to at least a portion of one or more anatomical features based at least on an analysis of the transducer data received according to block 704. In some of these embodiments, the one or more anatomical features are the ports of various bodily openings (e.g., pulmonary veins, left lateral appendage, mitral valve) positioned in fluid communication with the intra-cardiac cavity and the transducer data includes data containing various blood flow data within the bodily cavity. In this embodiment, the instructions in block 706 include instructions that are configured to cause the input-output device system to display the identified regions 525 of the graphical representation 500. In this example embodiment, the various ones of the identified regions 525 are shown in the three-dimensional graphical representation 500 provided by the graphical interface of FIG. 5C and the two-dimensional graphical representation 500 provided by the graphical interface of FIG. 5D.

In FIG. 5D, the relatively large region 525*a* is associated with the mitral valve, region 525*b* is associated with the left lateral appendage, regions 525*c* are associated with the left pulmonary vein group and regions 525*d* are associated with the right pulmonary vein group. Each of the regions 525 is depicted in the graphical representation 500 with a graduated pattern provided by the flow identifier 527 in the graphical interface of FIG. 5D. A graduated pattern can be employed to indicate various regions in the graphical representation corresponding to different regions of flow in the intra-cardiac cavity. The identified regions 525 may be identified by any suitable methods including the use of gray-scale patterns, different colors, different opacities, different intensities and different shapes. It is understood that other embodiments may employ other techniques to identify regions in the graphical representation corresponding to a desired anatomical feature. For example, transducer-based data containing blood and tissue impedance information may be employed to determine regions 525. As previously discussed in this detailed description, a selection box 522 may be optionally enabled to allow for the selective inclusion in the graphical representation of graphical elements associated with various anatomical features associated with regions 525.

Identification of the regions 525 may be motivated for various reasons. For example, in embodiments in which transducers of transducer-based device are activated to treat or diagnose various regions in a bodily cavity, the identification of various regions 525 and their spatial relationship relative to one another may impact the efficacy of the treatment or diagnostic procedure. For example, in situations in which at least some of the transducers of a transducer-based device are employed to ablate various regions within an intra-cardiac cavity (e.g., to treat atrial fibrillation), ablation of a pulmonary vein may result in an undesired condition referred to as pulmonary stenosis. Identification of regions 525c, 525d in the graphical representation may be employed to reduce occurrences of this undesired condition.

In some embodiments, contrary to what is shown in FIG. 7A, block 706 immediately precedes block 710, with block 707, block 708, or both omitted. However, in some embodiments, block 707 is between blocks 706 and 710 as shown in FIG. 7A. In addition, in some embodiments, block 707 need not occur between blocks 706 and 710 as shown in FIG. 7A, and can, for example, instead occur immediately after block 704, with block 710 immediately following and block 706 omitted. Similarly, in some embodiments, block 708 is between blocks 706 and 710 as shown in FIG. 7A. However, in some embodiments, block 708 need not occur between blocks 706 and 710 as shown in FIG. 7A, and can, for example, instead occur immediately after block 704, with block 710 immediately following and block 706 omitted.

In any event, regarding block 707 and block 710, concurrent selection of a set of two or more of the transducers in the transducer-based device (e.g., a pair of adjacent transducers 306) is provided in some embodiments for enhanced workflows that are less cumbersome and more expeditious than those associated with non-concurrent selection of each transducer of the set of two or more of the transducers. For example, in some embodiments, a user-based selection of a between graphical element (e.g., between graphical elements 504 or 604) allows for a machine-based concurrent selection of an associated set of two or more transducers in various embodiments.

In this regard, block 707 includes, in some embodiments, identification instructions (e.g., instructions provided in a program) configured to cause identification of which of the respective transducers of each of various sets of two or more of the transducers of a transducer-based device are and which are not acceptable for concurrent selection.

Concurrent selection or non-concurrent selection of the respective transducers of a given one of the sets of two or more of the transducers may be motivated for various reasons. For example, concurrent selection of transducers may lead to a more expeditious workflow that advantageously reduces diagnostic or treatment times. Conditions, however, may not allow for the concurrent selection of the respective transducers of each of various ones of selectable sets of two or more transducers.

For example, if a transducer of a transducer pair is deemed not-activation-ready (e.g., according to the instructions of block 708 or block 804, discussed below), the transducer pair can be deemed, according to the instructions of block 707, to be a transducer set that is not acceptable for concurrent selection. A set of two or more transducers (e.g., a pair of transducers) that is identified (e.g., via instructions of block 708 or block 804, discussed below) as including at least one not-activation-ready transducer of the transducer-based device (e.g., a not-ablation-ready transducer) may, in some embodiments, be deemed, according to the identification instructions of block 707, as a set of two or more of the transducers of a transducer-based device whose respective transducers are not acceptable for concurrent selection. In some embodiments, a set of two or more of the transducers that is identified (e.g., via instructions of block 708 or block 804, discussed below) as not including any not-activation-ready transducer of the transducer-based device (e.g., a not-ablation-ready transducer) may be deemed, according to the identification instructions of block 707, as a set of two or more of the transducers whose respective transducers are acceptable for concurrent selection.

The identification instructions of block 707 need not be limited to causing identification of a set of two or more transducers as acceptable or not acceptable for concurrent selection, and need not be limited to determining the acceptability of concurrency of selection based upon a determination of activation-ready transducers (e.g., via instructions of block 708 or block 804, discussed below). In some embodiments, the identification instructions of block 707 include instructions configured to cause, at least in part, the identification of the respective transducers of each of the sets of two or more transducers which are acceptable for concurrent selection based at least on an analysis of transducer data received in accordance with the instructions of block 704. In other words, acceptability of the concurrency of selection can be determined on a transducer-group basis or on an individual-transducer basis. These differing approaches can lend themselves to different circumstances. For example, in some situations, it may be preferable to determine whether an entire group of transducers is acceptable for concurrent selection, while in other situations, it may be beneficial to know whether individual transducers in each group are acceptable for concurrent selection.

In some embodiments, each of the sets of two or more of the transducers of the transducer-based device including a pair of adjacent transducers that are spaced with respect to one another across a corresponding region of space, each region of space not including any transducer. In some of these embodiments, a determination of whether or not one of these regions of space is acceptable for activation by its corresponding respective transducer pair is used as a basis for determining whether or not the respective transducer pair is acceptable for concurrent selection. For example, if the region of space is deemed to be acceptable for activation by the corresponding respective transducer pair, then the respective transducer pair is identified as being acceptable for concurrent selection in some embodiments. In some embodiments, the regions of space are determined to be acceptable for activation of the corresponding respective transducers according to determination instructions (e.g., according to some embodiments of the instructions of block 708 in FIG. 7A or block 804 in FIG. 8, discussed below). In this regard, the identification instructions of block 707 may be further configured to cause, at least in part, the identification of the respective transducers of each of the pairs of adjacent ones of the transducers which are acceptable for concurrent selection as the respective transducers of each of the plurality of pairs of adjacent transducers whose corresponding regions of space have been determined, according to determination instructions (not shown, but similar to the instructions of block 708 or block 804, discussed below) to be acceptable for activation of the corresponding respective transducers, and cause, at least in part, the identification of the respective transducers of each of the pairs of adjacent ones of the transducers which are not acceptable for concurrent selection as the respective transducers of each of the plurality of pairs of adjacent transducers whose corresponding regions of space have been determined, according to the determination instructions (not shown, similar to the instructions of block 708 or block 804, discussed below) to be not acceptable for activation of the corresponding respective transducers.

Acceptability of concurrency of selection of transducers or a region of space corresponding to transducers need not based on or solely on a determination of the acceptability of activation of the corresponding transducers (e.g., pursuant to instructions according to block 708 or block 804, discussed below) in some embodiments. In this regard, transducers or regions of space each corresponding to transducers can be deemed to be acceptable or not acceptable for concurrent selection, according to various embodiments of the instructions of block 707, based on any reason which might make it beneficial or not beneficial to concurrently select the corresponding transducers.

In some embodiments, a result of one or more of the identifications according to the instructions of block 707 is the distinguishing display (e.g., by different visual characteristics) of graphical elements associated with transducers identified to be acceptable for concurrent selection as compared to graphical elements associated with transducers identified to be not-acceptable for concurrent selection. In this regard, the instructions according to block 707 include, in some embodiments, instructions configured to cause the graphical representation displayed according to the instructions of block 702 to visually distinguish its graphical elements associated with transducers identified to be acceptable for concurrent selection as compared to graphical elements associated with transducers identified to be not-acceptable for concurrent selection. In this regard, any instructions according to block 707 that affect the appearance of the graphical representation can be considered to be part of block 702 in some embodiments. The same applies to block 708 (with respect to block 702) in FIG. 7A, block 804 (with respect to block 802) in FIG. 8, block 812 (with respect to block 802) in FIG. 8, block 910 (with respect to block 902) in FIG. 9, block 912 (with respect to block 902) in FIG. 9, discussed below, and any other similar discussions herein, where distinguishing visual characteristics of graphical elements in a graphical representation facilitate differences in information or status.

To elaborate with respect to block 702 for example purposes only, various graphical element sets may be displayed by the display instructions of block 702, each graphical element set including one or more graphical elements (e.g., graphical elements 501 or 601) and each graphical element set associated with a respective one of a number of sets of two or more of the transducers (e.g., transducers of transducer-based devices 200, 300 or 400). Method 700 may include instructions (e.g., instructions provided in a program), (not shown) configured to cause graphical representation instructions of block 702 to cause the input-output device system (e.g., input-output device system 120 or 320) to display each of the graphical element sets associated with each of the sets of two or more of the transducers whose respective transducers have been identified (e.g., according to identification instructions associated with block 707) to be acceptable for concurrent selection with a respective set of visual characteristics that distinguishes each of the graphical element sets associated with each of the sets of two or more of the transducers whose respective transducers have been identified to be acceptable for concurrent selection from each of the graphical element sets associated with each of the sets of two or more of the transducers whose respective transducers have been identified to be not acceptable for concurrent selection. Differences in the displayed visual characteristics may include different colors, opacities, hues, intensities, shading, patterns, shapes or the addition or removal of any displayed information suitable for distinguishing a concurrently-selectable transducer set from a not-concurrently-selectable transducer set.

For example, in some embodiments associated with FIGS. 5C and 5D, only the between graphical elements 504 that are each associated with a corresponding set of transducers (e.g., a corresponding pair of transducers in this embodiment) whose respective transducers are deemed acceptable for concurrent selection are displayed, and between graphical elements 504 that are associated with a corresponding pair of transducers that include at least one transducer that is deemed not acceptable for concurrent selection is not displayed. The presence or absence of a particular graphical element (e.g., a between graphical element 504) may form at least part of differences associated with displayed visually characteristics referenced in block 707.

In various embodiments of FIGS. 5C and 5D, the absent between graphical elements 504 indicate that their respective pairs of transducers each have been identified (e.g., according to the instructions of block 708, discussed below) to be over a region of space that is deemed unacceptable for activation (e.g., ablation) because such regions of space include a portion of a port of a bodily opening, which, in some embodiments, is not acceptable for ablation. These identifications lead to a conclusion, in some embodiments, (e.g., according to the instructions of block 707), that these respective pairs of transducers are not acceptable for concurrent selection in some embodiments. In some of these embodiments, such as those illustrated by FIGS. 5C and 5D, the graphical elements associated with these respective transducer pairs identified not to be acceptable for concurrent selection, are not displayed so that they are visually distinguished from the between graphical elements 504, which are displayed and which are associated with respective transducer pairs that have been identified to be acceptable for concurrent selection according to the instructions of block 707.

One reason for identifying a transducer set as being not-acceptable for concurrent selection according to the instructions of block 707 is that the transducer set, when activated, could be harmful to an affected region of space. However, other factors may also have a bearing on whether the respective transducers of a particular set of two more of the transducers are deemed concurrently selectable. In addition, combinations of different factors may be considered in the determination of whether the respective transducers of a particular set of two or more of the transducers are, or are not, acceptable for concurrent selection.

By way of a non-limiting example, another reason for determining a transducer set to be not-acceptable for concurrent selection, according to some embodiments of the instructions of block 707, is that transducers in the transducer set are too far apart, such that, for example, activation of the transducers in the set would lead to a result that may be considered ineffective. For example, if a transducer pair is too far apart, ablation performed by the pair might not be able to reliably form an electrophysiological conduction block between them.

Figure 5E:
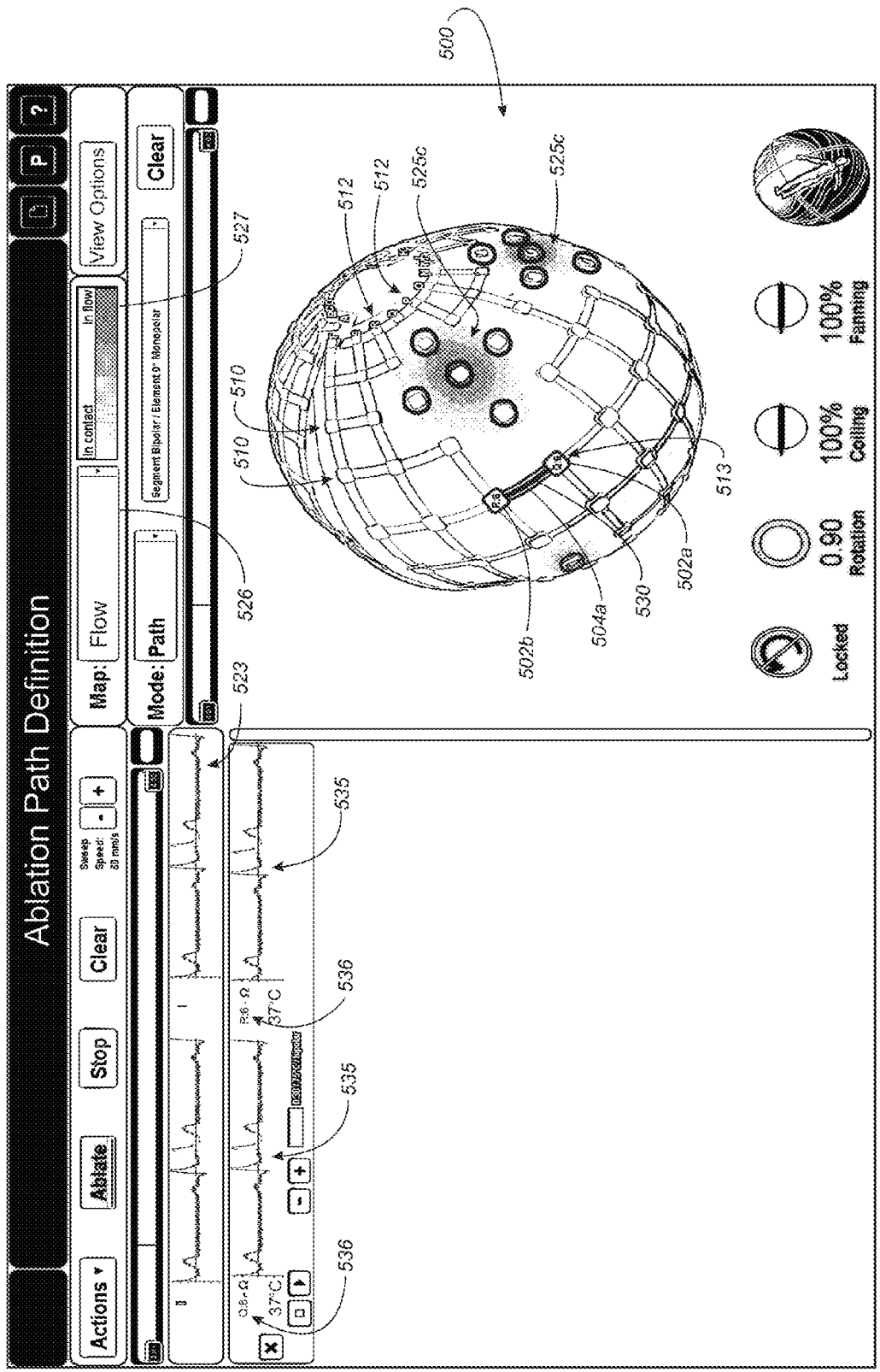
FIG. 5E illustrates the graphical representation of FIG. 5C with a graphical element selected in accordance with various example embodiments.
Figure 5F:
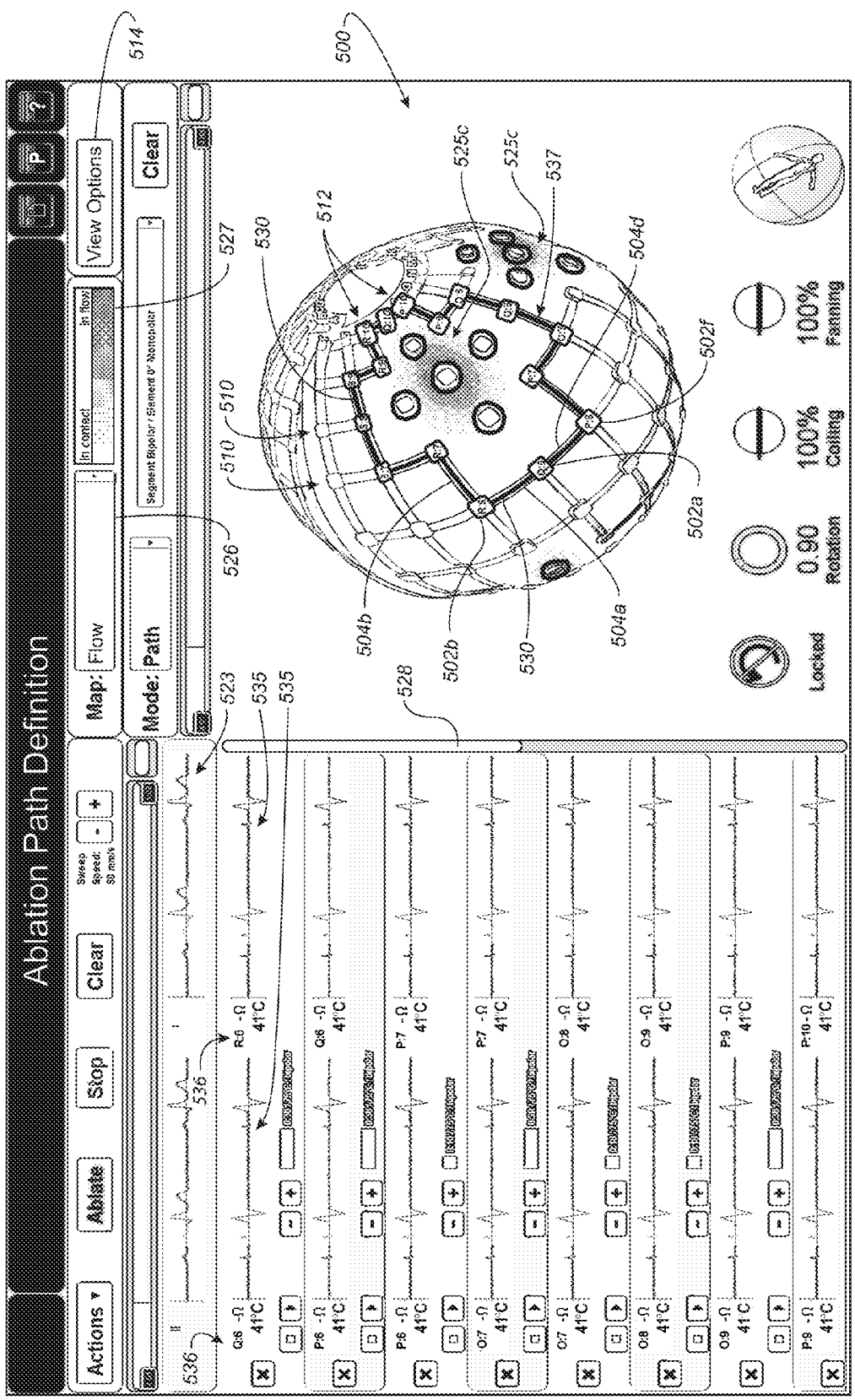
FIG. 5F illustrates the graphical representation of FIG. 5C with an addition of a depicted path.
Figure 5G:
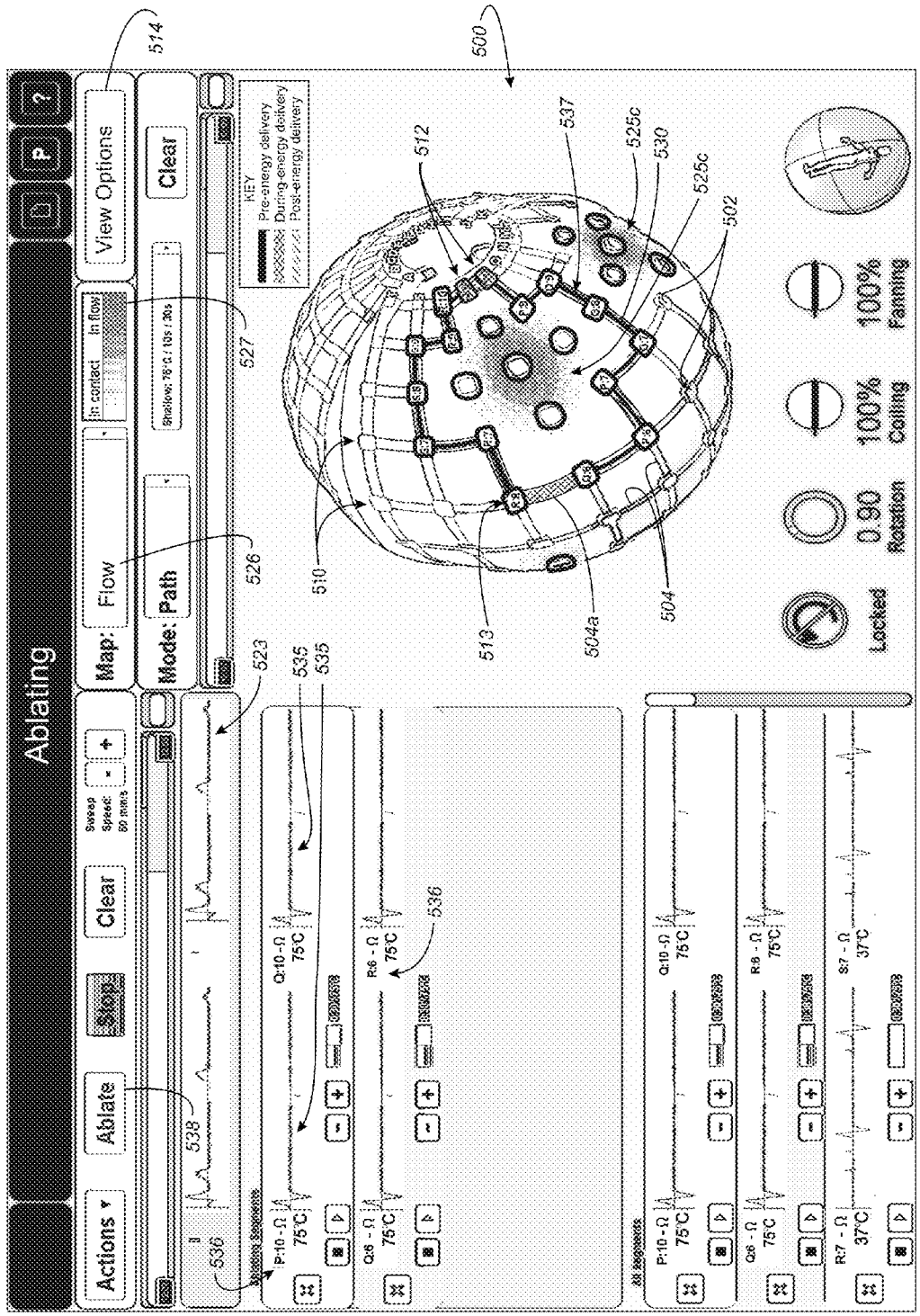
FIGS. 5G and 5H illustrate the graphical representation of FIG. 5F associated with two successive activations of various transducer sets selected according to a first sequence but activated according to a second sequence different from the first sequence.
Figure 5H:
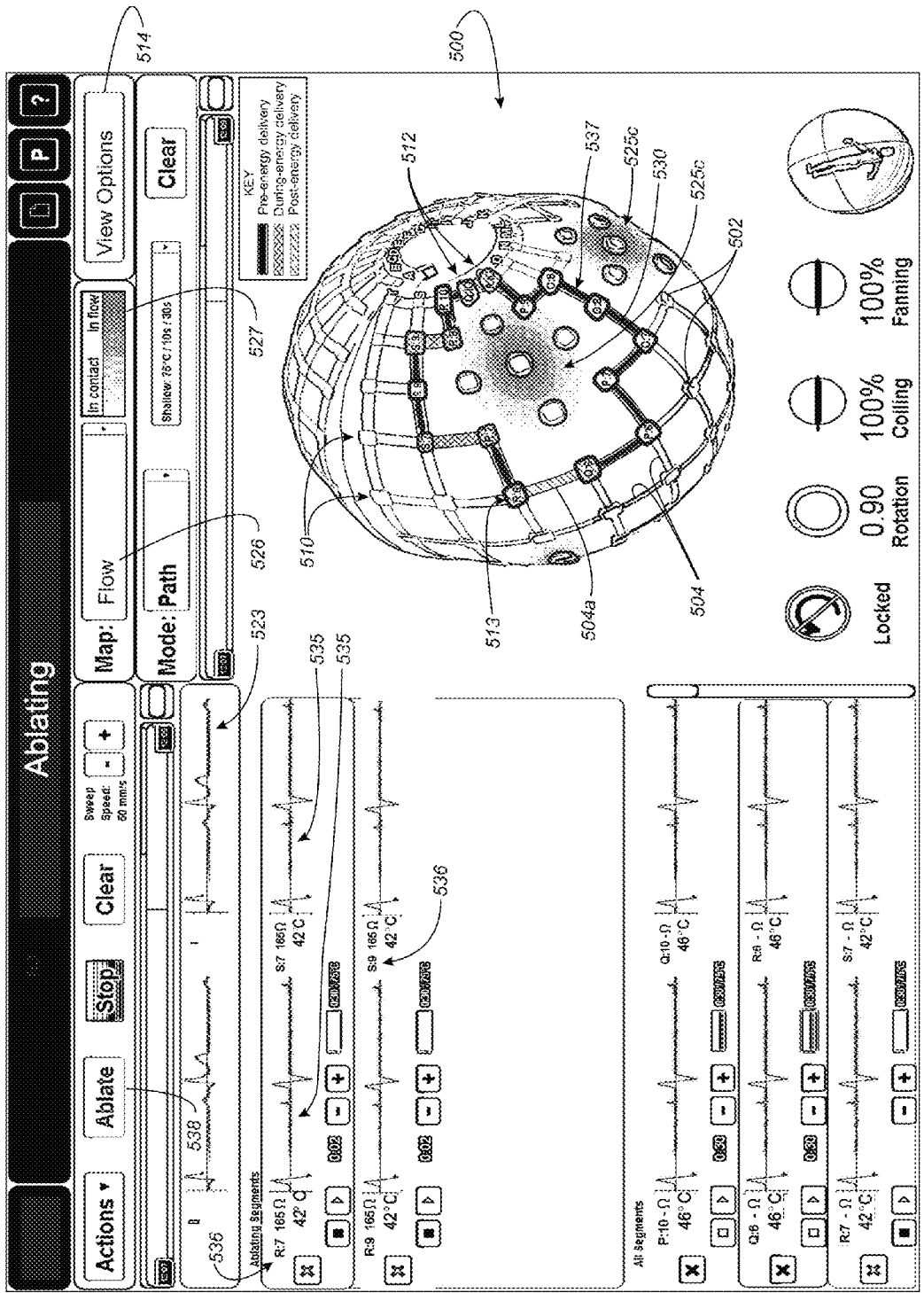
Figure 5I:
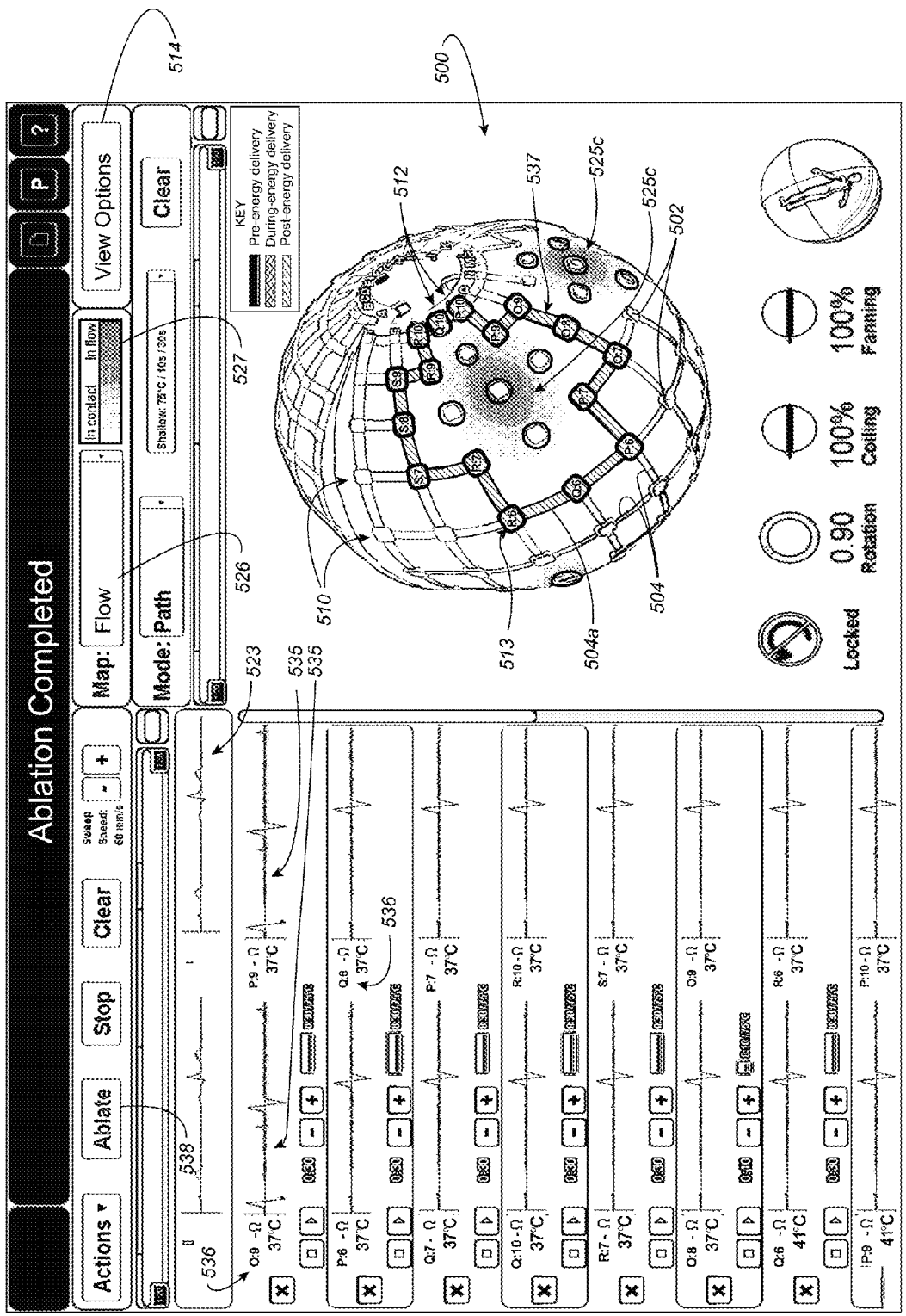
FIG. 5I illustrates the graphical representation of FIG. 5F after the completion of the activation of all the various transducer sets according to the second sequence.
Figure 5J:
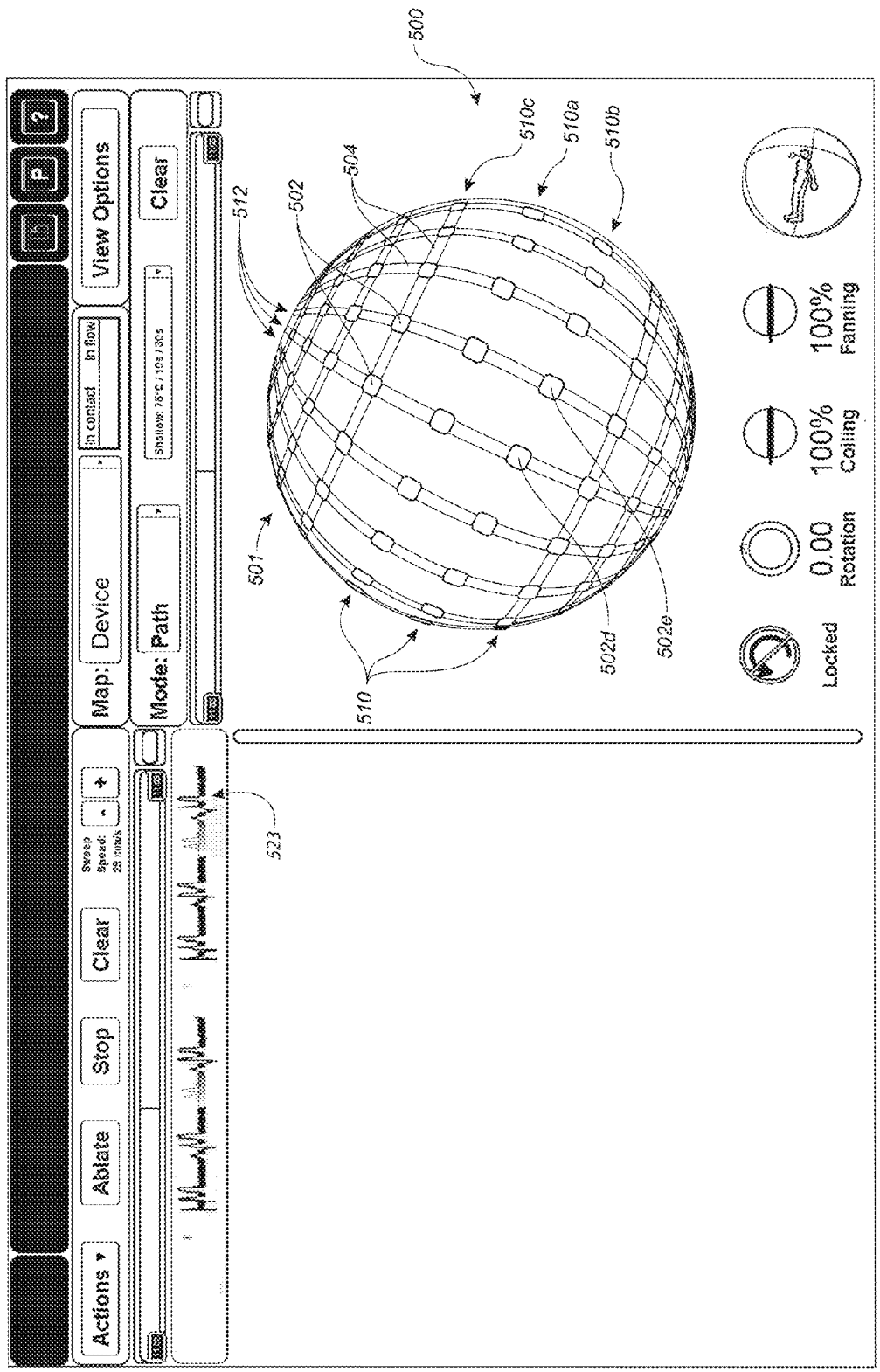
FIG. 5J illustrates a graphical interface providing a graphical representation of at least a portion of a transducer-based device according to various example embodiments.

The embodiments of FIG. 5J illustrate examples of transducer pairs being too far apart and, therefore, being deemed to be unacceptable for concurrent selection according to some embodiments of the instructions of block 707. In this regard, FIG. 5J illustrates a graphical interface including a graphical representation 500 provided by an input-output device system (e.g., input-output device system 120 or 320) according to some embodiments. Graphical representation 500 in FIG. 5J is similar to the graphical representation 500 in FIG. 5A and includes a plurality of graphical elements including various transducer graphical elements and between graphical elements. For convenience of discussion, the plurality of graphical elements of graphical representation 500 are identified as graphical elements 501, the plurality of transducer graphical elements of graphical representation 500 are identified as transducer graphical elements 502, and the between graphical elements of graphical representation 500 are identified as between graphical elements 504. The graphical elements 501 in graphical representation 500 in FIG. 5J are arranged in a plurality of rows 510 (e.g., latitudinal rows) and a plurality of columns 512 (e.g., longitudinal columns) in a manner similar to that shown by graphical representation 500 in FIG. 5A. The transducer graphical elements 502 and between graphical elements 504 in graphical representation 500 in FIG. 5J have similar associations with a spatial distribution of transducers (e.g., transducers 306 in FIG. 3A, 3B) as their counterparts in graphical representation 500 in FIG. 5A.

In this illustrated embodiment, graphical representation 500 in FIG. 5J is distinguished from graphical representation 500 in FIG. 5A in various ways including an absence of a between graphical element 504 between the respective transducer graphical elements 502 of various adjacent pairs of the transducers graphical elements 502. For example, a between graphical element 504 is not displayed between adjacent transducer graphical elements 502d and 502e. In this illustrated embodiment, an absence of between graphical elements 504 occurs in some of the rows 510. In this illustrated embedment, the presence or absence of a particular between graphical element 504 in the graphical representation 500 in FIG. 5J is indicative, at least in part, of differences in the visual characteristics of particular graphical elements 501 associated with sets of two or more transducers whose respective transducers have been identified by the instructions of block 707 to be acceptable for concurrent selection and particular graphical elements 501 associated with sets of two or more transducers whose respective transducers have been identified by the instructions of block 707 to be not acceptable for concurrent selection. In various example embodiments, between graphical elements 504 are displayed between corresponding pairs of transducer graphical elements 502 associated with transducers that have been identified by the instructions of block 707 to be acceptable for concurrent selection, while between graphical elements 504 are not displayed between corresponding pairs of transducer graphical elements 502 associated with transducers that have been identified by the instructions of block 707 to be not acceptable for concurrent selection.

In some example embodiments, the instructions 707 are further configured to cause, at least in part, the identification of the respective transducers of each of the pairs of adjacent ones of the transducers in a distribution which are acceptable for concurrent selection as the respective transducers of each of the plurality of pairs of adjacent ones of the transducers in the distribution having a respective transducer-to-transducer distance that is not greater than a target transducer-to-transducer distance, and cause identification, at least in part, of the respective transducers of each of the pairs of adjacent ones of the transducers in the distribution which are not acceptable for concurrent selection as the respective transducers of each of the plurality of pairs of adjacent ones of the transducers in the distribution having a transducer-to-transducer distance that is greater than the target transducer-to-transducer distance. In embodiments involving relatively low temperature ablations, the target transducer-to-transducer distance might be one-half an electrode width. In embodiments involving relatively higher temperature ablations, larger target transducer-to-transducer distances might be sufficient. In various embodiments, ablation temperatures lower than the thermal coagulation temperature of blood are preferred. Other factors that may impact the target transducer-to-transducer distance might include tissue thickness, tissue type, characteristics of fat layers embedded in the tissue, the blood's susceptibility to forming coagulum, and whether or not a pair of transducers performing the ablation are separated by a physical portion of the transducer-based device, such as by an elongate member 304. In some embodiments, a target transducer-to-transducer distance associated with a particular pair of the transducers is determined or selected to increase a likelihood that a electrophysiological conduction block that blocks electrophysiological activity between the particular pair of transducers will be formed in tissue upon activation of the transducers. In some embodiments, concurrent selection of a pair of transducers whose activation would not likely result in a desired electrophysiological conduction block may be deemed unacceptable according to the instructions of block 707.

It is noted that different target transducer-to-transducer distances may be employed for different pairs of the transducers. For example, a first target transducer-to-transducer distance associated with a pair of transducers spaced with respect to one another over a region of space that includes a physical portion of a structure on which the transducers are located (e.g., structure 308) may be different (e.g., greater) than a second target transducer-to-transducer distance associated with a pair of transducer that are spaced with respect to one another across a region of space that does not include a physical portion of a supporting structure (e.g., structure 308). In the embodiments of FIG. 5J, between graphical elements 504 are not displayed between transducers graphical elements 502 arranged in particular ones of the rows 510 having the greatest depicted spacing between adjacent transducer graphical elements 502.

In some particular embodiments, between graphical elements 504 are not displayed between transducer graphical elements 502 arranged in rows 510a and 510b, because the transducer-to-transducer distances of the transducers (e.g., transducers 306) corresponding to these transducer graphical elements 502 in these rows each exceeds a target distance (e.g., in use). Therefore, in some embodiments, it is determined (e.g., according to the instructions of block 707) that the transducers corresponding to the transducer graphical elements 502 along rows 510a and 510b are not acceptable for concurrent selection, which results in the non-display of the corresponding between graphical elements 504. However, between graphical elements 504 are displayed between transducer graphical elements 502 arranged in the other rows (including row 510c), because the transducer-to-transducer distances of the transducers corresponding to these transducer graphical elements 502 in these rows each are within a target distance. Therefore, in some embodiments, it is determined (e.g., according to the instructions of block 707) that the transducers corresponding to the transducer graphical elements 502 along the other rows (besides rows 510a and 510b) are acceptable for concurrent selection, which results in the display of the corresponding between graphical elements 504.

It should be noted that although the embodiments of FIG. 5J illustrate the unacceptability of concurrency of selection of various transducer pairs latitudinally arranged on a supporting structure due to excessive transducer-to-transducer distance, acceptability of concurrency of selection of transducer pairs or larger groups can be determined on an individual transducer-group basis and based on other factors or other factors in conjunction with transducer-to-transducer distance. For example, a transducer-based device (e.g., similar to transducer-based device 300) represented by a graphical representation in FIG. 5J may contort when placed in a bodily cavity, and therefore, transducer-to-transducer distances may vary between transducer pairs in some directions (e.g., across regions of space that do not include a physical portion of the supporting structure). Therefore, in some embodiments, the transducer-to-transducer distances are calculated in real time for each possible transducer pair via transducer data received according to the instructions of block 704, and based at least upon this transducer data, each possible transducer pair is identified as being acceptable or not acceptable for concurrent selection according to the instructions of block 707, and the corresponding between graphical elements are consequently displayed or not displayed in the graphical representation. In some embodiments, a particular transducer pair is identified as being acceptable or not acceptable for concurrent selection according to the instructions of block 707 on the basis of other factors in addition to the transducer-to-transducer distance associated with the particular transducer pair (e.g., location of the transducer pair to a particular anatomical feature).

Further, in some embodiments, acceptability of concurrency of selection need not be performed on a transducer-pair-basis. For example, in some of these embodiments, a group of three or more transducers that could form one possible ablation path could be evaluated as a group to determine whether all transducers within that group are acceptable for concurrent selection, e.g., to determine whether a possible ablation path is acceptable of activation (e.g., ablation). In this regard, in some embodiments, the instructions of block 707 are configured to cause identification, for each of a plurality of transducer sets of three or more transducers (e.g., each representing a possible ablation path), whether or not all transducers within the corresponding transducer set are acceptable for concurrent selection.

Having discussed the identification of transducer sets that are acceptable and transducer sets that are not acceptable for concurrent selection according to the instructions of block 707, a discussion of some embodiments of graphical element selection and activation according to the instructions of blocks 710 and 712 in FIG. 7A will now be discussed with respect to FIG. 7B.

Figure 7B:
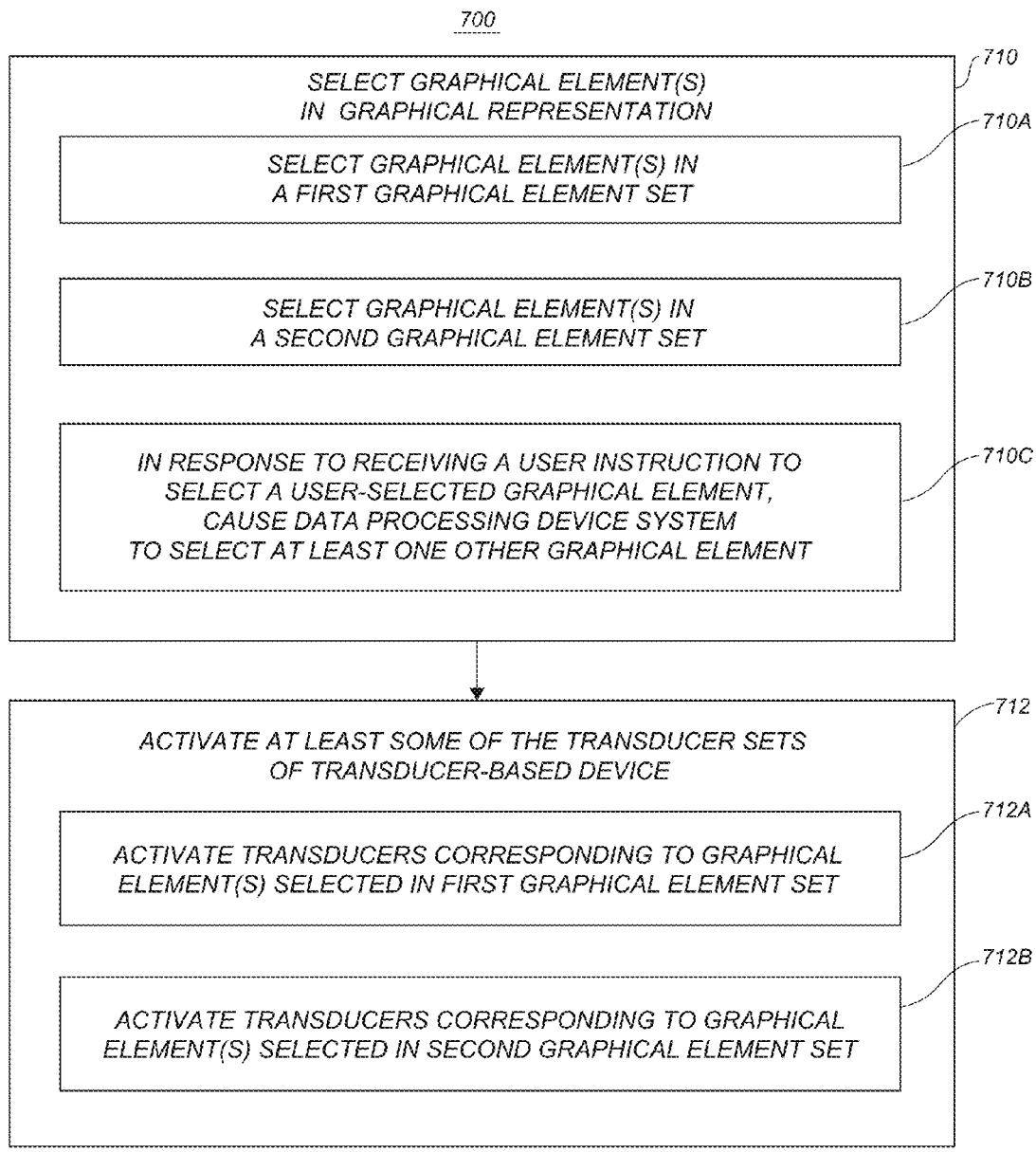
FIG. 7B illustrates an exploded view of some of the blocks of the block diagram of FIG. 7A according to some example embodiments.

FIG. 7B includes an exploded view of the selection instructions of block 710 and the activation instructions of block 712 according to some example embodiments. In some embodiments, all of the blocks shown in FIG. 7B may not be required. Block 710A includes first selection instructions (e.g., instructions provided in a program) configured to cause selection (e.g., a first selection) of at least one graphical element in a first graphical element set of a plurality of graphical element sets. In some embodiments, the first graphical element set is associated with a first one of the sets of two or more of the transducers whose respective transducers have been identified according to the instructions of block 707 to be acceptable for concurrent selection, and the first selection instructions are configured to cause concurrent selection, in response to the selection of the at least one graphical element in the first graphical element set, of the respective transducers of the first one of the sets of two or more of the transducers. However, identification of the respective transducers as acceptable for concurrent selection, and concurrent selection of the respective transducers may not be required in some embodiments.

For example, a user might directly select a between graphical element such as a between graphical element 504 or 604 (i.e., the between graphical element is a user-selected between graphical element), which might cause the first selection instructions to cause the data processing device system to (a) perform a machine-selection of the user-selected between graphical element (e.g., by changing its visual characteristics), and (b) perform a machine-selection (or in some embodiments, a concurrent selection) of the transducers in a transducer pair corresponding to the user-selected between graphical element. In some embodiments, the transducer pair is identified to be acceptable for concurrent selection. In some embodiments, the machine-based selection of the transducer pair may lead to an activation (or in some embodiments, a concurrent activation) of the transducers of that pair (e.g., block 712A, discussed below). In some embodiments, including, but not limited to embodiments where the user directly selects a between graphical element (i.e., the between graphical element is user-selected), the machine-selection(s) may or may not include a machine-selection of a transducer graphical element. In some embodiments, the first selection does not include a user-selected transducer graphical element. In some embodiments, including, but not limited to embodiments where the user directly selects a between graphical element, the selection of the at least one graphical element in the first graphical element set according to the instructions of block 710A is a selection, at one time, of each of the at least one graphical element in the first graphical element set. For example, the user directly selects, at one time, a between graphical element via a mouse click with the cursor above the between graphical element, which causes a corresponding machine selection, at one time, of the user-selected between graphical element, e.g., by changing a visual characteristic of the user-selected between graphical element. Although the above-discussion regarding block 710A includes examples involving both a user graphical element selection and a machine graphical element selection, some embodiments involve only a machine graphical element selection at block 710A.

Block 710B includes second selection instructions configured to cause selection (e.g., a second selection as opposed to the first selection discussed above with respect to block 710A) of at least one graphical element in a second graphical element set of the graphical element sets. In some embodiments, the second graphical element set is associated with a second one of the sets of two or more of the transducers whose respective transducers have been identified according to the instructions of block 707 to be not acceptable for concurrent selection, and the second selection instructions are configured to cause non-concurrent selection, in response to the selection of the at least one graphical element in the second graphical element set, of the respective transducers of the second one of the sets of two or more of the transducers. However, identification of the respective transducers as not acceptable for concurrent selection, and non-concurrent selection of the respective transducers are not required in some embodiments. In some embodiments, the selection of the at least one graphical element in the second graphical element set is a selection, over a time interval, of at least two of the graphical elements in the second graphical element set.

For example, a user might directly select a first transducer graphical element such as a first transducer graphical element 502 or 604 (i.e., the first transducer graphical element is a user-selected transducer graphical element), which might cause the second selection instructions to cause the data processing device system to (a1) perform a selection (or machine selection) of the user-selected first transducer graphical element (e.g., by changing its visual characteristics), and (b1) select the transducer corresponding to the user-selected first transducer graphical element. Then, the user might directly select a second transducer graphical element such as a second transducer graphical element 502 or 604 (i.e., the second transducer graphical element is a user-selected transducer graphical element), which might cause the second selection instructions to cause the data processing device system to (a2) perform a selection (or machine selection) of the user-selected second transducer graphical element (e.g., by changing its visual characteristics), and (b2) select the transducer corresponding to the user-selected second transducer graphical element. Accordingly, in some embodiments, the user-selections of the first and second transducer graphical elements over a time interval cause the corresponding machine-selections of the first and second transducer graphical elements over a time interval. In some embodiments, these machine selections (b1) and (b2) of the transducers corresponding to the user-selected first and second transducer graphical elements are non-concurrent selections. In some embodiments, the machine-based selections (b1) and (b2) of the transducers corresponding to the user-selected first and second transducer graphical elements may lead to an activation (or in some embodiments, a non-concurrent activation) of such transducers (e.g., block 712, discussed below).

In some embodiments, the second graphical element set selected according to the instructions of block 710B has a different number of graphical elements than the first graphical element set selected according to the instructions of block 710A. For example, the second graphical element set selected according to the instructions of block 710B could include two transducer graphical elements 502, while the first graphical element set selected according to the instructions of block 710A could include, in some embodiments, only a between graphical element 504 or, in other embodiments, two transducer graphical elements 502 and a between graphical element 504.

Block 712A shown in FIG. 7B includes activation instructions (e.g., instructions provided in a program) configured to cause activation of the transducers corresponding to the first graphical element set selected according to the instructions of block 710A. Block 712B shown in FIG. 7B includes activation instructions (e.g., instructions provided in a program) configured to cause activation of the transducers corresponding to the second graphical element set selected according to the instructions of block 710B.

In some embodiments, the activation instructions of block 712A include activation instructions configured to, in response to the concurrent selection of the respective transducers of the first one of the sets of two or more of the transducers cause concurrent activation, via the input-output device system (e.g., input-output device system 120 or 320), of each of the respective transducers of the first one of the sets of two or more of the transducers. In some embodiments, the concurrent activation may include monopolar activation of each of the respective transducers of the first one of the sets of two or more of the transducers. In some embodiments, the concurrent activation may include bipolar activation between the respective transducers of the first one of the sets of two or more of the transducers. The monopolar or bipolar activation of the respective transducers of the first one of the sets of two or more of the transducers may include sufficient energy being delivered from an energy source device system (e.g., energy source device system 340) to each of the respective transducers of the first one of the sets of two or more of the transducers, the energy sufficient to cause ablation of tissue in a bodily cavity. In some of these embodiments, conditions allow for the energy to be sufficient to cause an electrophysiological activity conduction block to be formed in the tissue between the respective transducers of the first one of the sets of two or more of the transducers.

In some embodiments, the activation instructions of block 712B include second activation instructions configured to, in response to the non-concurrent selection of the respective transducers of the second one of the sets of two or more of the transducers cause non-concurrent activation, via the input-output device system, of each of the respective transducers of the second one of the sets of two or more of the transducers. In some embodiments, the activation instructions of block 712B include second activation instructions configured to, in response to the non-concurrent selection of the respective transducers of the second one of the sets of two or more of the transducers, preclude bipolar activation, via the input-output device system, between the respective transducers of the second one of the sets of two or more of the transducers. In various embodiments, selection instructions (e.g., the selection instructions of block 808) allow for the concurrent selection of a pair of transducers by the selection of a particular between graphical element 504 made in accordance with various aspects of method 700.

In some embodiments associated with FIG. 7B, a first selection of at least one of the graphical elements 501 (e.g., between graphical element 504*a* shown in FIG. 5F, for example) from a first graphical element set is caused according to first selection instructions (e.g., instructions of block 710A) to select a first pair of transducers made up of a first transducer and a second transducer (e.g., transducers 306). FIG. 5F is considered to include a group of transducer graphical elements 502, and in some of these embodiments, the first selection may not include a user selection of any user-selected transducer graphical elements 502 in the group (e.g., the first selection could be for the between graphical element 504*a* in cases where the first selection is only for transducer pairs deemed to be concurrently selectable according to the instructions of block 707).

In some embodiments, a second selection of at least one of the graphical elements 501 in FIG. 5F is caused according to second selection instructions (e.g., instructions of block 710B) to select a second pair of the transducers made up of the first transducer and a third transducer. For example, in some embodiments, the second selection may not include a user selection of any user-selected transducer graphical elements 502 (e.g., the second selection could be for the between graphical element 504*d* in cases where the second selection is only for transducer pairs deemed to be concurrently selectable according to the instructions of block 707). In some embodiments, the second selection may not include a user selection of any user-selected between graphical elements 504 (e.g., the second selection could be for at least a selected transducer graphical element (e.g., transducer graphical element 502*f* shown in FIG. 5F) in cases where the second selection is only for transducer pairs deemed to be not-concurrently selectable according to the instructions of block 707). In various embodiments, each of the first, the second, and the third transducers are different transducers which respectively correspond to transducer graphical elements 502*a*, 502*b* and 502*f*. In various embodiments, each of the first pair of transducers and the second pair of transducers (each selected by respective ones of the first selection according to the instructions of block 710A and the second selection according to the instructions of block 710B, for example) is an adjacent pair of transducers in a distribution of transducers. In some embodiments, the second selection includes a selection of at least two transducer graphical elements in the group (e.g., transducer graphical elements 502f and 502a).

As stated above, a first spatial relationship between the plurality of transducer graphical elements 502 in the graphical representation of FIG. 5F, for example, may be consistent with a second spatial relationship between corresponding ones of the transducers in the distribution. In some embodiments, each of between graphical elements 504a and 504d is associated with a respective region of space that does not include a physical portion of a structure on which the transducers are located (e.g., structure 308). In other embodiments, at least one of the first pair and the second pair of transducers may correspond to a between graphical element 504 that is associated with a region of space that includes a physical portion of the structure. Such distinctions can be important, as discussed herein, in determining the acceptability of concurrency of selection of graphical elements and transducers, the acceptability of activation of transducers, the duration of activation, and for other reasons discussed herein.

As discussed above, the selections according to the instructions of blocks 710A and 710B can occur by way of any combination of one or more machine-based constituent selections and, optionally or additionally, user-based constituent selections. In some embodiments, each of the first selection (e.g., according to the instructions of block 710A) and the second selection (e.g., according to the instructions of block 710B) includes a user-selected graphical element 501 selected by a user according to a user instruction (e.g., a user-based constituent selection, as discussed above) to select the user-selected graphical element 501. In some embodiments, the first selection, the second selection, or each of the first selection and the second selection does not include a selection of a user-selected transducer graphical element 502 made in response to a user instruction to select the transducer graphical element. For instance, a user may instruct selection of a between graphical element 504, which can cause a machine-based selection of a pair of transducer graphical elements 502 that correspond to the user-selected between graphical element 504, and, optionally, a machine-based selection of a pair of transducers that correspond to the pair of transducer graphical elements 502. In some embodiments, the second selection does not include a selection of a user-selected transducer graphical element 502 made in response to a user instruction to select the transducer graphical element.

While in some embodiments, both the first selection (e.g., according to the instructions of block 710A) and the second selection (e.g., according to the instructions of block 710B) do not include a selection of a user-selected transducer graphical element made 502 in response to a user selection to select the user-selected transducer graphical element 502, in other embodiments, the second selection may include a selection of at least one user-selected between graphical element 504 (e.g., 504d) (e.g., made in response to a user-instruction to select the at least one user-selected between graphical element).

Block 710C shown in FIG. 7B includes third selection instructions employed in some embodiments, the third selection instructions configured to, in response to receiving a user instruction to select at least one user-selected graphical element, cause the data processing device system (e.g., data processing device system 110 or 310) to a select at least one other graphical element. In one particular embodiment, the third selection instructions are configured to cause the data processing device system to select at least a second graphical element (e.g., transducer graphical elements 502a and 502b) in response to a user instruction to select between graphical element 504a. In this particular embodiment, the third selection instructions are configured to select at least a third graphical element (e.g., transducer graphical elements 502a and 502f) in response to a user instruction to select the user-selected between graphical element 504d. Visual characteristics of user-selected graphical elements and graphical elements selected by the data processing device system in response to receiving a user instruction to select at least one user-selected graphical element may be changed as discussed above. In some embodiments, the first activation instructions of block 712A, the second activation instructions of block 712B or each of the first and the second activation instructions include instructions configured to cause activation of a corresponding one of the sets of two or more of the transducers in response to the selection of at least one graphical element made by the data processing device system in response to at least receiving a user instruction to select at least one user-selected graphical element.

Having discussed identifying the acceptability of concurrency of selection of transducer sets with respect to block 707 and corresponding subsequent selection of transducer graphical elements and activation of corresponding transducers pursuant to FIG. 7B, block 708 in FIG. 7A will now be described. Block 708 can include, in some embodiments, instructions provided by a program to cause the data processing device system to identify activation-ready transducers and not-activation-ready transducers based at least upon an analysis of transducer data (e.g., received according to the instructions of block 704). For example, in some embodiments, if the analysis of the transducer data indicates that certain transducers are located above an anatomical feature that should not be ablated, those certain transducers are identified according to the instructions of block 708 to be not-activation-ready transducers. Another example of not-activation-ready transducers includes those that have insufficient contact with tissue to properly ablate or acquire tissue characteristics, as determined, for example, according to measurements (e.g., various electrical, force, or pressure measurements) represented in the transducer data. The instructions according to block 708 include, in some embodiments, instructions configured to cause the graphical representation displayed according to the instructions of block 702 to visually distinguish the not-activation-ready transducers from the activation-ready transducers.

In this regard, block 708 includes, in some embodiments, instructions (e.g., identification instructions) provided by a program configured to cause the data processing device system to identify activation-ready transducers of the transducer-based device as transducers deemed, based at least on an analysis of the transducer data (e.g., received according to the instructions of block 704), acceptable for activation (e.g., activation according to the instructions of block 712), and not-activation-ready transducers of the transducer-based device as transducers deemed, based at least on the analysis of the transducer data, not acceptable for activation (e.g., activation according to the instructions of block 712).

Figure 8:
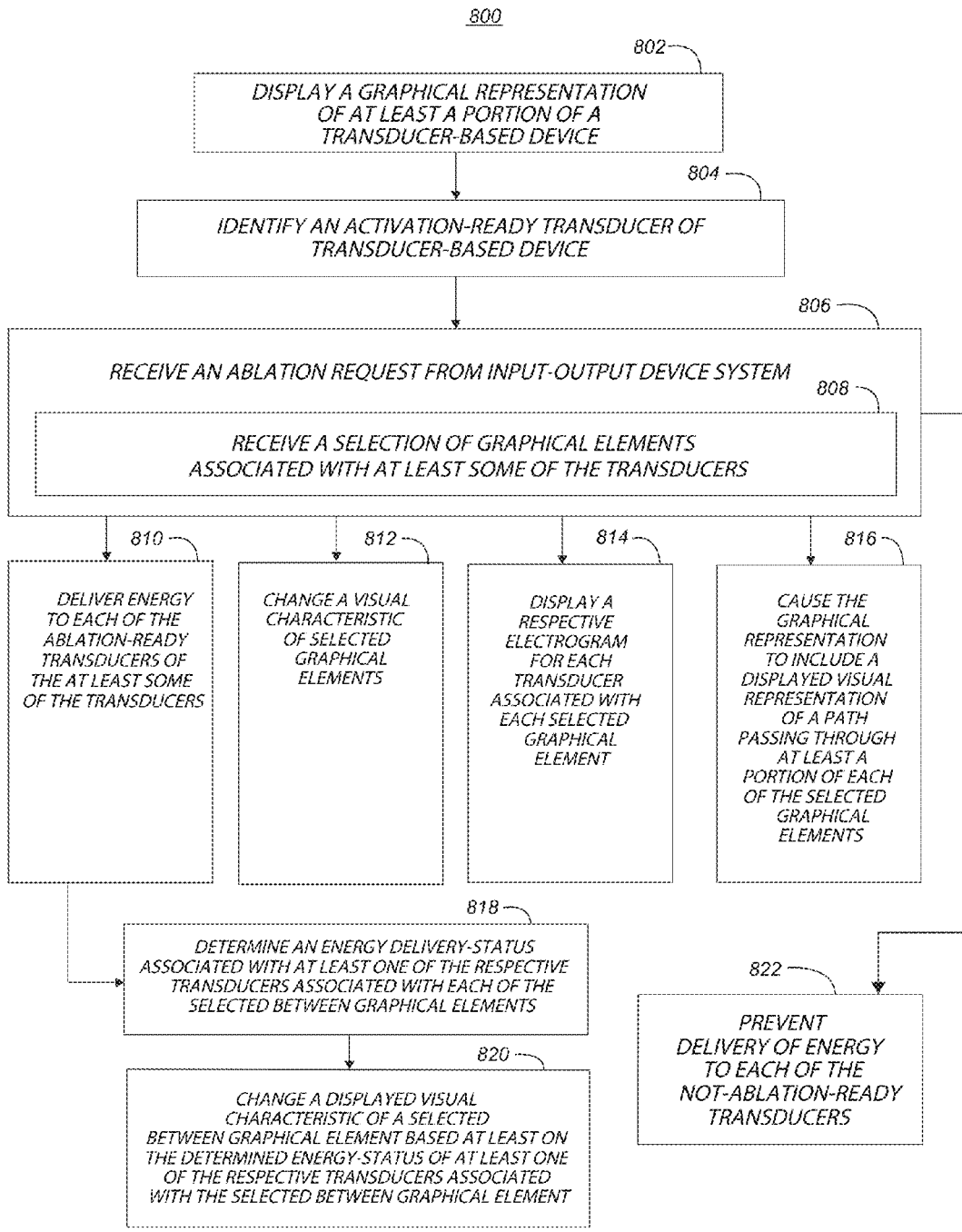
FIG. 8 illustrates a block diagram of a method for activating transducers of a transducer-based device according to various example embodiments.

As discussed above, the identification of activation-ready transducers and not-activation-ready transducers of a transducer-based device in accordance with the instructions of block 708 can take different forms. In this regard, block 804 in FIG. 8 provides an example of the instructions of block 708 in FIG. 7A, according to some embodiments. It should be noted that block 802 corresponds to block 702 in some embodiments, blocks 806 and 808 correspond to block 710 in some embodiments, and block 810 corresponds to block 712 in some embodiments. However, in some embodiments, FIG. 8 stands on its own independently of FIG. 7A. In this regard, the method 800 pertains to ablation-causing activations, although it is understood that other forms of activation may be employed in other embodiments. Reference to at least some of FIG. 5 continues with the discussion of FIG. 8 for convenience of discussion. In some embodiments, method 800, like method 700, may include a subset of the associated blocks or additional blocks than those shown. In addition, in some embodiments, method 800, like method 700, may include a different sequence between various ones of the associated blocks than those shown in FIG. 8.

The example of block 804, in some embodiments, includes instructions (e.g., identification instructions provided by a program) configured to identify an activation-ready transducer of the transducer-based device (e.g., transducer-based devices 100, 300, 400) as a transducer that is associated with or adjacent a region of space deemed, based at least on an analysis of the transducer data, acceptable for ablation. In some embodiments, this "adjacent region of space" is a region of space that includes matter that would be activated, ablated, or otherwise interacted with by the corresponding transducer due to ablation activation or other activation of the corresponding transducer. In some embodiments, a region of space is determined, in view of an analysis of the transducer data, to be acceptable for ablation or activation of a corresponding transducer set, when the region of space is not determined to be unacceptable for ablation or activation. In some embodiments, a region of space is determined, in view of an analysis of the transducer data, to be not acceptable for ablation or activation of a corresponding transducer set, when all or particular matter in the region of space may be negatively or unacceptably negatively impacted by the ablation or activation of the corresponding transducer set. In some embodiments, block 804 includes instructions (not shown, e.g., identification instructions provided by a program) configured to cause identification of an activation-ready transducer of the transducer-based device (e.g., transducer-based devices 100, 300, 400) as a transducer that is deemed, based at least on an analysis of the transducer data, to be located within sufficient proximity to a region of space, the sufficient proximity deemed acceptable for ablation. In some embodiments, this sufficient proximity is deemed to require contact between the transducer and the tissue to be ablated.

In some embodiments, block 804 also includes instructions (e.g., identification instructions provided by a program) configured to identify a not-activation-ready transducer of the transducer-based device as a transducer that is adjacent a region of space deemed, based at least on the analysis of the transducer data, not acceptable for ablation. In some embodiments, block 804 includes instructions (not shown, e.g., identification instructions provided by a program) configured to identify a not-activation-ready transducer of the transducer-based device (e.g., transducer-based devices 100, 300, 400) as a transducer that is deemed, based at least on an analysis of the transducer data, not within sufficient proximity to a region of space, the sufficient proximity deemed acceptable for ablation.

It is understood that a transducer may be identified as an activation-ready transducer or not-activation-ready transducer on the basis of other criteria in other embodiments. In some embodiments, activation-ready transducers are referred to as ablation-ready transducers and not-activation-ready transducers are referred to as not-ablation-ready transducers. In some embodiments, at least two of the ablation-ready transducers or at least two of the not-ablation-ready transducers may be located on a same structural member (e.g., an elongate member 304) of a transducer-based device. In some embodiments, at least two of the ablation-ready transducers or at least two of the not-ablation-ready transducers may be located on different structural members (e.g., different elongate members 304) of a transducer-based device. These differences can be important as transducers along a structural member may have different ablation characteristics than transducers located on different structural members that have no physical portion of the transducer based device between them. For example, ablation along structural members may have, for example, different insulating effects on ablation as compared to ablation between structural members.

In some embodiments where the transducer-based device or a portion thereof is receivable or positionable in a bodily cavity, the instructions of block 804 may include instructions configured to require that, in order for a region of space to be deemed acceptable for ablation, the region of space be determined, based at least on the analysis of the transducer data (e.g., received according to the instructions of block 704, which may be part of block 804 or between blocks 802 and 804 in some embodiments), to be associated with a tissue in the bodily cavity that is acceptable for ablation. The instructions of block 804 may include instructions configured to require that, in order for a region of space to be deemed not acceptable for ablation, the region of space be determined, based at least on the analysis of the transducer data, to be associated with a tissue in the bodily cavity that is not acceptable for ablation. In some embodiments, the bodily cavity is an intra-cardiac cavity and the tissue in the bodily cavity that is not acceptable for ablation is blood.

In some embodiments where the transducer-based device or a portion thereof is receivable or positionable in a bodily cavity, the instructions of block 804 may include instructions configured to require that, in order for a region of space to be deemed acceptable for ablation, the region of space be determined, based at least on the analysis of the transducer data, to be associated with an anatomical feature of the bodily cavity that is acceptable for ablation. The instructions of block 804 may include instructions configured to require that, in order for a region of space to be deemed not acceptable for ablation, the region of space be determined, based at least on the analysis of the transducer data, to be associated with an anatomical feature of the bodily cavity that is not acceptable for ablation (e.g., a pulmonary vein).

In some embodiments where the transducer-based device or a portion thereof is receivable or positionable in a bodily cavity that includes a tissue wall surface interrupted by one or more ports in fluid communication with the bodily cavity, the instructions of block 804 may include instructions configured to require that, in order for a region of space to be deemed not acceptable for ablation, the region of space be determined, based at least on the analysis of the transducer data, to overlie a least part of a port of the one or more ports.

Referring back to FIGS. 5C and 5D, the various regions 525 are associated with regions of space deemed not suitable or acceptable for ablation while various other regions of the graphical representation that exclude regions 525 are associated with regions of space deemed suitable for ablation in this illustrated embodiment. In some embodiments, like the above-discussion with respect to blocks 708 and 702, regions of space deemed suitable for ablation can be visually distinguished from the regions of space deemed not suitable for ablation in the graphical representation displayed according to the instructions of block 802. In this regard, the graphical representation instructions for visually distinguishing the regions of space deemed suitable for ablation from the regions of space deemed not suitable for ablation may reside in block 804 or in 802, according to some embodiments. In any event, these graphical representation instructions (e.g., graphical representation instructions included in a program) may be configured, in some embodiments, to cause an input-output device system (e.g., input-output device system 120 or 320) to display a graphical representation of at least a portion of a transducer-based device.

In some embodiments, like the above-discussion with respect to blocks 708 and 702, the graphical representation instructions may include instructions configured to cause the input-output device system to display the graphical elements 501 that are associated with transducer sets including the ablation-ready transducers with a first set of visual characteristics and to display the graphical elements 501 that are associated with transducer sets including the not-ablation-ready transducers with a second set of visual characteristics different than the first set of visual characteristics. In some embodiments, the first set of visual characteristics, the second set of visual characteristics, or both the first and the second sets of visual characteristics each includes a plurality of different visual characteristics. Different visual characteristics can include different colors, opacities, hues, intensities, shading, patterns, shapes or the addition or removal of any displayed information suitable for distinguishing an ablation-ready transducer from a not-ablation-ready transducer. In the embodiment of FIGS. 5C and 5D, transducer graphical elements 502 that are positioned over any of the regions 525 (e.g., transducer graphical elements 502 associated with not-ablation-ready transducers) are displayed with different visual characteristics (e.g., a thick line circle in this embodiment) than the transducers graphical elements 502 that are not positioned over any of the regions 525 (e.g., transducer graphical elements 502 associated with the ablation-ready transducers).

In the embodiment illustrated in FIGS. 5C and 5D, only the between graphical elements 504 that are each associated with a corresponding set of transducers (e.g., a corresponding pair of transducers in this embodiment) that includes only ablation-ready transducers are displayed. In the embodiment illustrated in FIGS. 5C and 5D, only the between graphical elements 504 that are each associated with a respective region of space that is located between a corresponding pair of transducers that includes only ablation-ready transducers are displayed. In the embodiment illustrated in FIGS. 5C and 5D, only the between graphical elements 504 that are each associated with a respective region of space that does not include any transducer and does not include any portion of a region of spaced deemed, based at least on the transducer data, not acceptable for ablation are displayed.

In the embodiment illustrated in FIGS. 5C and 5D, each of the between graphical elements 504 that is associated with a corresponding set of transducers (e.g., a corresponding pair of transducers in this embodiment) that includes at least one not-ablation-ready transducers is not displayed. In the embodiment illustrated in FIGS. 5C and 5D, each of the between graphical elements 504 that is associated with a region of space between a corresponding pair of transducers that includes at least one not-ablation-ready transducer is not displayed. In the embodiment illustrated in FIGS. 5C and 5D, each of the between graphical elements 504 that is associated with a region of space that does not include any transducer but does include a portion of a region of spaced deemed, based at least on the transducer data, not acceptable for ablation (e.g., a region 525) is not displayed.

Moving on to a discussion of blocks 806 and 808 in FIG. 8, which may correspond to block 710 in some embodiments, block 806 of method 800 includes ablation request instructions (e.g., instructions provided by a program) configured to cause the data processing device system (e.g., data processing device systems 110 or 310) to process an ablation request received from the input-output device system, the ablation request configured to request ablation by at least some of the plurality of transducers of the transducer-based device.

In some embodiments, the ablation request associated with block 806 may be considered part of a selection of one or more graphical elements according to the instructions of block 710 in FIG. 7A in some embodiments. Block 808 represents instructions associated with such a selection according to some embodiments. As discussed above, the selection instructions associated with block 710 may configure the data processing device system to receive a selection, via the input-output device system (e.g., again exemplified by input-output device system 120 or 320) of at least some of the graphical elements (e.g., graphical elements 501, 601) provided in the graphical representation. In some embodiments, the selection instructions associated with block 710 cause the data processing device system to receive, via the input-output device system, a selection of at least some of the graphical elements 501 associated with the transducers including activation-ready transducers. Block 808, in some embodiments, includes selection instructions (e.g., instructions provided in a program), which configure the data processing device system (e.g., again exemplified by data processing device systems 110 or 310) to cause selection of various graphical elements. In some embodiments, the caused selection includes receiving, via the input-output device system (e.g., again exemplified by input-output device systems 120, 320) a selection of the graphical elements 501 associated with at least some of the transducers, the at least some of the transducers including ablation-ready transducers. In some embodiments, each of the graphical elements 501 associated with the at least some of the transducers is independently selectable. For example, as shown in FIG. 5E, first between graphical element 504*a* positioned between the first and the second transducer graphical elements 502*a*, 502*b* respectively identified by identification labels 513 as "Q:6" and "R:6" has been selected via the input-output device system. In this example embodiment, the ablation request instructions of block 806 include the instructions of block 808. In this example embodiment, the ablation request associated with the instructions of block 806 is made at least in part by making a selection of the at least some of the graphical elements 501 associated with the instructions of block 808.

It is noted that in some embodiments (e.g., embodiments where ablation-ready transducers and not-ablation-ready transducers are selectable in accordance with blocks 806 or 808), the method 800 may include determination instructions (e.g., instructions provided by a program) (not shown, but could be shown connected (immediately) downstream of block 806 and (immediately) upstream of block 822) configured to cause the data processing device system to determine whether an ablation-requested transducer set including the at least some of the plurality of transducers selected in accordance with blocks 806 or 808 includes a not-ablation-ready transducer. In this case, the method 800 may include ablation denial instructions (e.g., instructions provided in a program) configured to, if it is determined according to the determination instructions that the ablation-requested transducer set includes the not-ablation-ready transducer, deny the ablation request. In some embodiments, the ablation denial instructions are configured to deny the ablation request at least with respect to the not-ablation-ready transducer in the ablation-requested transducer set if it is determined according to the determination instructions that the ablation-requested transducer set includes the not-ablation-ready transducer. In some embodiments, the ablation denial instructions can take a form of non-activation instructions (e.g., instructions provided by a program) associated with block 822 in FIG. 8, which, in some embodiments, are configured to cause the data processing device system to prevent energy from the energy source device system from being delivered to each of the plurality of not-ablation-ready transducers identified according to block 804 or block 708. An example of preventing energy from being delivered would be for the data processing device system to reject all or a portion of an instruction received, for example, from a user via the input-output device system, to perform ablation involving not-ablation ready transducers.

Block 812 of method 800 includes instructions (e.g., instructions provided in a program) configured to, in response to receiving independent selections of graphical elements in accordance with block 808, cause the input-output device system to change a visual characteristic of the selected graphical elements 501 during a time interval that occurs during the receiving of the independent selections, after a completion of the receiving of the independent selections, or both during the receiving of the independent selections and after a completion of the receiving of the independent selections. In some embodiments, the selected graphical elements 501 include a selected between graphical element 504a as shown in FIG. 5E. Changing the visual characteristic of the selected between graphical element 504a may include changing a color, opacity, hue, intensity, shading, pattern, shape or the addition or removal of any displayed information suitable for indicating that the selection has occurred. In this embodiment, the selected between graphical element 504a is modified to include an elongated graphical portion 530 having differing visual characteristics. In some embodiments, block 812 can include additional instructions configured to cause the input-output device system to change a visual characteristic of at least one (e.g., both in this illustrated embodiment) of the first and the second transducer graphical elements 502a, 502b respectively identified by identification labels 513 as "Q:6" and "R:6" during the time interval. In this example embodiment a thicker border is provided around each of the first and the second transducer graphical elements 502a, 502b upon receiving the selection.

In a similar fashion, a visual characteristics of others of the graphical elements 501 (e.g., including transducer graphical elements 502) may change upon their selection in accordance with the instructions of block 808. For example, as shown in FIG. 5F additional between graphical elements 504 (e.g., including second between graphical 504b) have been selected in accordance with the instructions of block 808 with the visual characteristics of the selected additional between graphical elements 504 changing in accordance with the instructions of block 812. For clarity, only the identification labels 513 associated with the transducer graphical elements 502 associated with the pair of transducers associated with each of the selected between graphical elements 504 is shown in FIGS. 5E and 5F. In this illustrated embodiment, each of the selected between graphical elements 504 in FIGS. 5E and 5F were independently selected.

It should be noted that, although the above discussion regarding changing of visual characteristics occurs within the context of FIG. 8, block 812, such discussion can also apply to any discussions herein regarding changing of visual characteristics in some embodiments.

Block 814 of method 800 includes instructions (e.g., instructions provided in a program) configured to cause the input-output device system to display a respective electrogram 535 (only two called out in each of FIGS. 5E and 5F) for each transducer of the pair of transducers associated with each of the selected between graphical elements 504 (e.g., selected according to the instructions of block 808 or 710). In this example embodiment, each electrogram 535 is identified with an identifier 536 that provides information corresponding to the identification label 513 associated with a respective one of the transducer graphical elements 502. In this example embodiment, each electrogram 535 is provided on the basis of transducer data provided by a transducer of the respective pair of transducers associated with a selected between graphical element 504. In this example embodiment, a single electrogram 535 would also be displayed if a transducer graphical element 502 were to be individually selected, the single electrogram 535 being provided on the basis of transducer data provided by the respective transducer associated with the selected single transducer graphical element 502. In some example embodiments, block 814 includes instructions configured to cause the input-output device system to display a combined electrogram (e.g., a bipolar electrogram) from the pair of transducers associated with each of the selected between graphical elements 504. It is noted that some of the electrograms 535 not shown in the graphical representation shown in FIG. 5F may be viewed by operation of scroll bar 528 via the input-output device system. It is also noted that, although block 814 is shown as immediately following an ablation request according to block 806, block 814, in some embodiments, is not dependent upon receipt of an ablation request, and may operate independently any time a graphical element is selected.

Block 816 of method 800 includes path-display instructions (e.g., instructions provided in a program) configured to, in response to receiving the independent selections (e.g., selected according to the instructions of block 808 or 710) of between graphical elements 504, cause the graphical representation to include a displayed visual representation of a path 537 passing through at least a portion of each of the selected between graphical elements 504, during a time interval that occurs (a) during the receiving of the independent selections, (b) after a completion of the receiving of the independent selections, or both (a) and (b). In this embodiment, the displayed visual representation of the path extends between at least two of the plurality of rows 510 and between at least two of the plurality of columns 512. In this embodiment, path 537 surrounds a region 525 (e.g., one of the regions 525c). In this example embodiment, path 537 is a contiguous path. In this example embodiment, path 537 is a closed path. In this embodiment, the path display instructions of block 816 are further configured to cause the displayed visual representation of the path 537 to pass through at least some of the transducer graphical elements 502 associated with the transducers between which the regions of space associated with the selected between graphical elements 504 respectively reside. In some example embodiments (e.g., a visual or graphical representation (e.g., 600 in FIG. 6) provided by a graphical interface (e.g., FIG. 6)), the displayed visual representation of the path 537 includes a path segment that proceeds diagonally between a first node located at a first junction of a first one of the plurality of columns (e.g., columns 612) and a first one of the plurality of rows (e.g., rows 610) and a second node located at a second junction of a second one of the plurality of columns (e.g., columns 612) and a second one of the plurality of rows (e.g., rows 610), the first junction being different than the second junction. In this embodiment the path-display instructions of block 816 include instructions configured to cause the displayed graphical representation to change, during the time interval, a visual characteristic of the selected between graphical element 504 at least as part of forming the displayed visual representation of the path 537 (e.g., via elongated portion 530 in this embodiment). In this example embodiment, the path-display instructions of block 816 include instructions configured to cause the displayed graphical representation to change, during the time interval, a visual characteristic of at least some of the transducer graphical elements 502 associated with the transducers in the pairs of the transducers between which the regions of space associated with the selected between graphical elements 504 respectively reside. In some embodiments, the path 537 represents an ablation path or proposed or intended ablation path.

Block 810 of method 800 (which could represent a particular subset of implementations of block 712 in FIG. 7A in some embodiments) includes activation instructions (e.g., instructions provided in a program) configured to, in response to receiving the ablation request from the input-output device system, cause, via the input-output device system, energy from an energy source device system (e.g., energy source device system 340) to be delivered to each of the ablation-ready transducers of the at least some of the transducers in which ablation was requested by as per block 806, the activation instructions configured to cause the energy delivery to occur during the time interval. In this example embodiment, a selection of the control button 538 (called out in FIG. 5G) identified as "Ablate" in response to a user action via the input-output device system can cause execution of the activation instructions. In this example embodiment, the activation instructions of block 810 of method 800 include instructions (e.g., instructions provided in a program) configured to, in response to receiving the independent selections of between graphical elements 504 in accordance with selection instructions included in block 808, cause activation, via the input-output device system, of each of the pairs of the transducers between which the respective regions of space associated with the selected between graphical elements 504 respectively reside, the activation instructions configured to cause the activation to occur during the time interval. In this embodiment, the activation instructions include instructions configured to, in response to receiving the independent selections of the between graphical elements 504 cause energy from the energy source device system (e.g., energy source device system 340) to deliver energy to each of the pairs of the transducers between which the regions of space associated with the selected between graphical elements 504 respectively reside, the activation instructions configured to cause the energy delivery to occur during the time interval. In this example embodiment, the energy is tissue-ablation energy and the path 537 is representative of an ablation path. In some embodiments, the activation instructions include instructions configured to, in response to receiving the independent selections of the between graphical elements 504 cause monopolar activation of the transducers in each of the pairs of the transducers between which the regions of space associated with the selected between graphical elements 504 respectively reside, the activation instructions configured to cause the monopolar activation to occur during the time interval. In some embodiments, the activation instructions include instructions configured to, in response to receiving the independent selections of the between graphical elements 504 cause bipolar activation between the respective transducers in each of the pairs of the transducers between which the regions of space associated with the selected between graphical elements 504 respectively reside, the activation instructions configured to cause the bipolar activation to occur during the time interval. In this regard, the energy may be delivered in a manner that (a) a portion of the energy delivered to a first transducer of each pair of the transducers is transmitted by the first transducer, (b) a portion of the energy delivered to a second transducer of each pair of the transducers is transmitted by the second transducer, or both (a) and (b). In this regard, an indifferent electrode may be arranged to receive a portion of the energy delivered to at least one of the transducers of each of the pairs of the transducers between which the regions of space associated with the selected between graphical elements 504 respectively reside.

Figure 9:
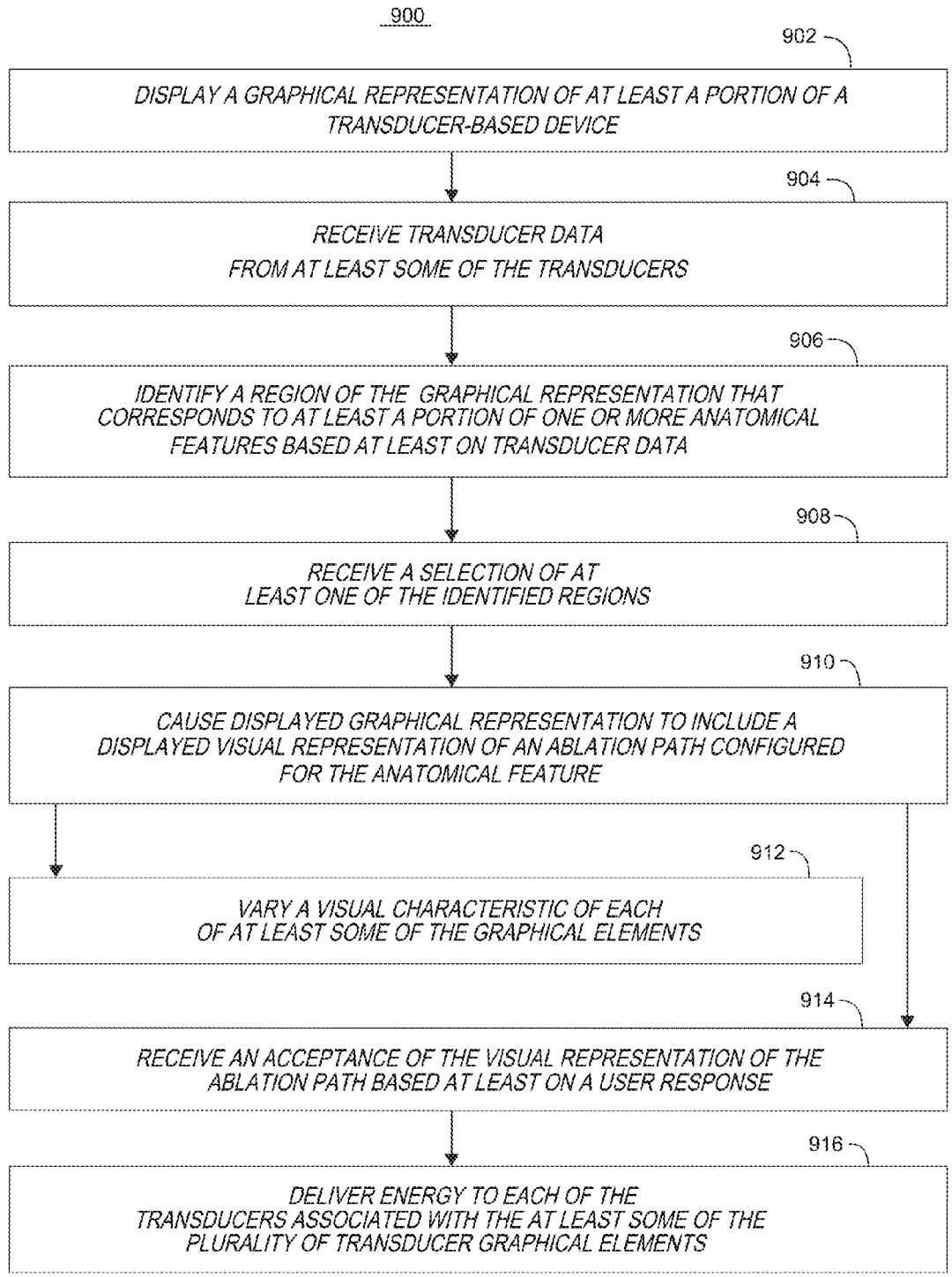
FIG. 9 illustrates a block diagram of a method for displaying a visual representation of an ablation path according to various example embodiments.

In some embodiments, selection of various graphical elements (e.g., graphical elements 501, 601) is not required to provide a visual representation of an ablation path (e.g., path 537). For example, FIG. 9 is a block diagram showing a method 900 including instructions (e.g., instructions provided in a program) for displaying a visual representation of an ablation path. Reference to the instructions provided by at least some of the blocks associated with method 700 is made for comparison purposes. Reference to various ones of FIG. 5 including transducer graphical elements 502 and between graphical elements 504 continues to be made for convenience of discussion. In some embodiments, method 900 may include a subset of the associated blocks or additional blocks than those shown in the FIG. 9. In some embodiments, method 900 may include a different sequence between various ones of the associated blocks than those shown in FIG. 9.

In a manner similar to block 702, block 902 of method 900 includes instructions (e.g., graphical representation instructions or graphical interface instructions included in a program) configured to cause an input-output device system (e.g., input-output device system 120 or 320) to display a graphical representation of at least a portion of a transducer-based device (e.g., transducer-based devices 200, 300, or 400). FIG. 5A illustrates a graphical interface provided by the input-output device system according to one example embodiment provided in accordance with block 902. The graphical interface of FIG. 5A includes a graphical representation 500 that includes a plurality of transducer graphical elements 502 and a plurality of between graphical elements 504, each characterized as per above. In a manner similar to block 704, block 904 of method 900 includes instructions (e.g., input instructions included in a program) that cause the data processing device system (e.g., data processing device systems 110 or 310) to receive transducer data from at least some of the transducers via the input-output device system.

In a manner similar to block 706, block 906 of method 900 includes instructions (e.g., identification instructions included in a program) that are configured to identify a region of the graphical representation that corresponds to at least a portion of one or more anatomical features based at least on the transducer data. In this example embodiment, a plurality of identified regions 525 is shown in the three-dimensional graphical representation provided by the graphical representation 500 of FIG. 5C and the two-dimensional graphical representation provided by the graphical representation 500 of FIG. 5D, each of the identified regions corresponding to a particular anatomical feature as previously discussed (e.g., ports related to various pulmonary veins, left lateral appendage and mitral valve).

Block 908 of method 900 includes selection instructions (e.g., instructions provided in a program) configured to cause the data processing device system (e.g., data processing device systems 110 or 310) to receive a selection from the input-output device system of at least one of the identified regions 525. Block 910 of method 900 includes path-display instructions (e.g., instructions provided in a program) configured to, in response to receiving the selection of the at least one of the identified regions, causes the displayed graphical representation to include a displayed visual representation of an ablation path configured for the anatomical feature.

Referring to FIG. 5D, a region 525 (e.g., region 525c) corresponding to a pulmonary vein of the left pulmonary vein group has been selected via the input-output device system. Again, various input-output device system components including a touch screen, keyboard or computer mouse may be employed to make the selection by way of non-limiting example. A path 537 defining an ablation path around the selected region 525c is automatically generated in response to the selection of region 525c in accordance with the path display instructions of block 910.

Unlike the embodiment of FIG. 8, where an ablation path is defined by a user, the ablation path associated with the embodiment of FIG. 9 is defined by the data-processing device system. This can be accomplished in various ways. In this example embodiment, transducer data from the transducer-based device is used to help define each of the particular regions 525 as well as additional regions other than the regions 525 that can accommodate an ablation path configured for the anatomical feature corresponding to a selected region. In this example embodiment, the visual representation of the ablation path (e.g., represented by path 537) passes at least proximate to each of at least some the transducer graphical elements 502 associated with the transducers associated with the particular ones of the additional regions positioned at least proximate region 525c. In some example embodiments, the visual representation of the ablation path passes at least proximate to each of at least some of the between graphical elements 504 (e.g., through the between graphical elements 504 in this embodiment) associated with pairs of the transducers associated with the particular ones of the additional regions positioned at least proximate region 525c. In some example embodiments, at least some of the transducers are deemed anatomical feature-specific transducers (e.g., transducers associated with a particular one of the anatomical features) based at least on the transducer data while others of the transducers are deemed not-anatomical feature-specific transducers (e.g., transducers not associated with a particular one of the anatomical features) based at least on the transducer data. In various example embodiments, method 900 includes instructions (not shown) (e.g., instructions provided in a program) configured to cause the data processing device system to determine the ablation path based at least on a determination of a proximity of various ones of the not-anatomical feature-specific transducers to various ones of the anatomical feature-specific features associated with an anatomical feature corresponding to selected region 525. In some of these various example embodiments, the path-display instructions of block 910 includes instructions configured to, in response to receiving the selection of the at least one of the identified regions, cause the displayed graphical representation to include the displayed visual representation of an ablation path configured for the anatomical feature based at least on (a) an identification of the transducer graphical elements 502 associated with the various ones of the not-anatomical feature-specific transducers, (b) an identification of the between graphical elements 504 associated with pairs of the various ones of the not-anatomical feature-specific transducers, or both (a) and (b).

In this example embodiment, the path-display instructions are configured to, in response to receiving the selection of the identified region 525c, cause the displayed visual representation of the ablation path to surround the identified region 525c. In this example embodiment, the path-display instructions are configured to, in response to receiving the selection of the identified region 525c, cause the displayed visual representation of the ablation path to continuously surround the identified region 525c. In some example embodiments, the respective ablation paths associated with different ones of at least two selected ones of the identified regions 525 may have different configurations (e.g., shape, continuity). In some example embodiments, the transducer data includes data associated with an electrical characteristic (e.g., impedance) of tissue within a bodily cavity in which the transducer based-device or a portion thereof is receivable or positionable. In some example embodiments, the transducer data includes data associated with a flow characteristic of fluid within a bodily cavity in which the transducer-based device or a portion thereof is receivable or positionable.

In this example embodiment, block 912 of method 900 includes instructions (e.g., instructions provided in a program) configured to, in response to receiving the selection of the identified region 525, cause the input-output device system to vary a visual characteristic of each of at least some of the graphical elements 501. In this example embodiment, a visual characteristic of each of at least some of the transducer graphical elements 502 and each of at least some of the between graphical elements 504 is changed.

In this example embodiment, block 914 of method 900 includes path-acceptance instructions (e.g., instructions provided in a program) configured to cause the data processing device system to receive an acceptance of the visual representation of the ablation path based at least on a user response via the input-output device system.

In this example embodiment, block 916 of method 900 includes activation instructions (e.g., instructions provided in a program) configured to, in response to receiving the acceptance, cause, via the input-output device system, energy from an energy source device system (e.g., energy source device system 340) to be delivered to each of the transducers associated with the at least some of the plurality of transducer graphical elements 502, the energy sufficient for ablating tissue. Ablation can include monopolar ablation, or bipolar ablation or combinations thereof.

Figure 10:
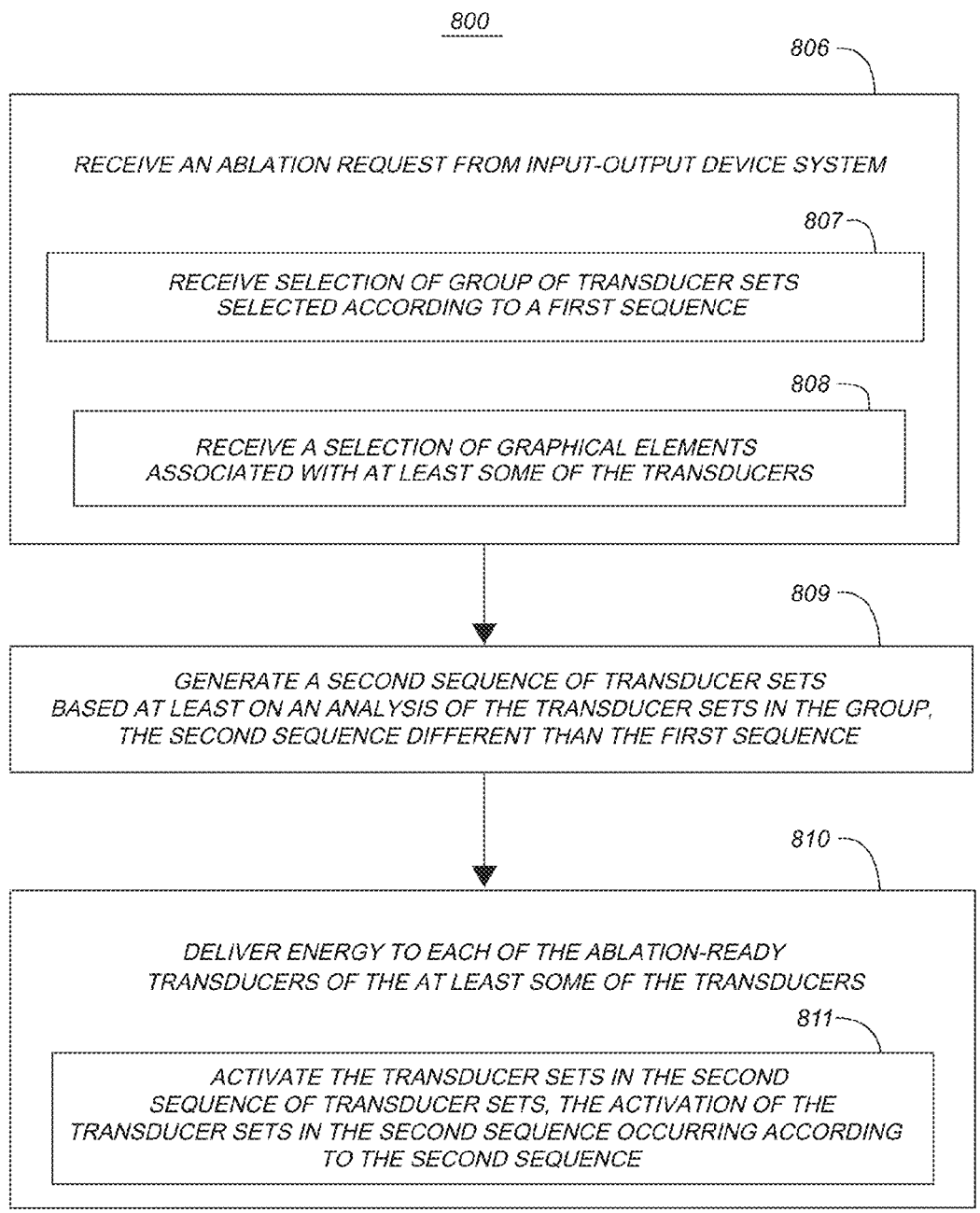
FIG. 10 illustrates an exploded view of some of the blocks of the block diagram of FIG. 8, according to some example embodiments.

FIG. 10 is an exploded view of the blocks 806 and 810 of a version of method 800 according to some example embodiments. In some embodiments, the ablation request instructions of block 806 include instructions (e.g., reception instructions provided in a program) as per block 807 configured to receive a selection from the input-output device system of a group of transducer sets, each of the sets of the group of the transducer sets including at least one of the transducers of the transducer-based device (e.g., transducer-based devices 200, 300, or 400). In these embodiments, each of the transducer sets is selected according to a first sequence. In some embodiments, at least part of the selection according to block 807 occurs by a selection of graphical elements, such that the instructions of block 808 are configured to cause the data processing device system (e.g., again exemplified by data processing device systems 110 or 310) to receive, via the input-output device system (e.g., again exemplified by input-output device systems 120, 320) a selection of at least some of the graphical elements 501 associated with some or all of the plurality of transducer sets discussed above with respect to block 807. In some example embodiments, each of the transducer graphical elements 502 associated with the plurality of transducer sets is selected according to the first sequence. For example, as shown in FIG. 5F, the transducer graphical elements 502 associated with path 537 may be selected in a sequential fashion in the following order (e.g., each selected transducer graphical element 502 indicated by the corresponding identification labels 513: "R:6", "Q:6", "P:6", "P:7", "O:7", "O:8", "O:9", "P:9", "P:10", "Q:10", "R:10", "R:9", "S:9", "S:8", "S:7", and "R:7" to select the plurality of transducer sets according to the first sequence. In such embodiments, each transducer set may be considered to have a single transducer. Also, as shown in FIG. 5F, the between graphical elements 504 associated with path 537 may be selected in a sequential fashion in the following order (e.g., each selected between graphical element 504 herein identified by the corresponding pair of identification labels 513 associated with the transducer graphical elements 502 in which the selected between graphical element 504 is positioned between): "R:6-Q:6", "Q:6-P:6", "P:6-P:7", "P:7-O:7", "O:7-O:8", "O:8-O:9", "O:9-P:9", "P:9-P:10", "P:10-Q:10", "Q:10-R:10", "R:10-R:9", "R:9-S:9", "S:9-S:8", "S:8-S:7", "S:7-R:7" and "R:7-R:6" to select the plurality of transducer sets according to the first sequence. In such embodiments, each transducer set may be considered to have at least two transducers. In this embodiment, each of the selected between graphical elements 504 is associated with a region of space between a pair of transducers that include the respective first and second transducers which make up a respective set of group of transducer sets. It is noted that the first sequence can take other forms in other embodiments. For example, the transducer sets may be selected randomly or pseudo-randomly according to the first sequence. In other embodiments, the first sequence may not require successively adjacent transducers in a distribution of the transducers to be selected as described above.

In various embodiments, each of the transducer sets in the first sequence form part of a group of the transducer sets. In various embodiments, various transducer sets in a group of transducer sets are selected according to a first sequence (e.g., the first sequence described above with regard to block 807) with at least two of the transducer sets in the group sequentially selected. In accordance with the discussion above, in at least some of these various embodiments, each of at least some of the selected transducer sets in the group includes at least one transducer different than each of the other transducer sets in the group. In at least some of these various embodiments, each of at least some of the transducer sets in the group includes at least two transducers. In at least some of these various embodiments, each of at least some of the transducer sets in the group includes a respective pair of adjacent ones of the transducers in a distribution of the transducers. The respective pair of adjacent ones of the transducers of each of the at least some of the transducer sets in the group may have a same transducer as the respective pair of adjacent ones of the transducers of another of the at least some of the of the transducer sets in the group. In some of these various embodiments, at least a first transducer set in the group has a same transducer as a second transducer set in the group. In at least some of these various embodiments, two or more of the transducers in a given one of the transducer sets may be selected concurrently (e.g., a pair of transducers selected by a selection of a between graphical element 504, 604 as described above). In at least some of these various embodiments, two or more of the transducer sets in the group may also be selected concurrently in the first sequence. In at least some of these various embodiments, an additional transducer set may be selected concurrently with one of the at least two of the transducer sets sequentially selected according to the first sequence. Transducer sets in the group that include different numbers of transducers or different transducers may be selected according to the first sequence. For example, the first sequence may indicate at least (a) a selection (e.g., by a selection of a transducer graphical element 502, 602) of a first transducer in a first transducer set in the group followed by a selection (e.g., by a selection of a between graphical element 504, 604) of a pair of second and third transducers in a second transducer set in the group, (b) a selection (e.g., by a selection of a between graphical element 504, 604) of a pair of fourth and fifth transducers in a third transducer set in the group followed by a selection (e.g., by a selection of a transducer graphical element 502, 602) of a sixth transducer in a fourth transducer set in the group, or both (a) and (b).

In some embodiments, the activation instructions of block 810 of method 800 includes activation instructions as per block 811 (e.g., instructions provided in a program) configured to cause sequential activation, initiated during or after completion of a generation of a second sequence of transducer sets (discussed below), of the transducer sets in the second sequence of transducer sets. The activation of the transducer sets in the second sequence occurs according to the second sequence, and the activation instructions are configured to cause activation of at least one transducer in each of the sequentially activated sets. In one particular embodiment, the activation of instructions of block 811 are configured to cause activation of the transducer sets of a group of transducer sets according to a second sequence different than the first sequence in which the transducer sets of the group of transducers sets were selected.

The second sequence may be determined in various manners. For example, in some embodiments, method 800 may include a block 809 (e.g., shown in FIG. 10, not shown in FIG. 8) that includes generation instructions (e.g., instructions provided in a program) configured to, in response to receiving at least part of the first sequence, cause a generation (e.g., via a data processing device system such as data processing device systems 110 or 310) of the second sequence of transducer sets based at least on an analysis of the transducer sets in a group of which the transducer sets in the first sequence form at least part.

We now turn to embodiments that vary visual characteristics of graphical elements during transducer activation processes. For example, the activation instructions as per block 811 in method 800 in FIG. 10, can include activation instructions configured to, in response to receiving at least part of a selection of various between graphical elements 504 associated with each of a plurality of transducer sets selected according to a first sequence, cause, via the input-output device system, energy from an energy source device system (e.g., energy source device system 340) to be delivered to each of the transducer sets according to a second sequence different than the first sequence. In some embodiments, during this energy delivery process, visual characteristics of the selected between graphical elements 504 can be varied to illustrate to a user a status of the energy delivery process. It should be noted, however, that the variances of visual characteristics described herein need not apply only to the method 800 or to the selection of between graphical elements 504, but can also apply to any activation process and to any graphical element according to the various embodiments described herein. The method 800 and between graphical elements 504 are only used for illustration purposes.

In this regard, FIGS. 5G and 5H, show example sequential variances in visual characteristics of respective ones of the between graphical elements 504 associated with at least some of the transducers sets as they are activated according to the second sequence. Changes in the visual characteristics are highlighted in accordance with a KEY provided in each of FIGS. 5G, 5H and 5I. It is understood that the KEY is provided for illustrative purposes and does not form part of the graphical representation in this example embodiment. As discussed above, variances in visual characteristics may include changing a color, opacity, hue, intensity, shading, pattern, shape or the addition or removal of any displayed information.

FIG. 5G is associated with a condition in which energy is being delivered (e.g., according to the second sequence) to the respective transducer set associated with the first between graphical element 504a (e.g., previously identified as "R:6-Q:6" and to the respective transducer set associated with another between graphical element 504 (e.g., previously identified as "P:10-Q:10") while energy is not delivered to the respective transducer sets associated with the remaining ones of the selected between graphical elements 504. It is noted that the energy delivered to the transducer set associated with the between graphical element 504 previously identified as "P:10-Q:10" is not delivered according to the sequence it was selected with respect to the other of the transducer sets. It is noted that the respective electrograms 535 associated with the respective transducers of at least some of the transducer sets to which energy is delivered (e.g., the transducer set associated with the between graphical element 504 previously identified as "P:10-Q:10") are repositioned in the graphical representation for enhanced viewing during the energy delivery (e.g., as best compared between FIGS. 5F and 5G).

FIG. 5H is associated with a condition in which the energy delivery has been completed to respective transducer sets associated with each of the between graphical elements 504 previously identified as "R:6-Q:6" and "P:10-Q:10". FIG. 5H is associated with a condition in which energy is being delivered to the respective transducer sets associated with the between graphical elements 504 previously identified as "R:9-S:9" and "S:7-R:7" while energy is not delivered to the other respective transducer sets that have not yet received energy or the other respective transducer sets in which the energy delivery has been completed. Again, it is noted that the energy delivered to the transducer sets associated with the between graphical elements 504 previously identified as "R:9-S:9" and "S:7-R:7" is not delivered according to the first sequence in which these transducer sets were selected with respect to the others of the group of transducer sets. In this example embodiment, the energy delivery process according to the remainder of the second sequence continues, until energy has been delivered to all of the remaining selected transducer sets as exemplified in FIG. 5I. It is noted that for brevity of illustration, energy delivery to every one of the selected remaining transducer sets in accordance with the remainder of the second sequence has not been shown.

In this example embodiment, the activation instructions of blocks 810, 811 cause the transmission of energy-delivery instructions (not shown) to cause energy from the energy source device system to be delivered to each of the respective first transducer and second transducer of the corresponding transducer set associated with each of the selected between graphical elements 504. FIG. 8 includes a block 818 that includes determination instructions (e.g., instructions provided by a program) configured to determine an energy-delivery status associated with at least one of the respective first transducer and the respective second transducer associated with each of the selected between graphical elements 504, the energy delivery status indicating a status of the energy delivery by the energy source device system to the at least one of the respective first transducer and the respective second transducer. In some embodiments, the energy delivery status includes a status of a portion of the energy delivered by the energy source device system to the at least one of the respective first transducer and the respective second transducer, the portion of the energy transmitted by the at least one of the respective first transducer and the respective second transducer. FIG. 8 includes a block 820 that includes energy delivery indication instructions configured to cause the input-output device system to change a displayed visual characteristic of a selected between graphical element 504 based at least on the determined energy-status of the at least one of the respective first transducer and the respective second transducer. For example, referring to FIG. 5G, the energy delivery status associated with the at least one of the respective first and the respective second transducers associated with the selected between graphical element 504a previously identified as "R:6-Q:6" includes a during-energy delivery status associated with a state during the energy delivery by the energy source device system to the at least one of the first transducer and the second transducer associated with the selected between graphical element 504a previously identified as "R:6-Q:6". The energy delivery status associated with the at least one of the respective first and second transducers associated with the selected between graphical element 504 previously identified as "S:7-R:7" includes a pre-energy-delivery status associated with a state before a start of energy delivery by the energy source device system to the at least one of the first transducer and the second transducer associated with the selected between graphical element 504 previously identified as "S:7-R:7". As shown in FIG. 5G, a first displayed visual characteristic of the between graphical elements 504 is associated with the pre-energy-delivery status (e.g., the selected between graphical element 504 previously identified as "S:7-R:7") and a second displayed visual characteristic of the between graphical elements 504 is associated with the during-energy-delivery status (e.g., the selected between graphical element 504 previously identified as "R:6-Q:6"), the second displayed visual characteristic being different than the first displayed visual characteristic. Differences in the displayed visual characteristics may include different colors, opacities, hues, intensity, shading, patterns, shapes or any suitable addition or removal of any displayed information sufficient for characterizing the difference. In some embodiments, the first displayed visual characteristic of a between graphical element 504 associated with the pre-energy delivery status is different than a visual characteristic of the between graphical element 504 resulting upon a selection of the between graphical element 504 (e.g., as per block 812). In this embodiment, the first displayed visual characteristic of a between graphical element 504 associated with the pre-energy delivery status is the same as a visual characteristic of the between graphical element 504 resulting upon a selection of the between graphical element 504. It is noted that in this example embodiment that the between graphical element 504a previously identified as "R:6-Q:6" included the first displayed visual characteristic prior to energy delivery to the corresponding ones of the transducers.

In FIG. 5H, the energy delivery status associated with the at least one of the first transducer and the second transducer associated with the between graphical element 504a previously identified as "R:6-Q:6" includes a post-energy-delivery status associated with a state after a completion of the energy delivery from the energy source device system to the at least one of the first transducer and the second transducer associated with the between graphical element 504a previously identified as "R:6-Q:6". In FIG. 5H, a pre-energy-delivery status is associated with at least some of the between graphical elements (e.g., the between graphical element 504 previously identified as "P:7-O:7") and a during-energy-delivery status is associated with at least some of the between graphical elements (e.g., the between graphical element 504 previously identified as "S:7-R:7"). In this example embodiment, a third displayed visual characteristic of the between graphical elements 504 associated with the post-energy delivery-state (e.g., the between graphical element 504a previously identified as "R:6-Q:6") is different than at least one (e.g., both in this example embodiment) of the first displayed visual characteristic of the between graphical elements 504 associated with the pre-energy delivery-state (e.g., the between graphical element 504 previously identified as "P:7-O:7") and the second displayed visual characteristic of the between graphical elements 504 associated with the during-energy delivery-state (e.g., the between graphical element 504 previously identified as "S:7-R:7"). In FIG. 5I all of the selected between graphical elements 504 are shown with the third displayed visual characteristic, indicating that completion of the energy delivery to their respective transducer sets has occurred. In this example embodiment, the displayed visual characteristics of at least some of the respective transducer graphical elements 502 associated with the respective first and the second transducers associated with each selected between graphical elements undergo changes in accordance with changes in the energy delivery state. The displayed visual characteristics associated with the various energy-delivery states are depicted in accordance with the KEY provided in each of FIGS. 5G, 5H and 5I.

While some of the embodiments disclosed above are described with examples of cardiac mapping, the same or similar embodiments may be used for mapping other bodily organs, for example gastric mapping, bladder mapping, arterial mapping and mapping of any lumen or cavity into which the devices of the present invention may be introduced.

While some of the embodiments disclosed above are described with examples of cardiac ablation, the same or similar embodiments may be used for ablating other bodily organs or any lumen or cavity into which the devices of the present invention may be introduced.

Subsets or combinations of various embodiments described above can provide further embodiments.

These and other changes can be made to the invention in light of the above-detailed description. In general, in the following claims, the terms used should not be construed to limit the invention to the specific embodiments disclosed in the specification and the claims, but should be construed to include other transducer-based device systems including all medical treatment device systems and all medical diagnostic device systems in accordance with the claims. Accordingly, the invention is not limited by the disclosure, but instead its scope is to be determined entirely by the following claims.

What is claimed is:

1. A medical system comprising:
    a data processing device system;
    an input-output device system communicatively connected to the data processing device system; and
    a memory device system communicatively connected to the data processing device system and storing a program executable by the data processing device system, the program comprising:
    input instructions configured to cause reception of transducer data via the input-output device system, the transducer data indicating data acquired by at least some of a plurality of transducers included in a transducer-based device system, at least part of the transducer-based device system positionable within a bodily cavity;
    graphical representation and identification instructions configured to cause the input-output device system to display a graphical representation based at least on an analysis of the transducer data that identifies a region in the graphical representation that corresponds to at least a portion of an anatomical feature;
    selection instructions configured to cause processing of a selection of the identified region; and
    path-display instructions configured to, in response to the selection, cause the displayed graphical representation to include a displayed visual representation of an ablation path configured for the anatomical feature.

2. The medical system of claim 1 wherein the displayed graphical representation comprises a plurality of transducer graphical elements respectively associated with at least a group of the plurality of transducers of the transducer-based device system.

3. The medical system of claim 2 wherein the at least part of the transducer-based device system comprises the group of the plurality of transducers.

4. The medical system of claim 1 wherein the transducer data indicates data acquired at least in part from particular ones of the plurality of transducers that are positionable in the bodily cavity.

5. The medical system of claim 1 wherein the displayed visual representation of the ablation path surrounds the identified region in the graphical representation.

6. The medical system of claim 1 wherein the displayed visual representation of the ablation path continuously surrounds the identified region in the graphical representation.

7. The medical system of claim 1 wherein the displayed visual representation of the ablation path corresponds to a path arranged to surround at least the portion of the anatomical feature.

8. The medical system of claim 1 wherein the transducer-based device system comprises a catheter device, and wherein the anatomical feature is an anatomical feature that forms at least part of the bodily cavity.

9. The medical system of claim 8 wherein the bodily cavity comprises a tissue wall surface interrupted by one or more ports in fluid communication with the bodily cavity, and wherein the anatomical feature includes at least one port of the one or more ports.

10. The medical system of claim 1 wherein multiple ones of the at least some of the plurality of transducers are arranged in a distribution, the multiple ones of the plurality of transducers positionable within the bodily cavity, and wherein the transducer data includes data associated with an electrical characteristic of tissue in the bodily cavity.

11. The medical system of claim 10 wherein the electrical characteristic is an electrical impedance of the tissue in the bodily cavity.

12. The medical system of claim 1 wherein the transducer data indicates electrical impedance information.

13. The medical system of claim 1 wherein multiple ones of the at least some of the plurality of transducers are arranged in a distribution, the multiple ones of the plurality of transducers positionable within the bodily cavity, and wherein the transducer data includes data associated with a flow characteristic of fluid in the bodily cavity.

14. The medical system of claim 1 wherein the transducer data indicates positional information of at least the part of the transducer-based device system relative to one or more anatomical features, including the anatomical feature, in the bodily cavity.

15. The medical system of claim 14 wherein the bodily cavity is an atrium, and the one or more anatomical features include a pulmonary vein in the atrium.

16. The medical system of claim 14 wherein the transducer data distinguishes tissue from blood.

17. The medical system of claim 1 wherein the selection is from a user.

18. The medical system of claim 2 wherein the displayed visual representation of the ablation path passes through a number of locations in the displayed graphical representation, each of the number of locations positioned in the displayed graphical representation at least proximate a respective one of at least some of the plurality of transducer graphical elements.

19. The medical system of claim 18 wherein the graphical representation and identification instructions comprise instructions configured to, in response to the selection, cause the input-output device system to vary a visual characteristic of each of the at least some of the plurality of transducer graphical elements.

20. The medical system of claim 18 wherein the program further comprises path-acceptance instructions configured to cause the data processing device system to receive an acceptance of the displayed visual representation of the ablation path based at least on a user response communicated via the input-output device system.

21. The medical system of claim 20 wherein the program comprises activation instructions configured to, in response to receiving the acceptance, cause, via the input-output device system, energy from an energy source device system to be delivered to each of the transducers associated with the at least some of the plurality of transducer graphical elements, the energy sufficient for ablating tissue.

22. The medical system of claim 1 wherein the program further comprises path-acceptance instructions configured to cause the data processing device system to receive an acceptance of the displayed visual representation of the ablation path based at least on a user response communicated via the input-output device system.

23. The medical system of claim 22 wherein the program further comprises activation instructions configured to, in response to receiving the acceptance, cause, via the input-output device system, energy sufficient for tissue ablation to be delivered from an energy source device system to each transducer of a set of the plurality of transducers in a state where each transducer of the set of the plurality of transducers is arranged to ablate a respective portion of the ablation path.

24. The medical system of claim 2
wherein the displayed graphical representation comprises
a plurality of between graphical elements, each between graphical element associated with a region of space between a respective pair of the group of the plurality of transducers, each region of space not including any transducer, and no two of the respective pairs of the group of the plurality of transducers having an identical pair of the transducers, and
wherein the graphical representation and identification instructions comprise instructions configured to, in response to the selection, cause the input-output device system to vary a visual characteristic of each of at least some of the plurality of between graphical elements.

25. The medical system of claim 24 wherein the displayed visual representation of the ablation path passes at least proximate to each of the at least some of the plurality of between graphical elements.

26. The medical system of claim 24 wherein the program further comprises:
path-acceptance instructions configured to cause reception of an acceptance of the visual representation of the ablation path based at least on a user response via the input-output device system; and
activation instructions configured to, in response to receiving the acceptance, cause, via the input-output device system, energy from an energy source device system to be delivered to each of the corresponding pairs of the group of the plurality of transducers associated with each of the at least some of the plurality of between graphical elements, the energy sufficient for ablating tissue.

27. The medical system of claim 1 wherein the path-display instructions are configured to cause determination of the visual representation of the ablation path based at least in part on a particular analysis of the transducer data.

28. The medical system of claim 27 wherein the particular analysis of the transducer data includes identifying anatomical feature-specific transducers associated with the anatomical feature and identifying not-anatomical feature-specific transducers not associated with the anatomical feature.

29. The medical system of claim 28 wherein the path-display instructions are configured to cause determination of the ablation path based at least on a determination of a proximity of various ones of the not-anatomical feature-specific transducers to various ones of the anatomical feature-specific transducers associated with the anatomical feature.

30. The medical system of claim 28 wherein the displayed graphical representation comprises a plurality of transducer graphical elements, each transducer graphical element of the plurality of transducer graphical elements respectively associated with a transducer of at least a group of the plurality of transducers of the transducer-based device system, and wherein the graphical representation and identification instructions comprise instructions configured to cause at least some of the plurality of transducer graphical elements which are associated with particular ones of the anatomical feature-specific transducers to be depicted in an overlapping relationship with the identified region in the displayed graphical representation.

31. The medical system of claim 30 wherein the graphical representation and identification instructions comprise instructions configured to cause at least some of the plurality of transducer graphical elements which are associated with particular ones of the not-anatomical feature-specific transducers to be depicted surrounding at least some of the plurality of transducer graphical elements which are associated with the particular ones of the anatomical feature-specific transducers in the displayed graphical representation.

32. The medical system of claim 28
wherein the displayed graphical representation comprises a plurality of transducer graphical elements respectively associated with at least a group of the plurality of transducers of the transducer-based device system,
wherein the displayed graphical representation comprises a plurality of between graphical elements, each between graphical element associated with a region of space between a respective pair of the group of the plurality of transducers, each region of space not including any transducer, and no two of the respective pairs of the group of the plurality of transducers having an identical pair of the transducers,
wherein the graphical representation and identification instructions comprise instructions configured to, in response to the selection, cause the input-output device system to vary a visual characteristic of each of at least some of the plurality of between graphical elements, and
wherein the path-display instructions are configured to, in response to the selection of the identified region, cause the displayed graphical representation to include the displayed visual representation of the ablation path configured for the anatomical feature based at least on (a) an identification of transducer graphical elements of the plurality of transducer graphical elements associated with the various ones of the not-anatomical feature-specific transducers, (b) an identification of between graphical elements of the plurality of between graphical elements associated with pairs of the various ones of the not-anatomical feature-specific transducers, or both (a) and (b).

33. The medical system of claim 1 wherein the program further comprises activation instructions configured to cause, via the input-output device system, energy sufficient for tissue ablation to be delivered from an energy source device system to each transducer of a set of the plurality of transducers in a state where each transducer of the set of the plurality of transducers is proximate a respective portion of the ablation path.

34. The medical system of claim 1
wherein the region is a first region, the anatomical feature is a first anatomical feature, the selection is a first selection, and the ablation path is a first ablation path,
wherein the input instructions are configured to cause reception of second transducer data via the input-output device system, the second transducer data indicating data acquired by one or more transducers of the plurality of transducers,
wherein the graphical representation and identification instructions are configured to cause the input-output device system to display, based at least on an analysis of the second transducer data, the graphical representation as further identifying a second region in the graphical representation that corresponds to at least a portion of a second anatomical feature,
wherein the selection instructions are configured to cause processing of a second selection of the identified second region, and
wherein the path-display instructions are configured to, in response to the second selection, cause the displayed graphical representation to include a displayed visual representation of a second ablation path configured for the second anatomical feature.

35. The medical system of claim 34 wherein the first ablation path and the second ablation path have different configurations.

36. The medical system of claim 34 wherein the first ablation path and the second ablation path have different shapes.

37. The medical system of claim 34 wherein the first ablation path is continuous, and the second ablation path is not continuous.

38. A medical system comprising:
a data processing device system;
an input-output device system communicatively connected to the data processing device system; and
a memory device system communicatively connected to the data processing device system and storing a program executable by the data processing device system,
wherein the data processing device system is configured by the program at least to:
receive transducer data via the input-output device system, the transducer data indicating data acquired by at least some of a plurality of transducers included in a transducer-based device system, at least part of the transducer-based device system positionable within a bodily cavity;
cause the input-output device system to display a graphical representation based at least on an analysis of the transducer data that identifies a region in the graphical representation that corresponds to at least a portion of an anatomical feature;
process a selection of the identified region; and
cause, in response to the selection, the displayed graphical representation to include a displayed visual representation of an ablation path configured for the anatomical feature.

39. A method executed by a data processing device system according to a program stored by a memory device system communicatively connected to the data processing device system, the data processing device system further communicatively connected to an input-output device system, the method comprising:
receiving transducer data via the input-output device system, the transducer data indicating data acquired by at least some of a plurality of transducers included in a transducer-based device system, at least part of the transducer-based device system positionable within a bodily cavity;
causing the input-output device system to display a graphical representation based at least on an analysis of the transducer data that identifies a region in the graphical representation that corresponds to at least a portion of an anatomical feature;
processing a selection of the identified region; and
causing, in response to the selection, the displayed graphical representation to include a displayed visual representation of an ablation path configured for the anatomical feature.

40. A non-transitory computer-readable storage medium system comprising one or more non-transitory computer-readable storage mediums storing a program executable by one or more data processing devices of a data processing device system communicatively connected to an input-output device system, the program comprising:
an input module configured to cause reception of transducer data via the input-output device system, the transducer data indicating data acquired by at least some of a plurality of transducers included in a transducer-based device system, at least part of the transducer-based device system positionable within a bodily cavity;

a graphical representation and identification module configured to cause the input-output device system to display a graphical representation based at least on an analysis of the transducer data that identifies a region in the graphical representation that corresponds to at least a portion of an anatomical feature;

a selection module configured to cause processing of a selection of the identified region; and a path-display module configured to, in response to the selection, cause the displayed graphical representation to include a displayed visual representation of an ablation path configured for the anatomical feature.

41. A medical system comprising:
a data processing device system;
an input-output device system communicatively connected to the data processing device system; and
a memory device system communicatively connected to the data processing device system and storing a program executable by the data processing device system, the program comprising:
input instructions configured to cause reception of transducer data via the input-output device system, the transducer data indicating data acquired by at least some of a plurality of transducers included in a transducer-based device system, at least part of the transducer-based device system positionable within a bodily cavity;
graphical representation instructions configured to cause the input-output device system to display a graphical representation that identifies a region in the graphical representation that corresponds to at least a portion of an anatomical feature in the bodily cavity; and
path-display instructions configured to, based at least on an analysis of the transducer data, automatically cause the displayed graphical representation to include a displayed visual representation of an ablation path configured for the anatomical feature.

42. The medical system of claim 41 wherein the displayed graphical representation comprises a plurality of transducer graphical elements respectively associated with at least a group of the plurality of transducers of the transducer-based device system.

43. The medical system of claim 42 wherein the at least part of the transducer-based device system comprises the group of the plurality of transducers.

44. The medical system of claim 41 wherein the transducer data indicates data acquired at least in part from particular ones of the plurality of transducers that are positionable in the bodily cavity.

45. The medical system of claim 41 wherein the displayed visual representation of the ablation path continuously surrounds the identified region in the graphical representation.

46. The medical system of claim 41 wherein the bodily cavity comprises a tissue wall surface interrupted by one or more ports in fluid communication with the bodily cavity, and wherein the anatomical feature includes at least one port of the one or more ports.

47. The medical system of claim 41 wherein the transducer data indicates electrical impedance information.

48. The medical system of claim 41 wherein the transducer data indicates positional information of at least the part of the transducer-based device system relative to one or more anatomical features, including the anatomical feature, in the bodily cavity.

49. The medical system of claim 48 wherein the bodily cavity is an atrium, and the one or more anatomical features include a pulmonary vein in the atrium.

50. The medical system of claim 41 wherein the transducer data distinguishes tissue from blood.

51. The medical system of claim 42 wherein the displayed visual representation of the ablation path passes through a number of locations in the displayed graphical representation, each of the number of locations positioned in the displayed graphical representation at least proximate a respective one of at least some of the plurality of transducer graphical elements.

52. The medical system of claim 51 wherein the graphical representation instructions comprise instructions configured to, in response to the identification of the region in the graphical representation, cause the input-output device system to vary a visual characteristic of each of the at least some of the plurality of transducer graphical elements.

53. The medical system of claim 51 wherein the program further comprises path-acceptance instructions configured to cause the data processing device system to receive an acceptance of the displayed visual representation of the ablation path based at least on a user response communicated via the input-output device system.

54. The medical system of claim 53 wherein the program comprises activation instructions configured to, in response to receiving the acceptance, cause, via the input-output device system, energy from an energy source device system to be delivered to each of the transducers associated with the at least some of the plurality of transducer graphical elements, the energy sufficient for ablating tissue.

55. The medical system of claim 41 wherein the program further comprises path-acceptance instructions configured to cause the data processing device system to receive an acceptance of the displayed visual representation of the ablation path based at least on a user response communicated via the input-output device system.

56. The medical system of claim 55 wherein the program further comprises activation instructions configured to, in response to receiving the acceptance, cause, via the input-output device system, energy sufficient for tissue ablation to be delivered from an energy source device system to each transducer of a set of the plurality of transducers in a state where each transducer of the set of the plurality of transducers is arranged to ablate a respective portion of the ablation path.

57. The medical system of claim 42
wherein the displayed graphical representation comprises a plurality of between graphical elements, each between graphical element associated with a region of space between a respective pair of the group of the plurality of transducers, each region of space not including any transducer, and no two of the respective pairs of the group of the plurality of transducers having an identical pair of the transducers, and wherein the graphical representation instructions comprise instructions configured to, in response to the identification of the region in the graphical representation, cause the input-output device system to vary a visual characteristic of each of at least some of the plurality of between graphical elements.

58. The medical system of claim 57 wherein the displayed visual representation of the ablation path passes at least proximate to each of the at least some of the plurality of between graphical elements.

59. The medical system of claim 57 wherein the program further comprises:

path-acceptance instructions configured to cause reception of an acceptance of the visual representation of the ablation path based at least on a user response via the input-output device system; and activation instructions configured to, in response to receiving the acceptance, cause, via the input-output device system, energy from an energy source device system to be delivered to each of the corresponding pairs of the group of the plurality of transducers associated with each of the at least some of the plurality of between graphical elements, the energy sufficient for ablating tissue.

60. The medical system of claim 41 wherein the graphical representation instructions and the path-display instructions are configured to cause the input-output device system to display the graphical representation that identifies the region and that includes the displayed visual representation based at least in part on a particular analysis of the transducer data.

61. The medical system of claim 41 wherein the analysis of the transducer data includes identifying anatomical feature-specific transducers associated with the anatomical feature and identifying not-anatomical feature-specific transducers not associated with the anatomical feature.

62. The medical system of claim 61 wherein the path-display instructions are configured to cause determination of the ablation path based at least on a determination of a proximity of various ones of the not-anatomical feature-specific transducers to various ones of the anatomical feature-specific transducers associated with the anatomical feature.

63. The medical system of claim 61 wherein the displayed graphical representation comprises a plurality of transducer graphical elements, each transducer graphical element of the plurality of transducer graphical elements respectively associated with a transducer of at least a group of the plurality of transducers of the transducer-based device system, and wherein the graphical representation instructions comprise instructions configured to cause at least some of the plurality of transducer graphical elements which are associated with particular ones of the anatomical feature-specific transducers to be depicted in an overlapping relationship with the identified region in the displayed graphical representation.

64. The medical system of claim 63 wherein the graphical representation instructions comprise instructions configured to cause at least some of the plurality of transducer graphical elements which are associated with particular ones of the not-anatomical feature-specific transducers to be depicted surrounding at least some of the plurality of transducer graphical elements which are associated with the particular ones of the anatomical feature-specific transducers in the displayed graphical representation.

65. The medical system of claim 61
wherein the displayed graphical representation comprises a plurality of transducer graphical elements respectively associated with at least a group of the plurality of transducers of the transducer-based device system,
wherein the displayed graphical representation comprises a plurality of between graphical elements, each between graphical element associated with a region of space between a respective pair of the group of the plurality of transducers, each region of space not including any transducer, and no two of the respective pairs of the group of the plurality of transducers having an identical pair of the transducers,
wherein the path-display instructions comprise instructions configured to, based at least on the analysis of the transducer data, cause the input-output device system to vary a visual characteristic of each of at least some of the plurality of between graphical elements, and
wherein the path-display instructions are configured to cause the displayed graphical representation to include the displayed visual representation of the ablation path configured for the anatomical feature based at least on (a) an identification of transducer graphical elements of the plurality of transducer graphical elements associated with the various ones of the not-anatomical feature-specific transducers, (b) an identification of between graphical elements of the plurality of between graphical elements associated with pairs of the various ones of the not-anatomical feature-specific transducers, or both (a) and (b).

66. The medical system of claim 41 wherein the program further comprises activation instructions configured to cause, via the input-output device system, energy sufficient for tissue ablation to be delivered from an energy source device system to each transducer of a set of the plurality of transducers in a state where each transducer of the set of the plurality of transducers is proximate a respective portion of the ablation path.

67. The medical system of claim 41
wherein the region is a first region, the anatomical feature is a first anatomical feature, and the ablation path is a first ablation path,
wherein the input instructions are configured to cause reception of second transducer data via the input-output device system, the second transducer data indicating data acquired by one or more transducers of the plurality of transducers,
wherein the graphical representation instructions are configured to cause the input-output device system to display the graphical representation as further identifying a second region in the graphical representation that corresponds to at least a portion of a second anatomical feature, and
wherein the path-display instructions are configured to, based at least on an analysis of the second transducer data, automatically cause the displayed graphical representation to include a displayed visual representation of a second ablation path configured for the second anatomical feature.

68. The medical system of claim 67 wherein the first ablation path is continuous, and the second ablation path is not continuous.

69. A medical system comprising:
a data processing device system;
an input-output device system communicatively connected to the data processing device system; and
a memory device system communicatively connected to the data processing device system and storing a program executable by the data processing device system,
wherein the data processing device system is configured by the program at least to:
receive transducer data via the input-output device system, the transducer data indicating data acquired by at least some of a plurality of transducers included in a transducer-based device system, at least part of the transducer-based device system positionable within a bodily cavity;
cause the input-output device system to display a graphical representation that identifies a region in the graphical representation that corresponds to at least a portion of an anatomical feature in the bodily cavity; and
automatically cause, based at least on an analysis of the transducer data, the displayed graphical representation to include a displayed visual representation of an ablation path configured for the anatomical feature.

70. A method executed by a data processing device system according to a program stored by a memory device system communicatively connected to the data processing device system, the data processing device system further communicatively connected to an input-output device system, the method comprising:
receiving transducer data via the input-output device system, the transducer data indicating data acquired by at least some of a plurality of transducers included in a transducer-based device system, at least part of the transducer-based device system positionable within a bodily cavity;
causing the input-output device system to display a graphical representation that identifies a region in the graphical representation that corresponds to at least a portion of an anatomical feature in the bodily cavity; and
automatically causing, based at least on an analysis of the transducer data, the displayed graphical representation to include a displayed visual representation of an ablation path configured for the anatomical feature.

71. A non-transitory computer-readable storage medium system comprising one or more non-transitory computer-readable storage mediums storing a program executable by one or more data processing devices of a data processing device system communicatively connected to an input-output device system, the program comprising:
an input module configured to cause reception of transducer data via the input-output device system, the transducer data indicating data acquired by at least some of a plurality of transducers included in a transducer-based device system, at least part of the transducer-based device system positionable within a bodily cavity;
a graphical representation module configured to cause the input-output device system to display a graphical representation that identifies a region in the graphical representation that corresponds to at least a portion of an anatomical feature in the bodily cavity; and
a path-display module configured to, based at least on an analysis of the transducer data, automatically cause the displayed graphical representation to include a displayed visual representation of an ablation path configured for the anatomical feature.

* * * * *